United States Patent
Tweedle et al.

(10) Patent No.: US 11,419,951 B2
(45) Date of Patent: Aug. 23, 2022

(54) PEPTIDE-BASED CANCER IMAGING AGENTS

(71) Applicant: Ohio State Innovation Foundation, Columbus, OH (US)

(72) Inventors: Michael F. Tweedle, Bexley, OH (US); Shankaran Kothandaraman, Plain City, OH (US); Chadwick Lewis Wright, Lewis Center, OH (US); Li Gong, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 116 days.

(21) Appl. No.: 16/640,308

(22) PCT Filed: Aug. 20, 2018

(86) PCT No.: PCT/US2018/047085
§ 371 (c)(1),
(2) Date: Feb. 19, 2020

(87) PCT Pub. No.: WO2019/040367
PCT Pub. Date: Feb. 28, 2019

(65) Prior Publication Data
US 2020/0254116 A1 Aug. 13, 2020

Related U.S. Application Data

(60) Provisional application No. 62/547,821, filed on Aug. 19, 2017.

(51) Int. Cl.
| | | |
|---|---|---|
| *A61K 49/00* | (2006.01) | |
| *A61K 47/64* | (2017.01) | |
| *A61P 35/00* | (2006.01) | |
| *C07K 7/06* | (2006.01) | |
| *A61K 38/00* | (2006.01) | |

(52) U.S. Cl.
CPC .......... *A61K 49/0043* (2013.01); *A61K 47/64* (2017.08); *A61K 49/0032* (2013.01); *A61P 35/00* (2018.01); *C07K 7/06* (2013.01); *A61K 38/00* (2013.01)

(58) Field of Classification Search
CPC .......... A61K 47/64; A61K 49/00; A61P 35/00
See application file for complete search history.

(56) References Cited

FOREIGN PATENT DOCUMENTS

| WO | 02/02147 A2 | 1/2002 |
|---|---|---|
| WO | 2004/067779 A2 | 8/2004 |
| WO | 2006/076423 A2 | 7/2006 |
| WO | 2007/107326 A1 | 9/2007 |
| WO | 2013/151672 A2 | 10/2013 |

OTHER PUBLICATIONS

Antonello ZA & Nucera C 2014 Orthotopic mouse models for the preclinical and translational study of targeted therapies against metastatic human thyroid carcinoma with BRAF(V600E) or wild-type BRAF. *Oncogene* 33 5397-5404.
Bao L, Gorin MA, Zhang M, et al. (2009) Preclinical development of a bifunctional cancer cell homing, PKCepsilon inhibitory peptide for the treatment of head and neck cancer. Cancer Res 69:5829-5834.
Bihan H, Becker KL, Snider RH, Nylen E, Vittaz L, Lauret C, Modigliani E, Moretti JL & Cohen R 2003 Calcitonin precursor levels in human medullary thyroid carcinoma. *Thyroid* 13 819-822.
Cabanillas ME, Hu MI, Durand JB & Busaidy NL 2011 Challenges associated with tyrosine kinase inhibitor therapy for metastatic thyroid cancer. *J Thyroid Res* 2011 985780.
Chau NG & Haddad RI 2013 Vandetanib for the treatment of medullary thyroid cancer. *Clin Cancer Res* 19 524-529.
Cheung K, Wang TS, Farrokhyar F, Roman SA & Sosa JA 2012 A meta-analysis of preoperative localization techniques for patients with primary hyperparathyroidism. *Ann Surg Oncol* 19 577-583.
Fagin JA & Wells SAJ 2016 Biologic and Clinical Perspectives on Thyroid Cancer. *New England Journal of Medicine* 375 1054-1067.
Faustino-Rocha A, Oliveira PA, Pinho-Oliveira J, Teixeira-Guedes C, Soares-Maia R, da Costa RG, Colaço B, Pires MJ, Colaço J, Ferreira R, et al. 2013 Estimation of rat mammary tumor volume using caliper and ultrasonography measurements. *Lab Anim* (NY) 42 217-224.
Fischer AH, Jacobson KA, Rose J & Zeller R 2008 Hematoxylin and eosin staining of tissue and cell sections. *CSH Protoc* 2008 pdb prot4986.
Fogal V, Richardson AD, Karmali PP, Scheffler IE, Smith JW & Ruoslahti E 2010 Mitochondrial p32 protein is a critical regulator of tumor metabolism via maintenance of oxidative phosphorylation. *Mol Cell Biol* 30 1303-1318.
Fogal V, Zhang L, Krajewski S & Ruoslahti E 2008 Mitochondrial/cell-surface protein p32/gC1qR as a molecular target in tumor cells and tumor stroma. *Cancer Res* 68 7210-7218.
Gotthardt M, Lohmann B, Behr TM, Bauhofer A, Franzius C, Schipper ML, Wagner M, Höffken H, Sitter H, Rothmund M, et al. 2004 Clinical value of parathyroid scintigraphy with technetium-99m methoxyisobutylisonitrile: discrepancies in clinical data and a systematic metaanalysis of the literature. *World J Surg* 28 100-107.
Hong FD & Clayman GL 2000 Isolation of a peptide for targeted drug delivery into human head and neck solid tumors. *Cancer Res* 60 6551-6556.
Marshall MV, Draney D, Sevick-Muraca EM & Olive DM 2010 Single-dose intravenous toxicity study of IRDye 800CW in Sprague-Dawley rats. *Mol Imaging Biol* 12 583-594.
Morrison JA, Pike LA, Lund G, Zhou Q, Kessler BE, Bauerle KT, Sams SB, Haugen BR & Schweppe RE 2015 Characterization of thyroid cancer cell lines in murine orthotopic and intracardiac metastasis models. *Horm Cancer* 6 87-99.

(Continued)

*Primary Examiner* — Michael G. Hartley
*Assistant Examiner* — Jagadishwar R Samala
(74) *Attorney, Agent, or Firm* — Meunier Carlin & Curfman LLC

(57) ABSTRACT

Disclosed are compositions and methods relating to novel tumor targeting peptides.

25 Claims, 17 Drawing Sheets

Specification includes a Sequence Listing.

(56) References Cited

OTHER PUBLICATIONS

Nguyen QT, Olson ES, Aguilera TA, Jiang T, Scadeng M, Ellies LG & Tsien RY 2010 Surgery with molecular fluorescence imaging using activatable cell-penetrating peptides decreases residual cancer and improves survival. *Proc Natl Acad Sci U S A* 107 4317-4322.
Nucera C, Nehs MA, Mekel M, Zhang X, Hodin R, Lawler J, Nose V & Parangi S 2009 A novel orthotopic mouse model of human anaplastic thyroid carcinoma. *Thyroid* 19 1077-1084.
Ruoslahti E 2016 Tumor penetrating peptides for improved drug delivery. *Adv Drug Deliv Rev.* 3-12.
Schweppe RE, Klopper JP, Korch C, Pugazhenthi U, Benezra M, Knauf JA, Fagin JA, Marlow LA, Copland JA, Smallridge RC, et al. 2008 Deoxyribonucleic acid profiling analysis of 40 human thyroid cancer cell lines reveals cross-contamination resulting in cell line redundancy and misidentification. *J Clin Endocrinol Metab* 93 4331-4341.
Stummer W, Novotny A, Stepp H, Goetz C, Bise K & Reulen HJ 2000 Fluorescence-guided resection of glioblastoma multiforme by using 5-aminolevulinic acid-induced porphyrins: a prospective study in 52 consecutive patients. *J Neurosurg* 93 1003-1013.
Stummer W, Pichlmeier U, Meinel T, Wiestler OD, Zanella F & Reulen HJ 2006 Fluorescence-guided surgery with 5-aminolevulinic acid for resection of malignant glioma: a randomised controlled multicentre phase III trial. *Lancet Oncol* 7 392-401.
Tweedie MF 2009 Peptide-targeted diagnostics and radio therapeutics. *Acc Chem Res* 42 958-968.
Un F, Zhou B & Yen Y 2012 The utility of tumor-specifically internalizing peptides for targeted siRNA delivery into human solid tumors. *Anticancer Res* 32 4685-4690.
Vanden Borre P, Gunda V, McFadden DG, Sadow PM, Varmeh S, Bernasconi M & Parangi S 2014 Combined BRAF(V600E)- and SRC-inhibition induces apoptosis, evokes an immune response and reduces tumor growth in an immunocompetent orthotopic mouse model of anaplastic thyroid cancer. *Oncotarget* 5 3996-4010.
Verbeek HHG, Plukker JTM, Koopmans KP, de Groot JWB, Hofstra RMW, Muller Kobold AC, van der Horst-Schrivers ANA, Brouwers AH & Links TP 2012 Clinical Relevance of 18F-FDG PET and 18F-DOPA PET in Recurrent Medullary Thyroid Carcinoma. *Journal of Nuclear Medicine* 53 1863-1871.
Wells SA, Jr., Asa SL, Dralle H, Elisei R, Evans DB, Gagel RF, Lee N, Machens A, Moley JF, Pacini F, et al. 2015 Revised American Thyroid Association guidelines for the management of medullary thyroid carcinoma. *Thyroid* 25 567-610.
Yagi M, Uchiumi T, Takazaki S, Okuno B, Nomura M, Yoshida S, Kanki T & Kang D 2012 p32/gC1qR is indispensable for fetal development and mitochondrial translation: importance of its RNA-binding ability. Nucleic Acids Res 40 9717-9737.
International Preliminary Report on Patentability, issued for Application No. PCT/US2018/047085, dated Mar. 5, 2020.
International Search Report and Written Opinion issued by the International Searching Authority (ISA/US) in PCT Application No. PCT/US2018/047085 dated Dec. 26, 2018. 13 pages.
Communication pursuant to Rule 164(1) EPC, issued by the European Patent Office in European Application No. 18848597.3 dated May 3, 2021. 19 pages.
Dudas, Jozsef, et al. "Identification of HN-1-peptide target in head and neck squamous cell carcinoma cells." International Scholarly Research Notices. May 3, 2011, pp. 1-10.
Rosenthal, Eben L., et al. "Safety and tumor specificity of cetuximab-IRDye800 for surgical navigation in head and neck cancer." Clinical Cancer Research 21.16 (2015): 3658-3666.
Castelletto, Valeria, et al. "Self-assembly of Fmoc-tetrapeptides based on the RGDS cell adhesion motif." Soft Matter 7.24 (2011): 11405-11415.
Habibi, Neda, et al. "Self-assembled peptide-based nanostructures: Smart nanomaterials toward targeted drug delivery." Nano today 11.1 (2016): 41-60.
Ding, Haiming, et al. "Novel Peptide NIRF Optical Surgical Navigation Agents for HNSCC." Molecules 24.17 (2019): 3070.

Below: Structure of additional dyes conjugated at the lysine of HN-18 that are used to exemplify the inventions

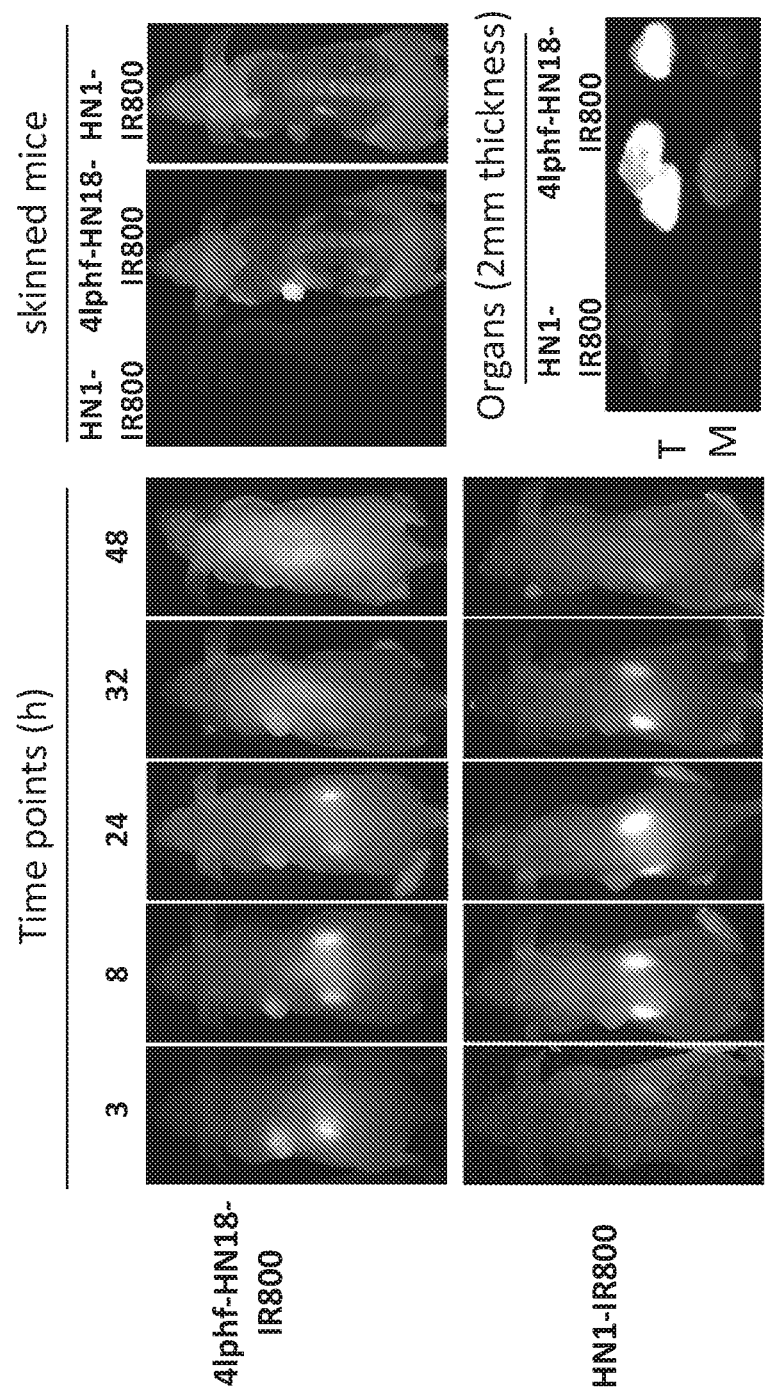

SEQUENCE LISTING

<160> NUMBER OF SEQ ID NOS: 9

<210> SEQ ID NO 1
<211> LENGTH: 12
<212> TYPE: PRT
<213> ORGANISM: Artificial Sequence
<220> FEATURE:
<223> OTHER INFORMATION: synthetic construct

<400> SEQUENCE: 1

Thr Leu Pro Asn Ser Asn His Ile Lys Gln Gly Leu

```
1               5               10

<210> SEQ ID NO 2
<211> LENGTH: 12
<212> TYPE: PRT
<213> ORGANISM: Artificial Sequence
<220> FEATURE:
<223> OTHER INFORMATION: synthetic construct

<400> SEQUENCE: 2

Thr Ser Pro Leu Asn Ile His Asn Gly Gln Lys Leu
1               5               10

<210> SEQ ID NO 3
<211> LENGTH: 12
<212> TYPE: PRT
<213> ORGANISM: Artificial Sequence
<220> FEATURE:
<223> OTHER INFORMATION: synthetic construct

<400> SEQUENCE: 3

Leu Asn Lys Gln Thr His Gly Leu Ile Pro Asn Ser
1               5               10

<210> SEQ ID NO 4
<211> LENGTH: 12
<212> TYPE: PRT
<213> ORGANISM: Artificial Sequence
<220> FEATURE:
<223> OTHER INFORMATION: synthetic construct

<400> SEQUENCE: 4

Asn Gln His Ser Lys Asn Thr Leu Leu Ile Gly Pro
1               5               10

<210> SEQ ID NO 5
<211> LENGTH: 11
<212> TYPE: PRT
<213> ORGANISM: Artificial Sequence
<220> FEATURE:
<223> OTHER INFORMATION: synthetic construct

<400> SEQUENCE: 5

Leu Lys Gln Gly Asn His Ile Asn Leu Pro Ser
1               5               10

<210> SEQ ID NO 6
<211> LENGTH: 12
<212> TYPE: PRT
<213> ORGANISM: Artificial Sequence
<220> FEATURE:
<223> OTHER INFORMATION: synthetic construct

<400> SEQUENCE: 6

Tyr Ser Pro Leu Asn Ile His Asn Gly Gln Lys Leu
1               5               10

<210> SEQ ID NO 7
<211> LENGTH: 11
<212> TYPE: PRT
<213> ORGANISM: Artificial Sequence
<220> FEATURE:
<223> OTHER INFORMATION: synthetic construct

<400> SEQUENCE: 7

Leu Pro Asn Ser Asn His Ile Lys Gln Gly Leu
1               5               10
```

```
<210> SEQ ID NO 8
<211> LENGTH: 12
<212> TYPE: PRT
<213> ORGANISM: Artificial Sequence
<220> FEATURE:
<223> OTHER INFORMATION: synthetic construct

<400> SEQUENCE: 8

Tyr Leu Pro Asn Ser Asn His Ile Lys Gln Gly Leu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: synthetic construct

<400> SEQUENCE: 9

Phe Leu Pro Asn Ser Asn His Ile Lys Gln Gly Leu
1               5                   10
```

PEPTIDE-BASED CANCER IMAGING AGENTS

II. CROSS REFERENCE TO RELATED APPLICATIONS

This application is national stage application filed under 35 U.S.C. 0371 of PCT/US2018/047085 filed Aug. 20,2018, which claims the benefit of U.S. Provisional Application No. 62/547,821, filed on Aug. 19, 2017, which is incorporated herein by reference in its entirety.

I. ACKNOWLEDGEMENT OF GOVERNMENT SUPPORT

This invention was made with government support under EB022134 awarded by the National Institutes of Health. The government has certain rights in the invention.

III. BACKGROUND

For head and neck squamous cell (HNSCC), breast, and other cancers including medullary thyroid cancers (MTC), external beam radiation is used for local control when surgery is no longer an option in some of the cancers. Traditional chemotherapies are often ineffective and inhibitors targeting kinases have had limited success because of high toxicities associated with these treatments.

Achieving optimal surgical outcomes requires removal of all target tissue and minimizing surgery time and risk to other tissues. To accomplish this, imaging prior to surgery is imperative. Current imaging modalities have made impressive progress, but each has limitations. Ultrasound (US), MRI and CT can be effectively used to identify primary tumors and used to determine gross lymph node involvement, although effectiveness can be subjective and based on user experience. For MTC, for example, metabolic imaging using $^{18}$F-Dopa-PET and $^{18}$F-FDG-PET only identify between 35-45% of progressive MTC lesions. Nuclear imaging using 99mTc sestamibi can be used but has poor sensitivity and lacks specificity due to uptake in a variety of tissues. FDG is generally specific only for high glucose metabolism and not cancer specific.

Complete removal of diseased tissue depends on a surgeon's ability to differentiate normal from diseased tissue. Intraoperative assessment is largely based on surgeon experience and pathological frozen sectioning analysis (FSA) of tissue that has been removed, typically lymph nodes and surgical margins. FSA is very time intensive as the surgeon waits for sample preparation, H&E staining and review by a pathologist. FSA also examines only a small fraction of the tissue removed. The other significant limitation of FSA is that it does not evaluate tissue left in situ (in the patient's body). The extent of tissue removed is based on the discretion of the surgeon. This limitation of pathologic tissue identification during surgery points to a need for better intraoperative methods of assessment. Intraoperative imaging has been successfully adapted in other cancer types. Fluorescence image guided surgery using near infrared fluorescent (NIRF) contrast agents has been shown to decrease residual tumor and improve survival in mouse models of melanoma and mammary adenocarcinomas. NMI agents are visible in real time by the surgeon as he operates. Tumor specific imaging agents may improve patient outcomes if these agents can increase the accurate surgical removal of all malignant tissue. Accordingly, what are needed are new NIRF imaging agents that can be more readily and abundantly absorbed into diseased cells and allow for better pathologic tissue identification.

IV. SUMMARY

The inventors describe herein the isolation of a chemically modified peptides (HN17 and HN18) that are specifically internalized by human head and neck squamous carcinoma (HNSCC) cells. In certain embodiments, the HN17 and/or HN18 peptide also is specific to solid tumor tissue cells, such as breast cancer and MTC, and other cancers. The inventors also describe methods which allow specific delivery of anticancer drugs including protein-based drugs such as antibodies and antibody fragments, affibodies, peptides, hormones, lipids, and carbohydrates conjugated with HN17 and/or HN18 (and derivatives thereof) to tumor tissue. In addition, the inventors describe methods for imaging and diagnosis of cancer cells by conjugating HN17 and/or HN18 with detectable labels and delivering the conjugate to patients or by contacting the conjugate with tumor tissue in vitro. The inventors furthermore provide methods to isolate an internalizing peptide for a tumor. In addition, the inventors further describe methods to detect a cancer cell by isolation of an internalizing peptide and conjugation to a drug or gene therapy composition for administration to a patient.

The HN17 and HIN18 peptides that the inventors have isolated differs from the peptide described in the Arap et al. (1998) study in that it is specific for the tumor cells rather than the tumor-associated endothelial cells. The present inventors envision conjugating any kind of anti-cancer drug to this peptide, to achieve a direct and specific killing of tumor cells. The natural ability of the peptide to enter tumor cells facilitates this process at the mechanistic level. prostate In an embodiment of the present disclosure there is a peptide that targets a tumor cell, wherein the peptide is internalized by the tumor cell. In a specific embodiment, the peptide comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9. In an additional embodiment the peptide consists of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9. In another embodiment of the present disclosure there is a DNA segment encoding SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9. In a specific embodiment the DNA segment comprises a nucleic acid that encodes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9. In an additional specific embodiment the DNA segment is further defined as a recombinant vector.

In another embodiment of the present disclosure there is provided a composition comprising a drug; and a peptide that targets a tumor cell, wherein the peptide is internalized by said tumor cell. In a specific embodiment, the peptide comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9. In a specific embodiment the peptide consists of SEQ ID NO: 1, SEQ ID NO: 2, SEQ ID NO: 3, SEQ ID NO: 4. SEQ ID NO: 5, SEQ ID NO: 6, SEQ ID NO: 7, SEQ ID NO: 8, or SEQ ID NO: 9. In a further specific embodiment the drug is a chemotherapeutic agent. In another specific embodiment, the drug is a cytotoxic agent. In an additional specific embodiment the drug is an apoptotic agent. In a further specific embodiment, the drug is a DNA-damaging agent. In another specific embodiment, the drug is doxorubicin, bleomycin, TAXOL® (or an analog thereof such as for example, docetaxel), methotrexate, or cetuximab. In an additional specific embodiment the drug is cisplatin (CDDP), carboplatin, procarbazine, mechlorethamine, cyclophosphamide, ifosfamide, melphalan, chlorambucil, bisulfan, nitrosurea, dactinomycin, daunorubicin, plicomycin, mitomycin, etoposide (VP16), tamoxifen, transplatinum, 5-fluorouracil, vincristin, or vinblastin or any other anti-cancer agent disclosed herein.

In accordance with an object of the present disclosure, there is provided a method for killing a tumor cell comprising contacting the tumor cell with a pharmaceutically acceptable composition comprising a drug; and a peptide that targets the tumor cell, wherein the peptide is internalized by the tumor cell. In a specific embodiment, the peptide comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9. In another specific embodiment the drug is conjugated to the peptide. In a further specific embodiment, the tumor cell is selected from the group consisting of squamous cell carcinomas, head and neck cancers, breast cancers, glioblastomas and astrocytomas. In a specific embodiment, the tumor cell is a human head and neck cancer cell. In a specific embodiment, the human head and neck cancer cell is an oral cavity cell, a pharynx cell, a throat cell, a paranasal sinus cell, a nasal cavity cell, a larynx cell, a thyroid cell, a parathyroid cell, a salivary gland cell, a skin cell of the face, a skin cell of the neck or a cervical lymph node cell. In another specific embodiment, the tumor cell is a solid tumor cell. In a further specific embodiment, the solid tumor cell comprises a breast cancer cell. In a specific embodiment, the contacting is by intravenous administration, intratumoral administration, subcutaneous administration, intra-arterial administration especially for prostate and liver cancer, intraperitoneal administration or topical administration. In an additional specific embodiment the contacting is by local, regional or systemic administration. In another specific embodiment, the tumor cell is in a patient.

In accordance with another aspect of the present disclosure there is provided a method for detecting cancer or cancer cell in a subject comprising obtaining a peptide comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9, wherein the peptide targets a tumor cell; conjugating a detectable label to the peptide; administering the conjugated peptide and label to a patient; and detecting binding of the conjugate to tumor cells by suitable detection means. In a specific embodiment, the binding further comprises uptake by said tumor cells. In another specific embodiment, the label is a radio- a fluorescent or a para- or superpara-magnetic label for MRI. In an additional specific embodiment the administering is by intravenous injection, intra-arterial injection, intratumoral injection, subcutaneous injection, intraperitoneal injection or topical administration. In a specific embodiment, the administering is by local, regional or systemic administering. In an additional embodiment the detection is by magnetic resonance imaging, optical imaging, or computerized emission tomography, in an additional embodiment, a dual probe is made by conjugation of any two different labels and detection is by both of the corresponding two detection techniques, such a optical imaging and positron emission tomography.

In accordance with other objects of the present disclosure there is provided a method for detecting a tumor in vitro comprising obtaining a peptide comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9, wherein said peptide targets the tumor; conjugating a detectable label to the peptide; contacting the conjugated peptide and label to the tumor-containing sample; and detecting binding of the conjugate to the tumor by suitable detection means. In a specific embodiment, the binding further comprises uptake by cells of the tumor. In a specific embodiment, the label is a radionucleotide, a fluorescent or a paramagnetic or superparamagnetic or fgerromagnetic (i.e. spin) label. In another embodiment, the detection is by nuclear magnetic resonance imaging, computerized emission tomography or positron emission tomography.

In accordance with another object of the present disclosure there is provided a tumor-detection kit comprising, in suitable container means, a pharmaceutical composition of a peptide comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9. In a further specific embodiment there is a tumor-detection kit comprising, in suitable container means, a pharmaceutical composition of a peptide comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9 bound to a detectable label, wherein said peptide targets a tumor cell. In another specific embodiment, there is a tumor-detection kit comprising, in suitable container means a pharmaceutical composition of a peptide comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9 bound to a detectable label, wherein the peptide targets a tumor cell; and a suitable means for detection. In a specific embodiment, the detectable label is detectable by non-invasive means, including external imaging and laporascopic imaging, and laporascopic fluorescence microscopy. In another specific embodiment, the detectable label is a spin-labeled molecule. In an additional specific embodiment the detectable label is a radioactive isotope. In an additional specific embodiment the detection means is by nuclear magnetic resonance imaging, computerized emission tomography, or positron emission tomography.

In accordance with another aspect of the present disclosure there is provided a tumor-imaging kit comprising, in a suitable container means, an effective amount of a pharmaceutically acceptable formulation comprising a peptide comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9, wherein said peptide targets a tumor cell. In a specific embodiment, the tumor-imaging kit comprises, in a suitable container means, an effective amount of a pharmaceutically acceptable formulation comprising a peptide comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9, wherein said peptide targets a tumor cell and wherein said peptide is bound to a detectable label. In a further specific embodiment, the tumor-imaging kit comprises, in suitable container means, an effective amount of a pharmaceutically acceptable formulation comprising a peptide comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9, wherein the peptide targets a tumor cell and wherein the peptide is further bound to a detectable label; and a suitable means for detecting said detectable label. In a specific embodiment, the detectable label is imaged by non-invasive means. In another specific embodiment, the detectable label is a MRI spin-labeled molecule. In a further specific embodiment, the detectable label is a radioactive isotope. In a specific embodiment, the detection means is by nuclear magnetic resonance imaging, optical imaging, computerized emission tomography or positron emission tomography.

In accordance with an object of the present disclosure there is a method for killing a tumor cell comprising administering to a patient radiotherapy; and a pharmaceutically acceptable composition comprising an anti-tumor compound conjugated to a peptide that targets said tumor cell, wherein said peptide is internalized by said tumor cell. In a specific embodiment, the peptide comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9. In an additional embodiment the radiotherapy is administered whole body, local, or regional. In an additional specific embodiment the radiotherapy is radioisotopic irradiation, γ-irradiation, X-ray irradiation, UV-irradiation, microwave irradiation or electronic irradiation. In a specific embodiment, the patient is administered about 40 to about 100 Gy radiation to the tumor. In another specific embodiment, the patient is administered about 55 to about 65 Gy radiation to the tumor. In an additional specific embodiment the patient is administered 62 Gy radiation to the tumor. In a specific embodiment, the tumor cell is selected from the group consisting of squamous cell carcinoma, head and neck cancer and breast cancer. In a further specific embodiment, the tumor cell is prostate cancer and the administration is to the prostate gland by intra-arterial injection to the prostatic artery.

In accordance with an object of the present disclosure there is provided a method for killing a tumor cell comprising administering to a patient chemotherapy; and a pharmaceutically acceptable composition comprising an anti-tumor compound conjugated to a peptide that targets said tumor cell, wherein said peptide is internalized by said tumor cell.

In accordance with an object of the present disclosure there is provided a method for killing a tumor cell comprising administering to a patient chemotherapy; and a pharmaceutically acceptable composition comprising a liposome or micelle linked to a peptide that targets said tumor cell, wherein said liposome or micelle comprises an anti-tumor compound, and wherein said peptide is internalized by said tumor cell.

In accordance with an object of the present disclosure there is provided a method for killing a tumor cell comprising administering to a patient chemotherapy; and a pharmaceutically acceptable composition comprising an antibody or antibody fragment linked to a peptide that targets said tumor cell, wherein said antibody or antibody fragment has anti-tumor activity, and wherein said peptide is internalized by said tumor cell. In one aspect, the peptide can maintain the antibody or antibody fragment in a particular tertiary conformation to maintain binding.

In accordance with another object of the present disclosure there is provided a method for killing a tumor cell comprising administering to a patient surgery; and a pharmaceutically acceptable composition comprising an anti-tumor compound conjugated to a peptide that targets said tumor cell, wherein said peptide is internalized by said tumor cell. In this embodiment, the internalizing peptide may be conjugated to both the anti-tumor compound and a fluorescent optical imaging agent.

In accordance with another object of the present disclosure there is a method for killing a tumor cell comprising administering to a patient gene therapy; and a pharmaceutically acceptable composition comprising an anti-tumor compound conjugated to a peptide that targets said tumor cell, wherein said peptide is internalized by said tumor cell. In a specific embodiment the gene therapy is directed to a nucleic acid sequence selected from the group consisting of ras; myc, raf, erb, src, fms, jun, trk, ret, gsp, hst, bcl abl, Rh, CFTR, p16, p21, p27, p53, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-2, IL-3, IL-4, IL-5, IL-6, IL-7, IL-8, IL-9, IL-10, IL-11 IL-12, GM-CSF G-CSF and thymidine kinase.

In accordance with an additional object of the present disclosure there is a tumor-treating kit in suitable container means comprising a therapeutically effective amount of a pharmaceutically acceptable formulation comprising a peptide comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9, wherein said peptide targets a tumor cell. In a specific embodiment, the tumor-treating kit in suitable container means comprises a therapeutically effective amount of a pharmaceutically acceptable formulation comprising a peptide comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9, wherein said peptide targets a tumor cell and an anti-tumor compound. In a specific embodiment, the anti-tumor compound is doxorubicin, bleomycin, TAXOL® (or an analog thereof such as for example, docetaxel), methotrexate, or cetuximab. In another specific embodiment, the anti-tumor compound is selected from the group consisting of cisplatin (CDDP), carboplatin, procarbazine, mechlorethamine, cyclophosphamide, ifosfamide, melphalan, chlorambucil, bisulfan, nitrosurea, dactinomycin, daunorubicin, plicomycin, mitomycin, etoposide (VP16), tamoxifen, transplatinum, 5-fluorouracil, vincristin, or vinblastin or any other chemotherapeutic agent disclosed herein.

In accordance with another object of the present disclosure there is a composition comprising a peptide comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9, wherein said peptide targets a tumor cell; and a vector comprising a composition for gene therapy. In a specific embodiment, the vector is selected from the group consisting of a protein, a peptide, a liposome, a lipid, a nucleic acid and a combination thereof. In a specific embodiment, the composition for gene therapy comprises a nucleic acid. In an additional specific embodiment the composition for gene therapy comprises a p53 nucleic acid. In a further specific embodiment the composition for gene therapy comprises a nucleic acid selected from the group consisting of ras, myc, raf, erb, src, fms, jun, trk, ret, gsp, hst, bcl abl, Rb, CFTR, p16, p21, p27, p53, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF G-CSF Ci-CSF and thymidine kinase.

In accordance with another object of the present disclosure there is provided a method to treat an organism for cancer comprising contacting said organism with a therapeutically effective amount of a pharmaceutically acceptable composition comprising a peptide comprising SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9, wherein said peptide targets a tumor cell; and an antitumor compound. In a specific embodiment, the antitumor compound is conjugated to said peptide. In another specific embodiment, the antitumor compound is TAXOL® (or an analog thereof such as for example, docetaxel), methotrexate, or cetuximab. In another specific embodiment, the anti-tumor compound is selected from the group consisting of cisplatin (CDDP), carboplatin, procarbazine, mechlorethamine, cyclophosphamide, ifosfamide, melphalan, chlorambucil, bisulfan, nitrosurea, dactinomycin, daunorubicin, plicomycin, mitomycin, etoposide (VP16), tamoxifen, transplatinum, 5-fluorouracil, vincristin, or vinblastin or any other chemotherapeutic agent disclosed herein. In a specific embodiment, the cancer is selected from the group consisting of squamous cell carcinoma, head and neck cancer and breast cancer.

In accordance with an additional object of the present disclosure there is provided a method for the isolation of an internalizing peptide (such as, for example, HN17, HN18, or any of the peptides listed in Tables 1 or 3) comprising the steps of obtaining a peptide library; individually contacting peptides of said library with members of a cell population; and assaying for endocytosis of said peptides by said members of said cell population. In a specific embodiment, the peptide library is a random peptide-display library. In a specific embodiment, the peptide library is a M13 single-stranded bacteriophage-based random peptide-display library. In a specific embodiment, the cell is a cancer cell.

In another embodiment of the present disclosure there is a method for detecting cancer comprising the steps of obtaining an internalizing peptide (such as, for example, HN17 (SEQ ID NO: 1) or HN18 SEQ ID NO: 7, or any of SEQ ID Nos: 2-6, 8, 9, or any of the peptides listed in Tables 1 or 3); conjugating a detectable label to said peptide; administering the conjugated peptide and label to an organism; and detecting binding of said conjugate to cancer cells by suitable detection means.

In an additional embodiment of the present disclosure there is a method for detecting cancer comprising the steps of obtaining a peptide library; individually contacting peptides of said library with members of a cell population; assaying for endocytosis of said peptides by said members of said cell population to identify an internalizing peptide (such as, for example, HN17 (SEQ ID NO: 1), HN18 (SEQ ID NO: 7) any of SEQ ID Nos: 2-6, 8, 9, or any of the peptides listed in Tables 1 or 3); conjugating a detectable label to said peptide; administering the conjugated peptide and label to an organism; and detecting binding of said conjugate to a cell by suitable detection means.

The inventors envision that this will allow one to provide the necessary dose of a drug to destroy tumors without being restricted by the occurrence of harmful side effects to other cells. The potential for HN17 and/or HN18 as a shuttle for drug delivery is further strengthened by the fact that it is nontoxic, nonimmunogenic, stable in vivo (shown by detecting intact peptide in blood 24 h after injection), protects its cargo during transit, and accumulates sufficiently in a tumor or tumors within 48 hours.

V. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows the full chemical structures of HN-1-FITC and 4Iphf-HN18-IR800 molecules. If also shows the structures of additional dye labels conjugated to HN17 in the identical way that IR800 is conjugated to HN18 making exactly analogous structures.

FIGS. 2A, 2B and 2C show the relative uptake of hybrid peptides in cultured Cal 27 cells (human HNSCC) measured by fluorescence of the respective dye labels in the cells. FIG. 2A. f-HN-1-IR800 (solid line) and HN1-IR800 (broken line) at 0.3, 1, 3, 10, 30 µM (48 h incubations with the cells); FIG. 2B. f-HN-1-IR800 (solid line) and HN1-IR800 (broken line) at 10 µM incubated for 0, 2, 4, 8, 24, 48 h; FIG. 2C. same experiment as 2B using FITC labeled peptides. The dye chemistry (FITC or IR800) has no significant effect on the relative rates of uptake by the two hybrid peptides.

FIG. 3 shows the relative cell uptake of IR800 labeled compounds in Cal 27 cells incubated for 2 h (see Table 3 for abbreviations). Cal 27 cells were incubated with indicated agents at 0.625-10 µM. Cell uptake is normalized to that f-HN-1-IR800 at 10 µM. The bottom most curve is the unconjugated IR800 dye as the free acid (commercially known as IRdye-800-CW).

FIG. 5A shows fluobeam optical images of intact whole mice bearing Cal 27 xenograft tumors from 3-48 h post intravenous administration of 40 nmol peptides.

FIG. 5B shows at the top whole-body images of skinned mice comparing HN1-IR800 and 4Iphf-HN18-IR800 (left two mice) at the fluorescence imager exposure of 75 ms, and HN1-IR800 (right) at exposure 300 ms. At the bottom FIG. 5B shows tumors and similar sizes of muscle that were sliced into 2 mm thick slabs and imaged all with the same exposure.

Figure 6:
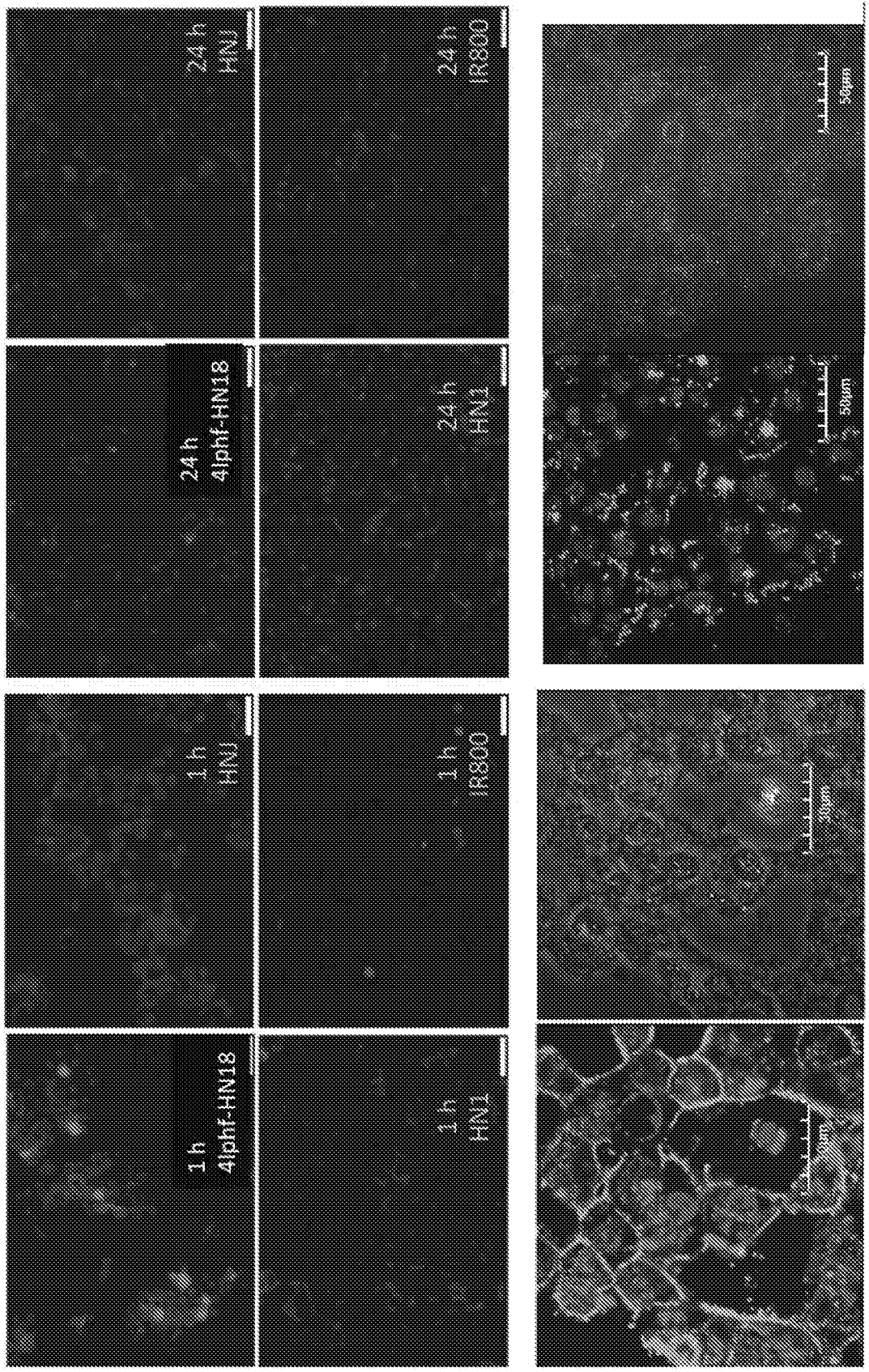

FIG. 6 shows (TOP two rows): Fluorescence microscopy of IR800-labeled compounds incubated with Cal 27 cells. 4Iph-HN18-IR800 shows bright red signal inside of the cells from 1 and 24 h incubations. HN-1-IR800, HNJ-IR800, and IR800 dye alone no conjugated to a peptide all show little to no fluorescence in cells. (Bottom Row): Confocal microscopy of living Cal27 cells treated with 10 uM 4Iphf-HN18-CY5(red.) for 1.5 h. Hoechst 33342 stains the cell nucleus (blue). F-actin in the cell cytoskeleton is stained orange by Alexa-546. see bottom most left cells in merged image). 4Iphf-HN18-Cy5 is seen as red. The white light photographic image at the bottom row right shows that cells are intact. The merged color image shows that the 4IphF-HN18-Cy5 is not in the nucleus or in the membrane, but has internalized into the cytosol of the cell. This is the most specific and desirable type of drug delivery, i.e. directly to the cytosol. In the bottom row, right two micrographs, the Cal 27 cells were treated with a 10 times molar excess of unlabeled 4Iphf-HN18 (100 µM) for 1.5 h before treating with 10 µM 4Iphf-HN18-Cy5. The excess unlabeled 4Iphf-HN18 stopped the internalization and so the 4Iphf-HN18-Cy5 is seen only surrounding the cells but not inside of the live cells, indicating that the mechanism is blockable and that the HN18 peptides work independently of the presence of a label.

Figure 7:
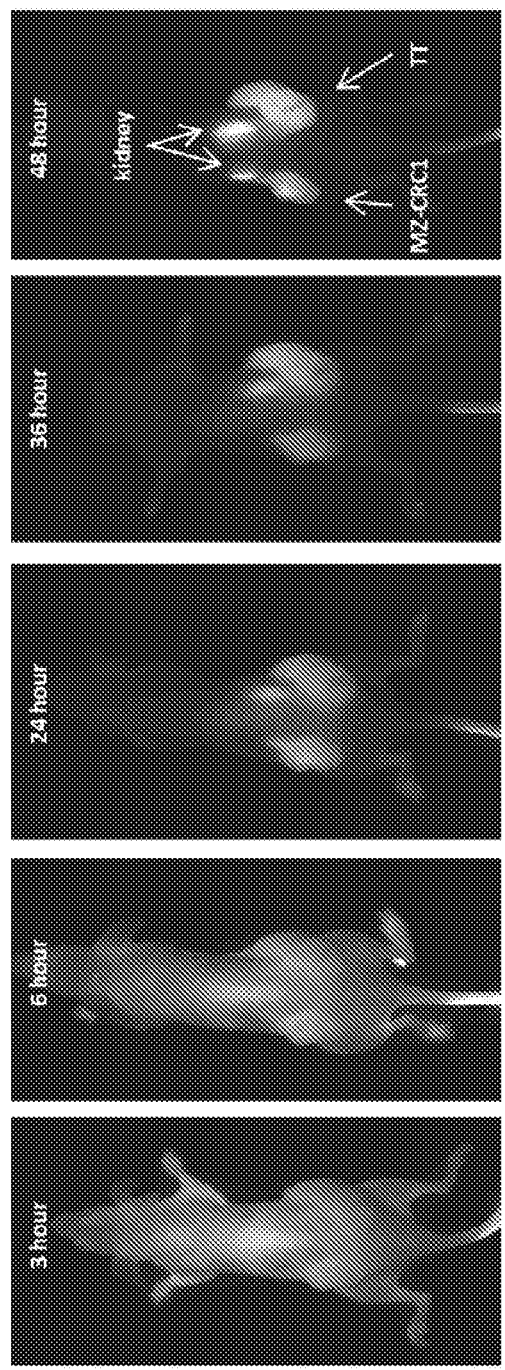

FIG. 7 shows fluorescence imaging of 4Iphf-HN18-IR8004Iph-HN18-IR800 in MTC flank subcutaneous xenograft models. Forty-eight hours after injection of 40 nmols intravenously mice were euthanized, and an image was taken after skin removal.

Figure 8:
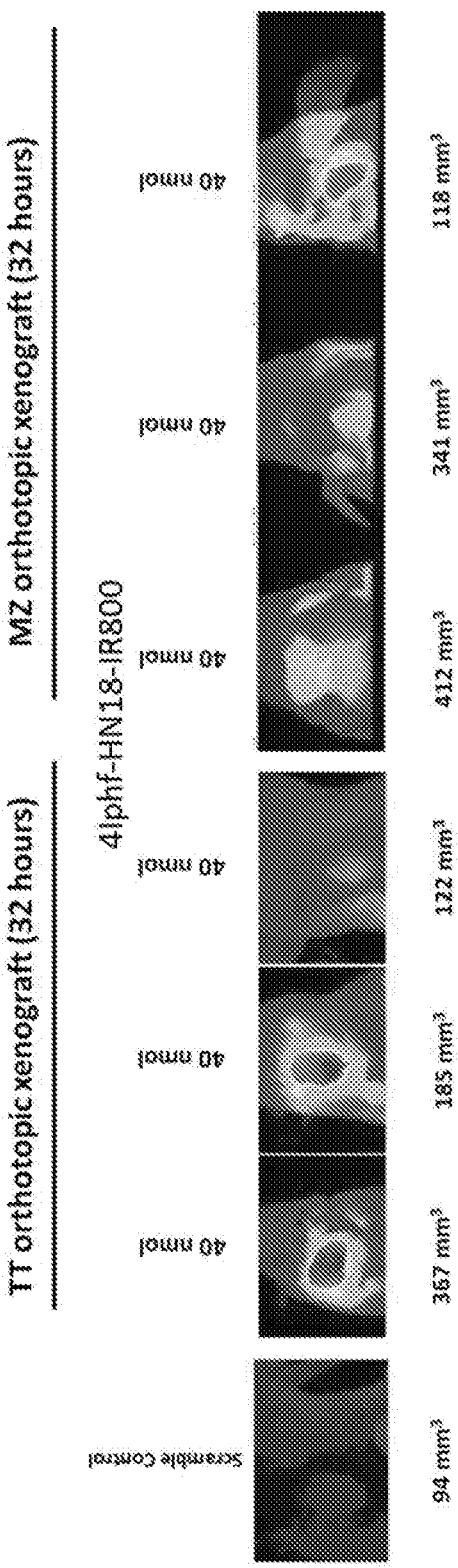

FIG. 8 shows the high fluorescence observed in TT and MZ-CRC1 (MTC cell) orthotopic xenografts where cells were implanted into the thyroid glands of the mice to grow into tumors. Forty nanomoles of HN-J-IR800 (left, scramble sequence jumbled control) or 4Iphf-HN18-IR800HN18 were injected by tail vein. Images where obtained after 32 hours, showing that 4Iphf-HN18-IR800HN18 allows imaging of orthotopic xenografts of MTC, whereas little to no fluorescence is observed in the peptide sequence scrambled control or in the surrounding tissues of 4Iphphf-HN18-IR800HN18injected mice.

Figure 9A:
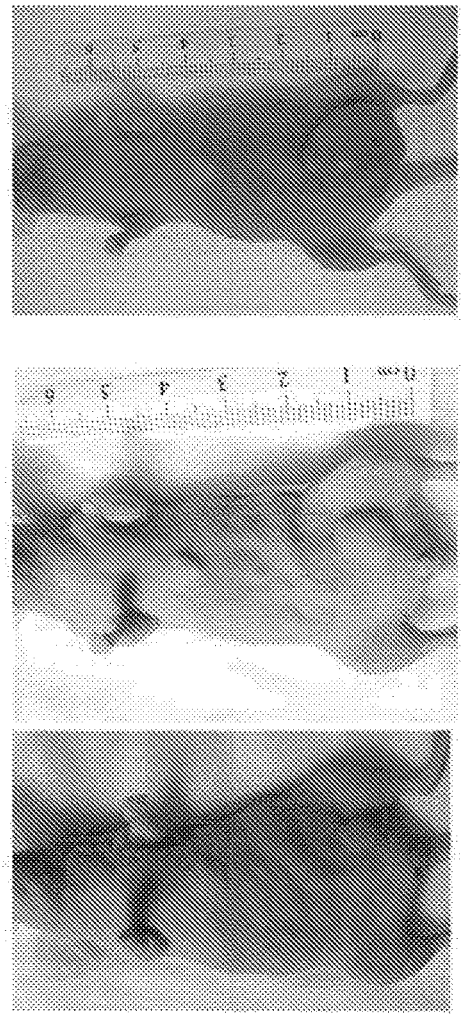

FIG. 9A shows MBA-MD-231 triple negative human breast cancer cells were implanted into two of the fat pads nude female mice. The growth rate of these tumors is shown in the FIG. 9 over time. In one of these mice with two such tumors, after the tumors grew to about 1 cm diameter, the mouse was injected with 40 nmol of f-f-HN17-IR800.

Figure 9B:
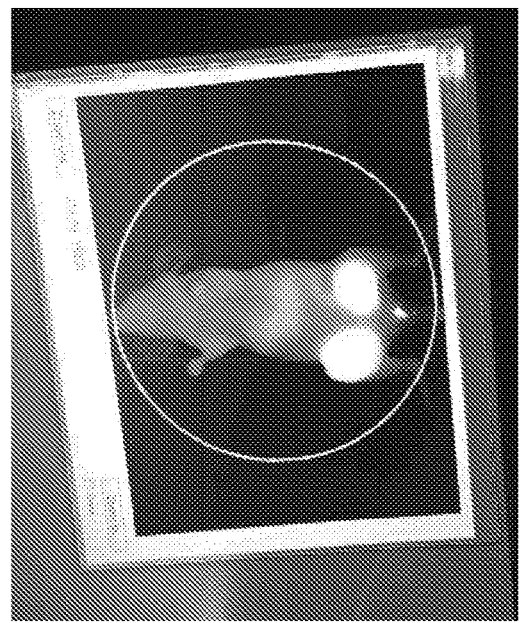

FIG. 9B shows recorded images were using a FluOptics Fluobeam optical surgical imager 24 hours following injection with 40 nmol of f-f-HN17-IR800 into a mouse with fat pad breast cancer tumors (MDA-MB-231). The large white ovals in the optical image are the two tumors demonstrating localization of the f-HN17-IR800 in the tumors.

Figure 10:
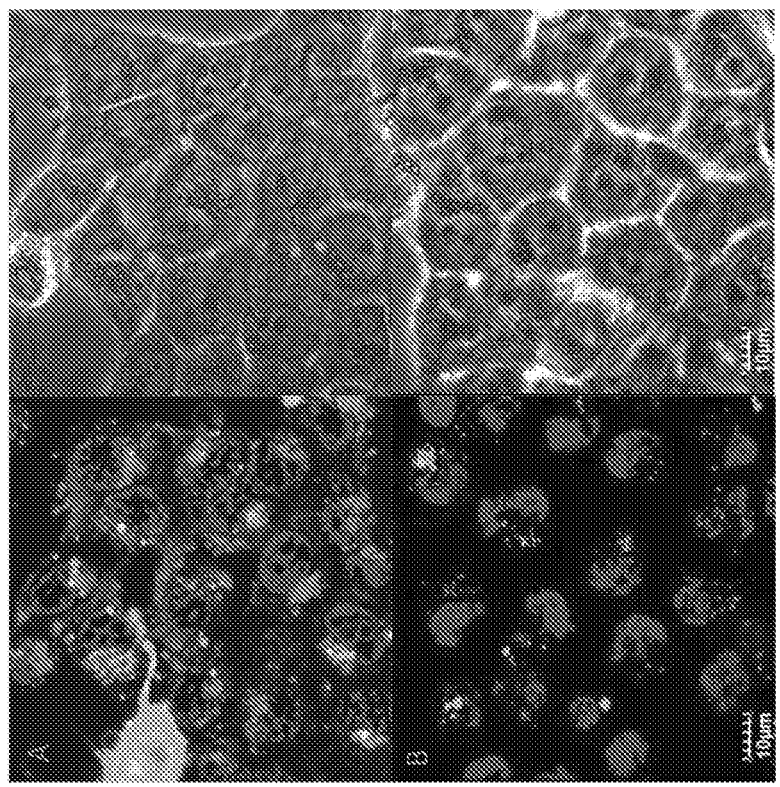

FIG. 10 shows confocal images of live unfixed Cal 27 cells at 37 degrees C. and 4 degrees C. White light images (right) show that the cells are intact. Hoechst 33342 stained the nuclei blue. Vybrant DiO stains part of the membrane green, and 4Iphf-HN18-Cy5 hybrid peptide is red. Removing most of the available environmental energy by lowering temperature slows down all processes including membrane binding and penetration by the peptide.

Figure 11:
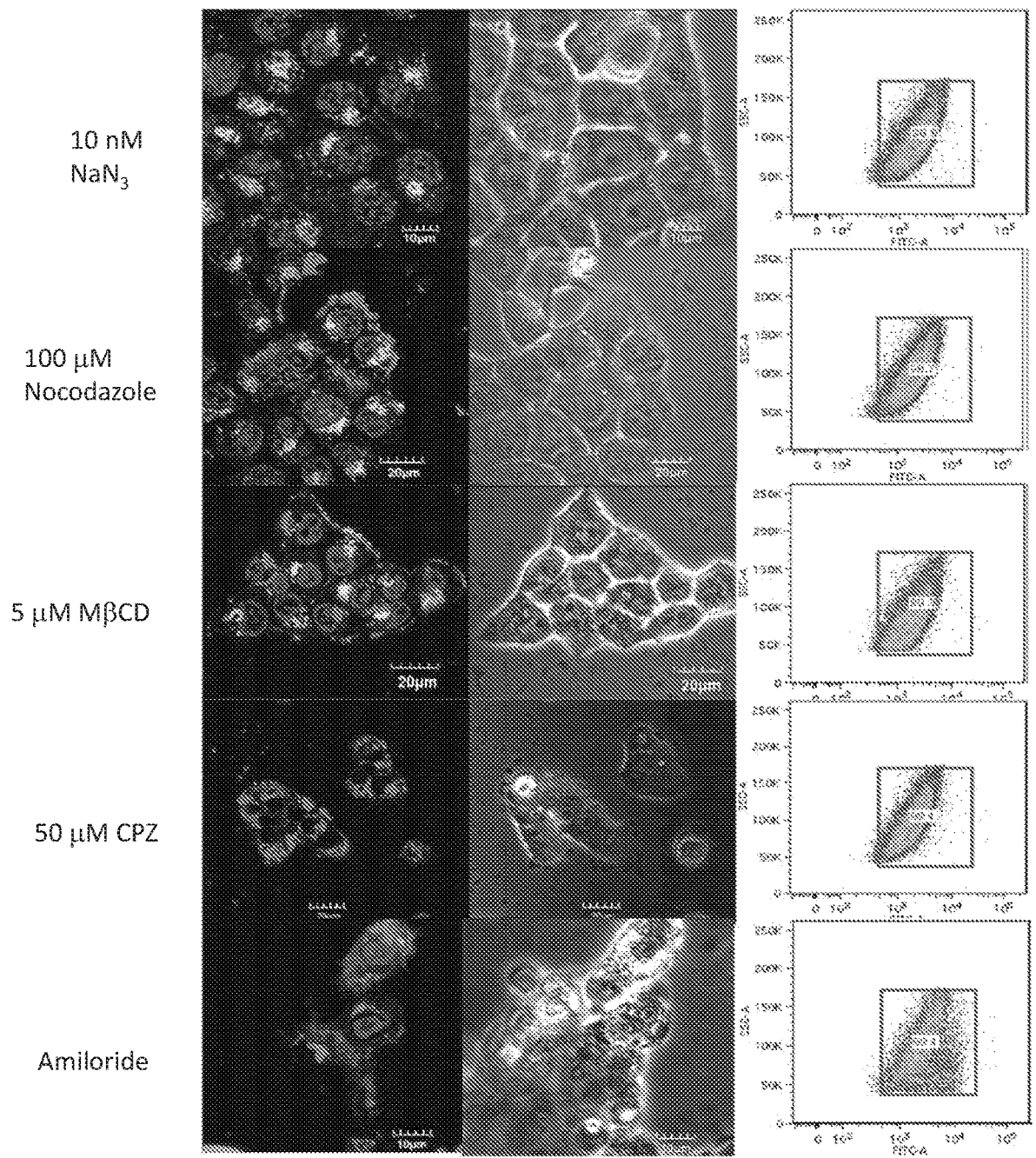

FIG. 11 shows confocal and FACS images of HN18 peptide penetration in the presence of various endocytotosis inhibitors. In FIG. 11 the middle column white light images show that the live, unfixed Cal 27 cells in the left column images are intact. The FACS data in the right column using 4Iphf-HN18-FITC incubated 1 h at 10 uM with the cells demonstrates that most of the cells are labeled with the fluorescent labeled hybrid peptide. The left column shows that in each condition measured, 4Iphf-HN18-Cy5 (red) penetrated the cell membranes to reside in the cytosol. Blue stained nuclei are stained with Hoechst 33342. Green is Vybrant DiO staining some of the membrane. NaN3 depletes ATP showing that the hybrid peptide penetrates the cell membrane to the cytosol without using cellular energy dependent processes. Nocodazole inhibits formation of Clathrin-coated pits, showing that the hybrid peptides does not use this mechanism for penetrating to the cytosol of the cells. MβCD inhibits the lipid raft-mediated caveolae pathway showing that the hybrid peptide does not use this mechanism for cell penetration. CPZ is chlorpromazine that inhibits the clathrin independent pathway showing that the hybrid peptide does not use this mechanism to penentrate the cell to the cytosol (nuclei were not stained and are black). Finally amiloride inhibits macropinocytosis showing that the hybrid peptide does not use this mechanism to penetrate the cell to the cytosol.

Figure 12A:
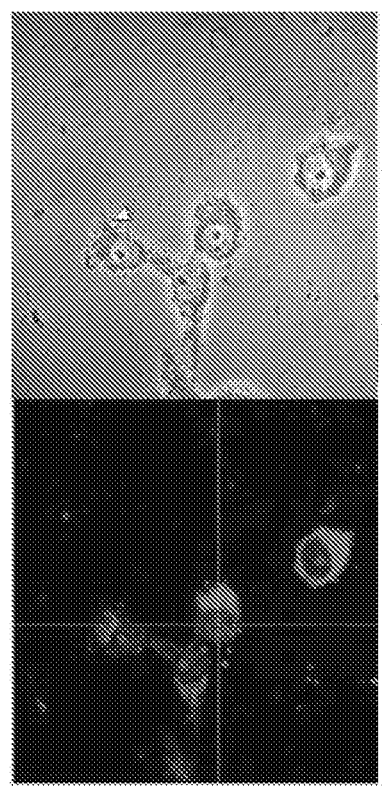

FIG. 12A shows live, unfixed Cal 27 cells incubated with 5 uM 4Iphf-HN18-Cy5 for 1 h. The red in the left images is 41phf-HN18-Cy5. The blue in this image is propidium iodide, a molecule that cannot penetrate intact cell membranes. When incubated simultaneously with 41phf-HN18-Cy5, however, the propidium iodide does penetrate the Cal 27 cell membrane to cytosol and moves to the nucleus to stain it blue.

Figure 12B:
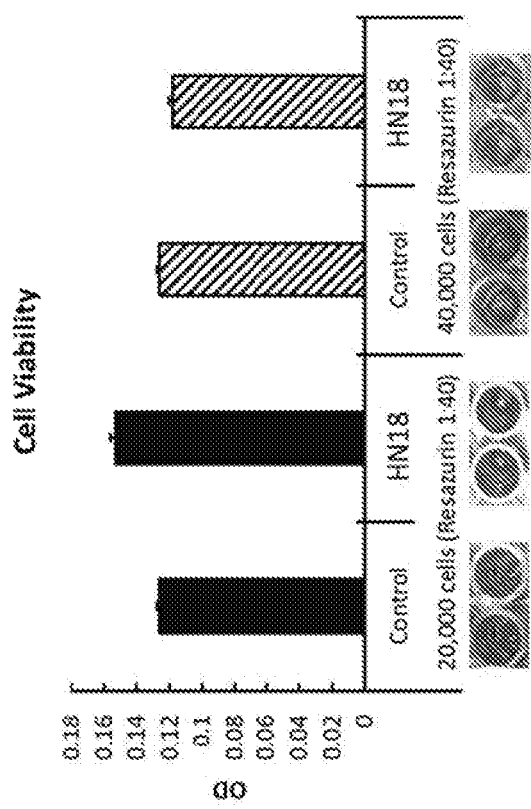

FIG. 12B demonstrates that the cells remain viable in the presence of ≥41phf-HN18-Cy5 Resazurin is used. 41phf-HN18-Cy5 does not affect cell viability, so the propidium iodide in FIG. 12A is allowed into the cell in the presence of 41phf-HN18-Cy5 in a benign, directly penetrating mechanism, analogous to what drug would do in the same situation.

Figure 13:
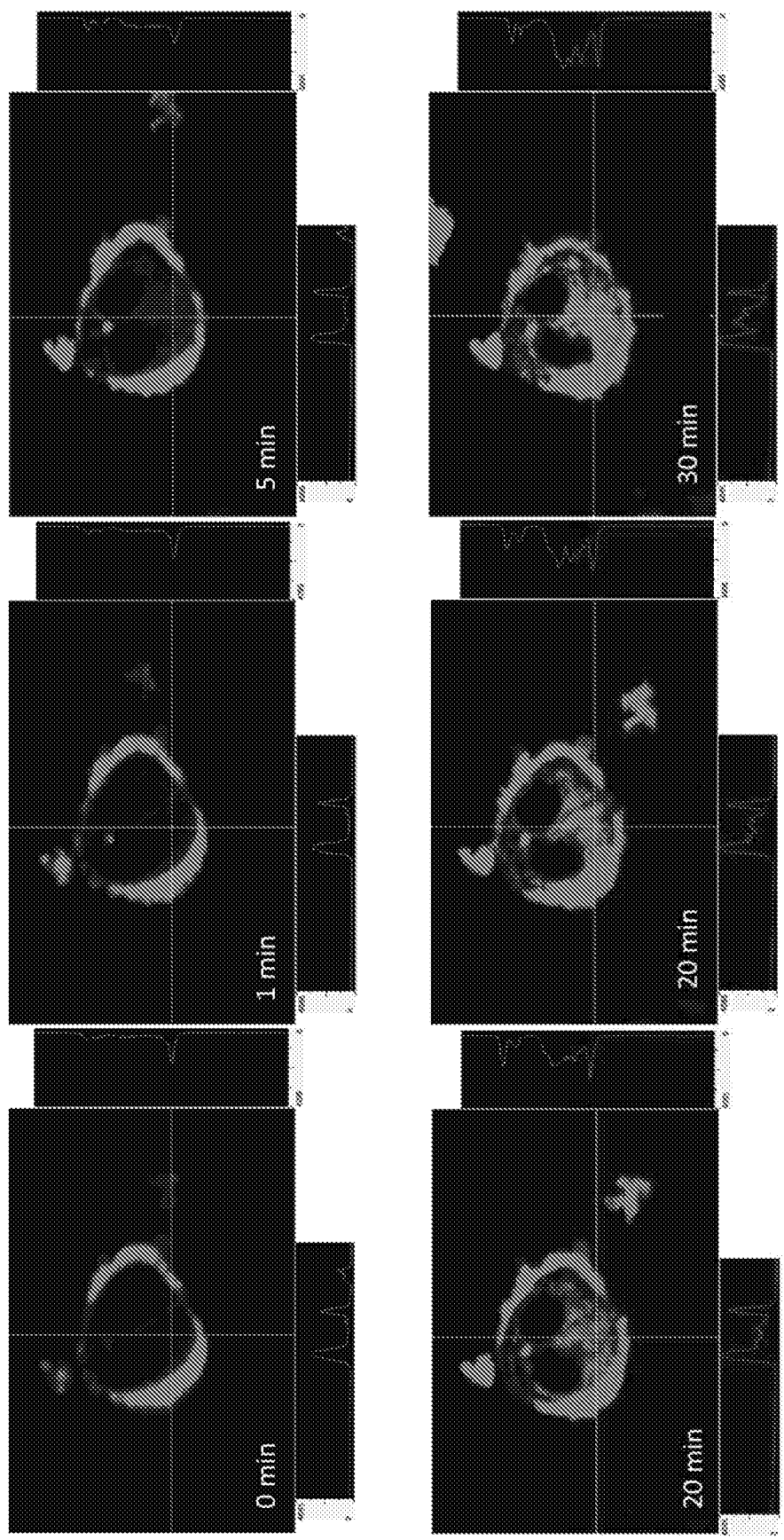

FIG. 13 shows the kinetics of cell penetration by 4Iphf-HN18-Cy5 in Cal 27 live unfixed cells. Two cells are shown. The 4Iphf-HN18-Cy5 penetrates from bulk solution to the cell membrane in seconds, then penetrates into the cytosol visibly within 5 minutes, continuing to move into the cell over the next 25 minutes.

VI. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are several values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The term "apoptotic agent" as used herein is defined as a drug, toxin, compound, composition or biological entity which bestows apoptosis, or programmed cell death, onto a cell. In a specific embodiment, the cell is a tumor cell. In another embodiment, the tumor cell is a head and neck cancer cell, a squamous cell carcinoma, a brain tumor cell or a breast cancer cell. The term "cancer" as used herein is defined as a tissue of uncontrolled growth or proliferation of cells, such as a tumor. In a specific embodiment, the tumor leads to local invasion and metastasis.

The term "chemotherapeutic agent" as used herein is defined as a drug, toxin, compound, composition or biological entity which is used as treatment for cancer.

The term "conjugate" as used herein is defined as the tethering or binding of a HN17 or HN18 peptide with another entity, such as a drug, composition, compound, or detectable label. The conjugation is executed in a specific embodiment by a chemical reaction associated with, for example, a carboxylate group or amine group of the HN17 or HN18 peptide and an activated group on the corresponding drug. A skilled artisan is aware that the chemical reaction would depend on what functional groups were present on HN17 or HN18 or its derivatives and what corresponding functional groups were present on the drug.

The term "cytotoxic agent" as used herein is defined as a drug, toxin, compound, composition or biological entity which is used to kill a cell or cells. In a specific embodiment, the cell is a tumor cell. In another embodiment, the tumor cell is a head and neck cancer cell, a squamous cell carcinoma, or a breast cancer cell.

The term "delivery" as used herein is defined as the molecular conveyance provided by a peptide or fragment of HN17 and/or HN18 for a compound to which it is bound or conjugated to a tumor or tumor cell. The targeting may be directly to the tumor or tumor cell upon administration or may be by indirect means or mechanisms. It is within the scope of the term to permit the conjugate comprising the HN17 and/or HN18 compound to follow an indirect path for eventually targeting the tumor or tumor cell, including binding for non-therapeutic purposes to other biological entities. The term "delivery" as used herein may be used interchangeably with the term "targeting."

The term "DNA-damaging agent" as used herein is a drug, toxin, compound, composition or biological entity which damages nucleic acid. The damage may be of any kind to the nucleic acid, for example, to break one or both strands of a DNA double helix molecule or to cause mutation of one or more nucleotides.

The term "drug" as used herein is defined as a medicament medicine which is used for the therapeutic treatment of a medical condition or disease. The drug may be used in combination with another drug or type of therapy and in a preferred embodiment is effective for the treatment of cancer.

The term "head and neck cancer" as used herein is defined as any of a variety of malignant tumors that may occur in the head and neck region: the oral cavity (including the tissues of the lip or mouth such as the tongue, the gums, the lining of the cheeks and lips, the bottom of the mouth, the hard and soft palate and the retromolar trigone); the pharynx (including the hypopharynx, nasopharynx and oropharynx) (also called the throat); paranasal sinuses (including the frontal sinuses above the nose, the maxillary sinuses in the upper part of either side of the upper jawbone, the ethmoid sinuses just behind either side of the upper nose, and the sphenoid sinus behind the ethmoid sinus in the center of the skull) and nasal cavity; the larynx (or voicebox); thyroid gland (including cancers of the thyroid which are papillary, follicular, medullary and anaplastic); parathyroid gland; salivary glands (including the major clusters of salivary glands found below the tongue, on the sides of the face just in front of the ears, and under the jawbone); lesions of the skin of the face and neck and the cervical lymph nodes; and metastatic squamous neck cancer with occult primary.

The term "internalizing" as used herein is defined as the uptake of at least part of the HN17 and/or HN18 peptide or another peptide isolated by similar means as described herein into a tumor or into a tumor cell. Internalizing into a tumor cell means a part or all of a peptide such as HN17 and/or HN18 is taken into the cell's interior region, which includes retention of part or all of the peptide in or into the membrane of the cell, and also includes part or all of the peptide in the cell's cytoplasm. The internalizing may be transient or permanent.

The term "label" as used herein is defined as an entity bound or conjugated, either directly or indirectly, to a HN17 and/or HN18 peptide which allows for detection of the peptide. The label may be a fluorophore, a chromophore, a radioactive label, a spin label or any other means to facilitate detection of the peptide.

The term "oral cancer" as used herein is defined as cancer of the oral cavity.

The term "oral cavity" as used herein is defined as any of the tissues of the lip or mouth such as the tongue, the gums, the lining of the cheeks and lips, the bottom of the mouth, the hard and soft palate and the retromolar trigone (the region behind the wisdom teeth).

The term "peptide" as used herein is defined as a chain of up to about 50 amino acids.

The term "specific," as used herein, is defined in one embodiment as delivery or targeting by an HN17 and/or HN18 peptide or another internalizing peptide conjugated to an antitumor compound to cancerous tissue. In a another embodiment, the term specific means an HN17 and/or HN18 peptide or another internalizing peptide delivers or targets an antitumor compound preferentially to cancerous tissue. In a yet another embodiment, the term refers to delivery or targeting of cancerous tissue for an antitumor compound in which a conjugate comprising an HN17 and/or HN18 peptide or another internalizing peptide binds predominantly nothing else but the cancerous tissue. In one aspect of these embodiments, the conjugate described herein may contact other biological entities during the process or journey of delivery of the conjugate to a tumor.

The term "targets" as used herein is defined as the molecular direction provided by a HN17 and/or HN18 peptide or fragment thereof for a compound to which it is bound or conjugated to a tumor or tumor cell. The targeting may be directly to the tumor or tumor cell upon administration or may be by indirect means or mechanisms. It is within the scope of the term to permit the conjugate comprising the HN17 and/or HN18/compound to follow an indirect path for eventually targeting the tumor or tumor cell, including binding for non-therapeutic purposes to other biological entities.

The term "to treat" as used herein is defined as the practice of applying a treatment for a medical condition or disease. The treatment need not provide a complete cure and is considered effective if at least one symptom is improved upon or eradicated. Furthermore, the treatment need not provide a permanent improvement of the disease state or medical condition, although this is preferable.

The term "tumor cell" as used herein is defined as a cell of a malignant mass, such as a tumor or cancer. The cell may be located within the tumor, on the surface of the tumor, or it may be associated with the tumor.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. COMPOSITIONS

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular HN17 and/or HN18 is disclosed and discussed and a number of modifications that can be made to a number of molecules including the HN17 and/or HN18 are discussed, specifically contemplated is each and every combination and permutation of HN17 and/or HN18 and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

In one aspect, the present disclosure is directed toward utilization of an amino acid TLPNSNHIKQGL (HN17) (SEQ ID NO: 1), TSPLNIHNGQKL (HN1) (SEQ ID NO: 2), LNKQTHGLIPNS (HNscr) (SEQ ID NO: 3), NQHSKNTLLIGP (HNJ) (SEQ ID NO: 4), LKQGNHINLPS (SEQ ID NO: 5), YSPLNIHNGQKL (SEQ ID NO: 6), LPNSNHIKQGL (HN18) (SEQ ID NO: 7), YLPNSNHIKQGL (SEQ ID NO: 8), or FLPNSNHIKQGL (SEQ ID NO: 9) conjugated to a compound for delivery of the conjugated complex to a tumor. The ability of this peptide permits targeting anti-cancer drugs to tumors, such as head and neck squamous carcinomas and breast cancer. In other specific embodiments, the peptides facilitate imaging and diagnosis of cancer cells through conjugation to detectable labels and subsequent delivery to tumor tissue in a patient.

In some embodiments, the HN17 peptides, variants, and synthetic molecules can be defined by Formula (I)

$$X_R\text{—}Z\text{—}K_{R1}\text{-}L_{R2} \qquad (I),$$

wherein

X is T, Y, Fluorenylmethyloxycarbonyl (Fmoc), abbreviated as (f), 4-para-iodo-benzyl (4Iph), or 3-iodotyrosine (3IY). X can be any terminating residue. For example, X can be a chemical moiety resulting from the cleavage of the biocompatible self-assembling molecule from a solid support resin used during solid phase peptide synthesis. For example, X can be an amine, an alcohol, an amide group, or a carboxylic acid group (e.g., the $NH_2$ or COOH group of a C-terminal or N-terminal amino acid). Alternatively, the terminating residue X can be a propionic amide or propionic acid group. X can also be a chemically modified form of such a moiety (e.g., an alkylated amine or an esterified carboxylic acid). In any embodiment, specifically disclosed or variant contemplated herein and encompassed by the disclosure herein, X is lipophilic.

Z represents an amino acid sequence for HN17—TLPNSNHIKQGL (SEQ ID NO: 1), HN1—TSPLNIHNGQKL (SEQ ID NO: 2), HNscr—LNKQTHGLIPNS (SEQ ID NO: 3), HNJ—NQHSKNTLLIGP (SEQ ID NO: 4), LKQGNHINLPS (SEQ ID NO: 5), YSPLNIHNGQKL (SEQ ID NO: 6), HN18—LPNSNHIKQGL (SEQ ID NO: 7), YLPNSNHIKQGL (SEQ ID NO: 8), or FLPNSNHIKQGL (SEQ ID NO: 9);

R represents a terminal amino group as $NR_3R_4$ and must be lipophilic (such as, for example 4Iph and Fmoc). In one aspect, lipophile can be an amphiphile such as IR800.

R1 represents near infrared fluorescent (NIRF) dyes (e.g., Fluorescein (FITC) or water soluble dicyanine dyes) or R2. In one aspect, R1 can be a IRDye800 (IR800); or H R2 represents terminal $CONR_5R_6$;

R3, R4, R5, and R6 represent H, COalkyl (linear or cyclic) or $COQR_7$;

R7 represents H, COalkyl (linear or cyclic);

Q represents O or $NHR_8$; and $R_8$ represents H, COalkyl (linear or cyclic), or $COXR_7$.

R must be a lipophile, such as, for example a non-active lipophile, a lipophilic therapeutic drug (e.g., Taxol), or a lipophilic optical dye such as a dicyanine lacking one or more $COO^-$ or $SO^{3-}$ groups. R1 and R2 are hydrophilic, either H or FITC, or a multiply charged optical dye for diagnostics (such as, for example, optical surgical navigation or tissue staining in histology)m or a hydrophilic therapeutic drug such as another peptide, PKCε or a siRNA. R1 an dR2 can be different or the same.

The amino acids are classified into Table 1.

TABLE 1

Agent number and its amino acid sequence

| Compound No. | Peptide Sequence[1] (SEQ ID NO:) | Molecular Formula | Molecular Weight (calculated) | Molecular Weight (found)[2] |
|---|---|---|---|---|
| 1 | $T_R$SPLNIHNGQKL | $C_{72}H_{107}N_{19}O_{19}$ | 1542.74 | 1542.83 |

TABLE 1-continued

Agent number and its amino acid sequence

| Compound No. | Peptide Sequence[1] (SEQ ID NO:) | Molecular Formula | Molecular Weight (calculated) | Molecular Weight (found)[2] |
|---|---|---|---|---|
| 2 | $T_R$SPLNIHNGQK$_{R1}$L | $C_{93}H_{118}N_{20}O_{24}S$ | 1930.83 | 1931.74 |
| 3 | TSPLNIHNGQK$_{R1}$L | $C_{78}H_{108}N_{20}O_{22}S$ | 1709.88 | 1709.84 |
| 4 | $T_{R1}$SPLNIHNGQK$_{R1}$L | $C_{99}H_{119}N_{21}O_{27}S_2$ | 2099.26 | 2098.95 |
| 5 | $T_R$SPLNIHNGQK$_{R2}$L | $C_{118}H_{160}N_{21}O_{33}S_4$ | 2527.04 | 2527.06 |
| 6 | TSPLNIHNGQK$_{R2}$L | $C_{103}H_{150}N_{21}O_{31}S_4$ | 2304.97 | 2304.83 |
| 7 | TLPNSNHIKQGL (SEQ ID NO: 1) | | | |
| 8 | $T_R$LPNSNHIKQGL | $C_{72}H_{107}N_{19}O_{19}$ | 1542.74 | 1542.79 |
| 9 | $T_R$LPNSNHIK$_{R2}$QGL | $C_{118}H_{160}N_{21}O_{33}S_4$ | 2527.04 | 2527.26 |
| 10 | $T_{R3}$LPNSNHIKQGL | $C_{64}H_{100}IN_{19}O_{18}$ | 1550.52 | 1550.75 |
| 11 | $T_{R3}$LPNSNHIK$_{R2}$QGL | $C_{110}H_{153}IN_{21}O_{32}S_4$ | 2534.89 | 2534.98 |
| 12 | $L_R$KQGNHINLPS | $C_{72}H_{107}N_{19}O_{19}$ | 1542.74 | 1542.81 |
| 13 | $L_R$K$_{R2}$QGNHINLPS | $C_{118}H_{160}N_{21}O_{33}S_4$ | 2527.04 | 2527.13 |
| 14 | $N_R$QHSKNTLLIGP | $C_{72}H_{107}N_{19}O_{19}$ | 1542.74 | 1542.85 |
| 15 | $N_R$QHSK$_{R2}$NTLLIGP | $C_{118}H_{160}N_{21}O_{33}S_4$ | 2527.04 | 2527.21 |
| 16 | NQHSK$_{R2}$NTLLIGP | $C_{103}H_{150}N_{21}O_{31}S_4$ | 2304.97 | 2305.05 |
| 17 | $Y_R$SPLNIHNGQKL | $C_{77}H_{109}N_{19}O_{19}$ | 1604.83 | 1604.87 |
| 18 | $Y_R$SPLNIHNGQK$_{R2}$L | $C_{123}H_{162}N_{21}O_{33}S_4$ | 2589.05 | 2589.28 |
| 19 | $Y_R$LPNSNHIKQGL | $C_{77}H_{109}N_{19}O_{19}$ | 1604.83 | 1604.79 |
| 20 | $Y_R$LPNSNIHIK$_{R2}$QGL | $C_{123}H_{162}N_{21}O_{33}S_4$ | 2589.05 | 2589.49 |
| 21 | (4-I) $F_R$LPNSNHIKQGL | $C_{77}H_{108}IN_{19}O_{18}$ | 1714.73 | 1714.57 |
| 22 | (4-I) FLPNSNHIK$_R$QGL | $C_{77}H_{108}IN_{19}O_{18}$ | 1714.73 | 1714.67 |
| 23 | (4-I) $F_R$LPNSNHIK$_{R2}$QGL | $C_{123}H_{161}IN_{23}O_{32}S_4$ | 2698.95 | 2699.15 |
| 24 | (4-I) $F_{R2}$LPNSNHIK$_R$QGL | $C_{123}H_{161}IN_{23}O_{19}$ | 2698.95 | — |
| 25 | (4-I) $F_R$LPNSNHIK$_{R3}$QGL | $C_{109}H_{145}IN_{21}O_{33}S_4$ | 2179.01 | 2178.96 |
| 26 | (3-1) $Y_R$LPNSNHIKQGL | $C_{77}H_{108}IN_{19}O_{19}$ | 1730.73 | 1730.78 |
| 27 | (3-1) $Y_R$LPNSNHIK$_{R2}$QGL | $C_{123}H_{161}IN_{23}O_{33}S_4$ | 2716.90 | — |

$R_n$ can be an alkyl, alkenyl, or alkynyl group. "Alkyl," as used herein, refers to the radical of a saturated aliphatic group, including straight-chain alkyl and branched-chain alkyl groups. In some embodiments, the alkyl group comprises 30 or fewer carbon atoms in its backbone (e.g., $C_1$-$C_{30}$ for straight chain, $C_3$-$C_{30}$ for branched chain). For example, the alkyl group can comprise 25 or fewer carbon atoms, 22 or fewer carbon atoms, 20 or fewer carbon atoms, 19 or fewer carbon atoms, 18 or fewer carbon atoms, 17 or fewer carbon atoms, 16 or fewer carbon atoms, 15 or fewer carbon atoms, 14 or fewer carbon atoms, 12 or fewer carbon atoms, 12 or fewer carbon atoms, 10 or fewer carbon atoms, 8 or fewer carbon atoms, or 6 or fewer carbon atoms in its backbone. In some embodiments, the alkyl group can comprise 6 or more carbon atoms, 8 or more carbon atoms, 10 or more carbon atoms, 11 or more carbon atoms, 12 or more carbon atoms, 13 or more carbon atoms, 14 or more carbon atoms, 15 or more carbon atoms, 16 or more carbon atoms, 17 or more carbon atoms, 18 or more carbon atoms, 19 or more carbon atoms, or 20 or more carbon atoms in its backbone. The alkyl group can range in size from any of the minimum number of carbon atoms to any of the maximum number of carbon atoms described above. For example, the alkyl group can be a $C_6$-$C_{30}$ alkyl group (e.g., a $C_{12}$-$C_{22}$ alkyl group, or a $C_{12}$-$C_{18}$ alkyl group). The term alkyl includes both unsubstituted alkyls and substituted alkyls, the latter of which refers to alkyl groups having one or more substituents, such as a halogen or a hydroxy group, replacing a hydrogen on one or more carbons of the hydrocarbon backbone. The alkyl groups can also comprise between one and four heteroatoms (e.g., oxygen, nitrogen, sulfur, and combinations thereof) within the carbon backbone of the alkyl group. "Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

In certain embodiments, $R_n$ is straight-chain $C_{12}$-$C_{18}$ alkyl group (e.g., a straight-chain $C_{14}$-$C_{16}$ alkyl group). For example, $R_n$ can be a lauryl group, a myristyl group, a palmityl group, or a stearyl group.

In certain embodiments $R_n$ is cyclic.

Each of the integers (q, o, p, and n, where is an integer representing the number of carbon atoms in $C_n$) in Formula (I) can be proportionally increased so as to provide larger (i.e., higher molecular weight) self-assembled molecules which can have a similar balance of attractive and repulsive forces. For example, o can represent an integer from 2 to 4, p can represents an integer from 10 to 40, and q can represents an integer from 7 to 14, and n can range from 20 to 40 (e.g., $C_n$ represents a $C_{20}$-$C_{40}$ alkyl group); or o can represents an integer from 4 to 6, p can represents an integer from 20 to 60, and q can represents an integer from 12 to 21, and n can range from 30 to 60 (e.g., $C_n$ represents a $C_{30}$-$C_{60}$ alkyl group).

The present disclosure describes the identification of a peptide (HN17), bearing SEQ ID NO: 1 and (HN18), bearing SEQ ID NO: 7, that are specifically internalized by the human head and neck squamous carcinoma cells or certain other solid tumor tissue cells, such as breast cancer cells. The inventors envision the use of the HN17 and/or HN18 peptide to achieve tumor-tissue specific delivery of diagnostics and anticancer drugs to cancerous tissue. Thus, in certain embodiments of the disclosure, the inventors describe methods developed to conjugate anticancer drugs with the HN17 and/or HN18 peptide and methods that allow delivery of the peptide-conjugated drugs to specific tumor tissues. In other embodiments, the inventors describe methods that can be used to achieve selective killing of cancer and/or tumor cells in cancer patients by contacting the tumor with pharmaceutically acceptable compositions of the HN17 and/or HN18 peptide and a drug conjugate. In yet other embodiments, methods for imaging cancers using HN17 and/or HN18 peptide conjugated labels are described for both in vitro and in vivo applications, and in other embodiments, the diagnosis and therapeutic labels may be present. Thus, the development of cancer therapeutic and diagnostic kits are described.

In the past, antibodies recognizing tumor-specific antigens have been used to deliver cytotoxic drugs to tumors. However, these immunoconjugates have shown limited effectiveness towards solid tumors due to their inability to penetrate tumor tissue. In contrast, the 12-mer peptide (HN17) and 11-mer peptide (HN18) that the inventors have isolated are $\frac{1}{100}^{th}$ in mass when compared to typical antibodies and is capable of penetrating tumors such as human head and neck squamous cell cancer (HNSCC) xenograft, formed in nude mice. Thus, by conjugating the HN17 or HN18 peptide to drugs, the inventors have developed a tumor-specific delivery system for drugs in systemic deposits of cancer cells.

HN17 was obtained by modification of HN-1 which had previously been shown to be specific for certain cancers. Through fluorescence microscopy, the internalization of fluorescent dye-conjugated HN17 and HN18 peptide into HNSCC cells was documented in vitro. The peptide localized in cytoplasm after entry. This demonstrates that the peptide is specific for certain cancers. Furthermore, the HN17 and HN18 peptide bound preferentially to HNSCC cells as compared to normal cells at the primary cell level. In vivo, intravenously injected HN17 and HN18 peptide localized to HNSCC xenograft formed in nude mice. The peptide accumulated throughout the tumor, demonstrating its ability to penetrate the interior of the tumor mass.

As disclosed herein, the uptake of HN17 was significantly better than HN-1. Nevertheless, the addition of an N-terminal lipophile to HN17 dramatically increased cellular uptake beyond HN17 alone. Accordingly, in one aspect, disclosed herein are peptides such as HN17 comprising an N-terminal lipophile such as fmoc or 4Iph. Once discovering that the uptake of HN17 was increased with the presence of an N-terminal lipophile, HN-1 (SEQ ID NO: 2) HNscr (SEQ ID NO: 3), HNJ (SEQ ID NO: 4), SEQ ID NO: 5, SEQ ID NO: 6, SEQ ID NO: 7, SEQ ID NO: 8, and SEQ ID NO: 9 were each modified to comprise an N-terminal lipophile (Tables 1 and 3) with uptake in SEQ ID Nos: 2, 5, 6, and 7 increasing with the addition of fmoc and/or 4Iph. In one aspect, the amino terminal amino acid of HN17 (the threonine) can be removed from f-HN17 (i.e., T(f)LPNSNH/KQGL as set forth in Table 3) when 4Iph is added, thus giving rise to 4Iph-f-HN18. Accordingly in one aspect, disclosed herein are peptides as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9, wherein the peptide has been modified to comprise an N-terminal lipophile, wherein the N-terminal lipophile comprises Fluorenylmethyloxycarbonyl (Fmoc), 4-para-iodobenzyl (4Iph), 4-para-iodo-benzoyl, or 3-iodotyrosine (3IY). In one aspect the modified peptide can comprise 4Iph-f-HN17 or 4Iph-f-HN18.

To mimic drug delivery, 4Iph-f-HN18 was conjugated to IR800, a complex organic molecule with about 50% molecular mass of Taxol. After intravenous administration, 4Iphf-HN18-IR800 localized to human head and neck cancer cell-derived xenografts. The peptide was found throughout the tumor, demonstrating its capacity to infiltrate tumor tissue carrying a conjugated compound. Peptide uptake with peptide conjugated to IR800 was significantly improved with the addition of fmoc or 4Iph in HN-1 and HN17. Switching the IR800 to the N-terminal end where fmoc or 4Iph had been while increased over HN-1 or HN17, or HN18 alone, was about 60% as effective as our best molecule, 4Iphf-HN18-IR800. The dye, IR800, is an amphiphile, and therefore has both lipophilic and hydrophilic character. In one aspect, disclosed herein are any of SEQ ID Nos: 1-9 comprising a lipophile conjugated to the aminoterminal amino acid and conjugated to a dye such as IR800 or an anti-tumor drug.

In a preferred embodiment of the present disclosure a HN17 or HN18 peptide is conjugated or bound to an antitumor drug such as doxorubicin, bleomycin, TAXOL® (or an analog thereof such as for example, docetaxel), methotrexate, or cetuximab. The antitumor drug is generally hydrophobic enough to permit diffusion across tumor cell membrane, although it is within the scope of the disclosure for the HN17 or HN18 peptide to target the drug to a tumor cell and allow improved translocation or internalization of the anti-tumor drug by other means.

Although the art describes certain peptides that have previously been used to deliver cytotoxic drugs into solid tumors, said peptides did not work with bound protein. One type includes high molecular weight cationic polymers such as poly-L-lysine (Wu et al., 1987) that are selectively retained by the tumors due to the leaky tumor vasculature and the other type includes peptides that bind selectively to tumor vasculature, allowing the destruction of angiogenic endothelial vessels necessary for tumor growth. However, as tumors smaller than 1 mm in diameter can persist through nutrients obtained from adjacent normal blood vessels (Folkman, 1990), the task of eliminating these smaller tumors still remains. The current disclosure resolves these problems by providing a tumor specific peptide, HN17 or HN18, that is capable of penetrating and/or being uptaken by solid tumors. The disclosure is directed to the coupling of an HN17 or HN18 peptide to anticancer drugs, which when administered to an animal, provide tumor-specific targeting of the anticancer drug and therefore provide an effective anticancer therapy. Additionally, the present disclosure provides that the addition of a lipophile on the N-terminal end to other peptides such as HN-1 (SEQ ID NO: HN17 (SEQ ID NO: 1), HN18 (SEQ ID NO: 7),or any other peptide of SEQ ID Nos: 1-9 as revealed in tables 1 and 3 significantly increases the speed and amount of peptide uptake.

The inventors envision that this will allow one to provide the necessary dose of a drug to destroy tumors without being restricted by the occurrence of harmful side effects to other cells. The potential for HN17 or HN18 as a shuttle for drug delivery is further strengthened by the fact that it is nontoxic, nonimmunogenic, stable in vivo (shown by its blood half for metabolism of 5.29 hours), to protect its cargo during transit, and accumulates sufficiently and remains in a tumor within 48 hours.

1. Peptides a) HN17 and HN18

The inventors contemplate the use of HN17 and/or HN18 for the diagnosis and treatment of head and neck cancers. It also is contemplated that HN17 and/or HN18 may be used for the treatment of other solid tumors such as breast cancers, skin cancers, colorectal cancers, prostate cancers, lung cancers and brain tumors.

Thus, in one embodiment, the inventors conjugate Taxol, the most potent chemotherapeutic for treating HNSCC (Shin et al., 1998) and breast cancers, to HN17 and/or HN18. In other embodiments, HN17 and/or HN18 is conjugated to other chemotherapeutic agents.

In other embodiments, there are several uses of HN17 and/or HN18 which include but are not limited to use in tumor imaging, tumor diagnosis, and providing tumor-specificity to gene transfer approaches (Clayman et al, 1995).

In one embodiment of the present disclosure there is a peptide that targets a tumor cell, and in a specific embodiment is internalized by the tumor cell. An object of the present disclosure is a peptide comprising or consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, and/or SEQ ID NO: 9, In a preferred embodiment of the present disclosure there is internalization of the peptide, although it is within the scope of the present disclosure to utilize a HN17 peptide (SEQ ID NO: 1) or another internalizing peptide (HN18) (SEQ ID NO: 7) to target through direct or indirect means or mechanisms an anti-cancer drug to a tumor.

In one aspect, there is a composition comprising a drug and a HN17 and/or HN18 peptide which targets a tumor cell and in a specific embodiment becomes internalized by said tumor cell. In specific embodiments, the drug is a chemotherapeutic agent, a cytotoxic agent, an apoptotic agent, a DNA-damaging agent, or Taxol. In a specific embodiment, the drug is cisplatin (CDDP), carboplatin, procarbazine, mechlorethamine, cyclophosphamide, ifosfamide, melphalan, chlorambucil, bisulfan, nitrosurea, dactinomycin, daunorubicin, doxorubicin, bleomycin, plicomycin, mitomycin, etoposide (VP16), tamoxifen, transplatinum, 5-fluorouracil, vincristin, vinblastin or methotrexate.

b) Variants of HN17 and HN18

Amino acid sequence variants of HN17 and/or HN18 also are encompassed by the present disclosure. Amino acid sequence variants of the polypeptide can be substitutional variants, deletional variants, or insertional variants.

Insertional mutants typically involve the addition of material at a non-terminal point in the peptide. This may include the insertion of a few residues; an immunoreactive epitope; or simply a single residue. The added material may be modified, such as by methylation, acetylation, and the like. Alternatively, additional residues may be added to the N-terminal or C-terminal ends of the peptide.

Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture.

Substitutional variants typically contain the exchange of one amino acid for another at one or more sites within the peptide, and may be designed to modulate one or more properties of the peptide, such as stability against proteolytic cleavage, without the loss of other functions or properties.

Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues.

Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place.

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, substitutions are referred to as conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine or any of the substitutions listed in Table 2.

TABLE 2

Amino Acid Substitutions
Original Residue Exemplary Conservative
Substitutions, others are known in the art.

| | |
|---|---|
| Ala | Ser |
| Arg | Lys; Gln |

TABLE 2-continued

Amino Acid Substitutions
Original Residue Exemplary Conservative
Substitutions, others are known in the art.

| Original | Substitutions |
|---|---|
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. Freeman & Co., San Francisco pp 79-86 [1983]), acetylation of the N-terminal amine and, in some instances, amidation of the C-terminal carboxyl.

The following is a discussion based upon changing of the amino acids of a peptide to create an equivalent, or even an improved, second-generation molecule. For example, certain amino acids may be substituted for other amino acids in a peptide/protein structure without appreciable loss of interactive binding capacity with structures such as, for example, binding sites on substrate molecules or antigen-binding regions of antibodies. Since it is the interactive capacity and nature of a peptide/protein that defines that peptide/protein's biological functional activity, certain amino acid substitutions can be made in a peptide/protein sequence, and its underlying DNA coding sequence, and nevertheless obtain a protein with like properties. It is thus contemplated that various changes may be made in the DNA sequences of genes without appreciable loss of their biological utility or activity, as discussed below. Furthermore, the amino acids of the present disclosure may contain alterations such as methylation, acetylation, myristilation, and the like.

In making such changes, the hydropathic index of amino acids may be considered. The importance of the hydropathic amino acid index in conferring interactive biologic function on a peptide/protein is generally understood in the art (Kyte and Doolittle, 1982). It is accepted that the relative hydropathic character of the amino acid contributes to the secondary structure of the resultant peptide/protein, which in turn defines the interaction of the peptide/protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a peptide/protein with similar biological activity, i.e., still obtain a biological functionally equivalent peptide/protein. In making such changes, the substitution of amino acids whose hydropathic indices are within .+−.2 is preferred, those which are within .+−.1 are particularly preferred, and those within .+−.0.5 are even more particularly preferred.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0.+−.1); glutamate (+3.0.+−.1); serine (+0.3); asparagine (+0.2); glutamine (+0.2); glycine (0); threonine (−0.4); proline (−0.5.+−.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within .+−.2 is preferred, those that are within .+−.1 are particularly preferred, and those within .+−.0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine. However, alterations to the amino acids of the is present disclosure may be other than conservative and still within the scope of the present disclosure so long as the peptides still retain the function to target tumor cells.

Another embodiment for the preparation of peptides according to the disclosure is the use of peptide mimetics. Mimetics are peptide-containing molecules that mimic elements of protein secondary structure. See, for example, Johnson et al., 1993. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of HN17 and/or HN18, but with altered and even improved characteristics. For example, substitution of amino acids to generate motifs that have stronger binding to tumor cells; or that can be specifically tailor-made to bind different types of tumor cells can allow the generation of more HN17 and/or HN18 related peptides, each different for a different tumor-type.

In an embodiment of the present disclosure there are additional means associated with a peptide comprising HN17 and/or HN18 or a fragment or derivative thereof which facilitate transduction or internalization of the peptide-antitumor composition conjugate to a tumor cell. In a specific embodiment, a protein transduction domain is also bound, conjugated, or otherwise associated with a HN17 and/or HN18/anti-tumor composition conjugate. In another specific embodiment the protein transduction domain is the HIV TAT protein (Schwarze) et al., 1999), and the addition of the protein transduction domain facilitates delivery to a tumor cell, including a brain tumor cell as this domain permits crossing of the blood-brain barrier. Thus, in this embodiment of the present disclosure, although the protein transduction domain facilitates delivery to any tissue, the HN17 and/or HN18 peptide of the present disclosure directs the entire complex specifically to a tumor cell such as a head and neck cancer cell, a breast cancer cell or a brain cancer cell, and the protein transduction domain is primarily an auxiliary means to facilitate that delivery and transduction of the antitumor drug complex. Other protein transduction domains are within the scope of the disclosure and are known in the art.

A skilled artisan is aware that one could easily screen or test a variant to determine whether the variant still retained tumor targeting properties. That is, in accordance with the methods provided herein such as in the Examples, a HN17 and/or HN18 peptide variant or other internalizing peptide variant may be conjugated to a detectable label, introduced to a cell, and assayed for internalization by the cell. The assay method in a preferred embodiment is fluorescence microscopy, although a skilled artisan is aware that the assay method should be used in accordance with the type of label utilized. In addition or alternative to this in vitro method, an in vivo internalization assay may be used. For example, the variant conjugated to a detectable label is introduced into an animal, such as a nude mouse harboring a tumor or cancerous tissue, and tumor tissue of the animal is assayed for detection of the label. A skilled artisan may use other methods known in the art or variations of these methods to test for targeting of an internalizing peptide, such as HN17 and/or HN18, to a cell.

It is understood that there are numerous amino acid and peptide analogs which can be incorporated into the disclosed compositions. For example, there are numerous D amino acids or amino acids which have a different functional substituent than L amino acids. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way.

Molecules can be produced that resemble peptides, but which are not connected via a natural peptide linkage. For example, linkages for amino acids or amino acid analogs can include —CH$_2$NH—, —CH$_2$S—, —CH$_2$CH$_2$—, —CH=CH— (cis and trans), —COCH$_2$—, —CH(OH) CH$_2$—, and —CHH$_2$SO— (These and others can be found in Spatola, A. F. in *Chemistry and Biochemistry of Amino Acids, Peptides, and Proteins*, B. Weinstein, eds., Marcel Dekker, New York, p. 267 (1983); Spatola, A. F., Vega Data (March 1983), Vol. 1, Issue 3, Peptide Backbone Modifications (general review); Morley, *Trent Pharm Sci* (1980) pp. 463-468; Hudson, D. et al., Int J Pept Prot Res 14:177-185 (1979) (—CH$_2$NH—, CH$_2$CH$_2$—); Spatola et al. *Life Sci* 38:1243-1249 (1986) (—CHH$_2$—S); Hann *J. Chem. Soc Perkin Trans.* I 307-314 (1982) (—CH—CH—, cis and trans); Almquist et al. *J. Med. Chem.* 23:1392-1398 (1980) (—COCH$_2$—); Jennings-White et al. *Tetrahedron Lett* 23:2533 (1982) (—COCH$_2$—); Szelke et al. European Appln, EP 45665 CA (1982): 97:39405 (1982) (—CH(OH) CH$_2$—); Holladay et al. *Tetrahedron*. Lett 24:4401-4404 (1983) (—C(OH)CH$_2$—); and Hruby *Life Sci* 31:189-199 (1982) (—CH$_2$—S—); each of which is incorporated herein by reference. A particularly preferred non-peptide linkage is —CH$_2$NH—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations.

c) Synthetic Peptides

The present disclosure describes HN17 and/or HN18, HN17 and/or HN18-related peptides, and other cancer-cell specific peptides for use in various embodiments of the present disclosure. These peptides have the ability to be specifically uptaken by cancer/tumor cells and not by normal cells. The HN17 peptide is a 12-mer and the HN18 peptide is an 11-mer. However, one can add other sequences to the 12 mer peptide. Also contemplated are other variants and HN17 or HN 18 related peptides that still retain the ability to translocate through the tumor cell membranes. Such peptides can generally comprise the entire HN17 or HN18 sequence, or portions thereof, and be at least four, five, six, seven, eight, nine, ten, eleven, twelve, thirteen, fourteen, fifteen, sixteen, seventeen, eighteen, nineteen, twenty, twenty one, twenty two, twenty three, twenty four, twenty five amino acid residues in length, and may be 5-10, 10-15, 15-20, 20-25, 25-30, 30-35, 35-40, 40-45 or even 55-50 residues or so long.

Because of their relatively small size, the peptides of the disclosure can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides.

2. Conjugating Methods

In an embodiment of the present disclosure, an antitumor compound is conjugated to a HN17 and/or HN18 peptide for methods to kill a cancer cell. In another embodiment of the present disclosure, a detectable label is conjugated to a HN17 and/or HN18 peptide for diagnostic and imaging methods directed to a cancer cell. In a specific embodiment, the label is visualized directly. In another embodiment, the label is visualized by a secondary means, such as visualization of a second biological entity which detects the label.

In an object of the present disclosure a HN17 and/or HN18 peptide is conjugated to an antitumor drug or composition. In a specific embodiment, the peptide is conjugated to a liposome which contains an antitumor drug or composition. Conjugation means such as those taught by Bauminger and Wilchek (1980) or Nagy et al. (1996), both herein incorporated by reference, are well known in the art. In an embodiment of the present disclosure, an antitumor drug or composition is conjugated by a carbodiimide. In a specific embodiment of the present disclosure, an antitumor drug such as doxorubicin is conjugated by 1-ethyl-3-(3-dimethylaminopropyl) carbodiimide hydrochloride (EDC) and N-hydroxysuccinimide (NHS), as taught in such references as Arap et al. (1999). Alternatively, a HN17 and/or HN18 peptide is conjugated to an antitumor drug using the method of Brown et al. (1995), which utilizes a Ni(II) complex of a tripeptide NH.sub.2-Gly-Gly-His-COOH (SEQ ID NO:2) in the presence of oxidants such as ozone and monoperoxyphthalic acid.

3. Conjugates

Conjugates for labeling a HN17 or HN18 peptide (such as for example SEQ ID NO: 1 or SEQ ID NO: 7) for the purpose of detecting or imaging a cancer cell include radiolabels, nuclear magnetic spin-resonance atoms such as chelated Fe(III), Mn(II) and Gd(III) or FeO nanoparticles, fluorescent labels and enzyme tags capable of generating a colored product upon contact with an appropriate substrate. For example, the conjugate can be IRDye800 (IR800).

As used herein, a conjugate can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson-; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DilC18(5)); DIDS; Dihydrorhodamine 123 (DHR); Dil (DilC18(3)); I Dinitrophenol; DiO (DiOC18(3)); DiR; DiR (DilC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; FluorX; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T);

GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium Iodide (PI); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodaminelsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GIP; YFP; YO-PRO-1; YO-PRO 3; YOYO-1; YOYO-3; Sybr Green; Indocyanine Green; Thiazole orange (intercelating dyes); semiconductor nanoparticles such as quantum dots; or caged fluorophore (which can be activated with light or other electromagnetic energy source), or a combination thereof.

A modifier unit such as a radionuclide can be incorporated into or attached directly to any of the compounds described herein by halogenation. Examples of radionuclides useful in this embodiment include, but are not limited to, tritium, iodine-125, iodine-131, iodine-123, iodine-124, astatine-210, carbon-11, carbon-14, nitrogen-13, fluorine-18. In another aspect, the radionuclide can be attached to a linking group or bound by a chelating group, which is then attached to the compound directly or by means of a linker. Examples of radionuclides useful in the apset include, but are not limited to, Tc-99m, Re-186, Ga-68, Re-188, Y-90, Sm-153, Bi-212, Cu-67, Cu-64, Lu-177, and Cu-62. Radiolabeling techniques such as these are routinely used in the radiopharmaceutical industry.

The radiolabeled compounds are useful as imaging agents to diagnose neurological disease (e.g., a neurodegenerative disease) or a mental condition or to follow the progression or treatment of such a disease or condition in a mammal (e.g., a human). The radiolabeled compounds described herein can be conveniently used in conjunction with imaging techniques such as positron emission tomography (PET) or single photon emission computerized tomography (SPECT).

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

4. Antioxidants

Generally, antioxidants are compounds that get react with, and typically get consumed by, oxygen. Since antioxidants typically react with oxygen, antioxidants also typically react with the free radical generators, and free radicals. ("The Antioxidants—The Nutrients that Guard Your Body" by Richard A. Passwater, Ph. D., 1985, Keats Publishing Inc., which is herein incorporated by reference at least for material related to antioxidants). The compositions can contain any antioxidants, and a non-limiting list would included but not be limited to, non-flavonoid antioxidants and nutrients that can directly scavenge free radicals including multicarotenes, beta-carotenes, alpha-carotenes, gamma-carotenes, lycopene, lutein and zeanthins, selenium, Vitamin E, including alpha-, beta-, and gamma- (tocopherol, particularly .alpha.-tocopherol, etc., vitamin E succinate, and trolox (a soluble Vitamin E analog) Vitamin C (ascoribic acid) and Niacin (Vitamin B3, nicotinic acid and nicotinamide), Vitamin A, 13-cis retinoic acid, N-acetyl-L-cysteine (NAC), sodium ascorbate, pyrrolidin-edithio-carbamate, and coenzyme Q10; enzymes which catalyze the destruction of free radicals including peroxidases such as glutathione peroxidase (GSHPX) which acts on $H_2O_2$ and such as organic peroxides, including catalase (CAT) which acts on $H_2O_2$, superoxide dismutase (SOD) which disproportionates $O_2H_2O_2$ glutathione transferase (GSHTx), glutathione reductase (GR), glucose 6-phosphate dehydrogenase (G6PD), and mimetics, analogs and polymers thereof (analogs and polymers of antioxidant enzymes, such as SOD, are described in, for example, U.S. Pat. No. 5,171,680 which is incorporated herein by reference for material at least related to antioxidants and antioxidant enzymes); glutathione; ceruloplasmin; cysteine, and cysteamine (beta-mercaptoethylamine) and flavonoids and flavenoid like molecules like folic acid and folate. A review of antioxidant enzymes and mimetics thereof and antioxidant nutrients can be found in Kumar et al, *Pharmac. Ther. Vol* 39: 301, 1988 and Machlin L. J. and Bendich, *F.A.S.E.B. Journal* Vol. 1:441-445, 1987 which are incorporated herein by reference for material related to antioxidants.

Flavonoids, also known as "phenylchromones," are naturally occurring, water-soluble compounds which have antioxidant characteristics. Flavonoids are widely distributed in vascular plants and are found in numerous vegetables, fruits and beverages such as tea and wine (particularly red wine). Flavonoids are conjugated aromatic compounds. The most widely occurring flavonoids are flavones and flavonols (for example, myricetin, (3,5,7,3',4',5'-hexahydroxyflavone), quercetin (3,5,7,3',4'-pentahydroxyflavone), kaempferol (3,5,7,4'-tetrahydroxyflavone), and flavones apigenin (5,7, 4'-trihydroxyflavone) and luteolin (5,7,3',4'-tetrahydroxyflavone) and glycosides thereof and quercetin).

5. Nucleic Acids

There are a variety of molecules disclosed herein that are nucleic acid based, including for example the nucleic acids that encode, for example HN17 and/or HN18, or fragments thereof, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the anti sense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687, 808, Englisch et al., Angewandte Chemie, International Edition, 1991, 30, 613, and Sanghvi, Y. S., Chapter 15, *Antisense Research and Applications*, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modification, such as 2'-O-methoxyethyl, to achieve unique properties such as increased duplex stability.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O-, S-, or N-alkyl; O-, S-, or N-alkenyl, O-, S- or N-alkynyl, or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[$(CH_2)_nO]_mCH_3$, —O$(CH_2)_nOCH_3$, —O$(CH_2)_nNH_2$, —O$(CH_2)_nCH_3$, —O$(CH_2)_n$—$ONH_2$, and —O$(CH_2)_nON[(CH_2)_nCH_3)]_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as $CH_2$ and S. Nucleotide sugar analogs may also have sugar mimetics such as cyclobutyl moieties in place of the pentofuranosyl sugar.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphatriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

It is also understood in a nucleotide substitute that both the sugar and the phosphate moieties of the nucleotide can be replaced, by for example an amide type linkage (aminoethylglycine) (PNA).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Let.,* 1993, 3, 2765-2770), a thiocholesterol (Oberhauser et al., *Nucl. Acids Res.,* 1992. 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 29-237), or an octadecylamine or hexylamino-carbonyl-oxycholesterol moiety (Crooke et al., *Pharmacol. Exp. Ther.,* 1996, 277, 923-937.

A Watson-Crick interaction is at least one interaction with the Watson-Crick face of a nucleotide, nucleotide analog, or nucleotide substitute. The Watson-Click face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

6. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 by in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the $E.\ coli$ lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., $J.\ Molec\ Appl.\ Genet.$ 1: 327 (1982)), mycophenolic acid, (Mulligan, R. C. and Berg, P. $Science$ 209: 1422 (1980)) or hygromycin, (Sugden, B. et al., $Mol.\ Cell.\ Biol.$ 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

7. In Vivo Imaging

The disclosure also provides in vivo methods of imaging cancer using the HN17 and/or HN18 and other cancer specific protein conjugates. The term "in vivo imaging" refers to any non-invasive method that permits the detection of a peptide, or fragment thereof, that specifically binds to cancer cells located in the body of an animal or human subject. In the present disclosure, as the peptide, or a fragment thereof, is uptaken by the cancer cell specifically the inventors envision detecting the uptake of the peptide by conjugating the peptide or fragment thereof to a suitable detection agent.

In accordance with the isolation of internalizing peptides and detection of cancer by methods of the present disclosure, a skilled artisan is aware that, an internalizing peptide is utilized to image or diagnose a tumor cell. A skilled artisan, as taught by the methods described herein in the Examples directed to HN17 or HN18, may isolate an internalizing peptide which internalizes, identifies or detects a specific cancer cell type. Although the Examples are directed to head and neck cancer cells, such as with squamous cell carcinoma, any cancer cell type may be utilized by the same methods to identify specific internalizing peptides for that cancer cell type. In accordance with this specific embodiment, a skilled artisan can use the methods described herein to identify other peptides which internalize other tumors or cancerous tissue including but not limited to lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma, glioblastoma, stomach cancer, ovarian cancer, osteosarcoma, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, colorectal cancer, genitourinary cancer, pulmonary cancer, esophageal carcinoma, head and neck carcinoma, large bowel cancer, hematopoietic cancers; testicular cancer; prostatic cancer, or pancreatic cancer.

The imaging methods generally involve administering to an animal or subject an imaging-effective amount of a detectable-label conjugated to a peptide as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9 (for example the HN17 peptide, HN18 peptide, or any fragment thereof), in a pharmaceutically effective carrier, and then detecting the uptake of the labeled HN17 peptide-label conjugate and/or HN18 peptide-label conjugate by the cancerous tissue. The detectable label is preferably a spin-labeled molecule or a radioactive isotope that is detectable by non-invasive methods.

An "imaging effective amount" is an amount of a detectably-labeled peptide as set forth in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9 (for example the HN17 peptide, HN18 peptide, or any fragment thereof), that when administered is sufficient to enable later detection of uptake of the labeled-peptide or fragment to cancer tissue. The effective amount of the peptide-label conjugate is allowed sufficient time to come into contact with the cancer tissue present within the tissues of the patient, and the patient is then exposed to a detection device to identify the detectable label.

Thus, one embodiment of the disclosure provides the HN17 and/or HN18-dye conjugates or constructs for imaging which have the ability to provide an image of the tumor, for example, through magnetic resonance imaging, x-ray imaging, computerized emission tomography and the like. Elements particularly useful in Magnetic Resonance Imaging ("MRI") include the nuclear magnetic spin-resonance isotopes $^{157}$Gd, $^{55}$Mn, $^{162}$Dy, $^{52}$Cr, and $^{56}$Fe, with gadolinium often being preferred. Radioactive substances, such as technicium$^{99m}$ or indium$^{111}$, that may be detected using a gamma scintillation camera or detector also may be used. Further examples of metallic ions suitable for use in this disclosure are $^{123}$I, $^{131}$I, $^{97}$Ru, $^{67}$Cu, $^{67}$Ga, $^{125}$I, $^{68}$Ga, $^{72}$As, $^{89}$Zr, $^{18}$F, and $^{201}$Tl.

A radionuclide may be bound to the HN17 and/or HN18 peptide or fragment thereof either directly or indirectly by using an intermediary functional group. Intermediary functional groups which are often used to bind radioisotopes which exist as metallic ions to antibody are diethylenetri-aminepentaacetic acid (DTPA), DOTA (dodecane tetratacidic acid, DO3A (dodecanetriacidic acid), NOTA (cyclononane triacetic acid) and ethylene diaminetetracetic acid (EDTA), and R-DO3A where R is a moiety containing a hydroxyl that binds to metal.

Administration of the labeled HN17 and/or HN18 peptide or fragment thereof, may be local or systemic and accomplished intravenously, intra-arterially, via the spinal fluid or the like. Administration also may be intradermal or intracavitary, depending upon the body site under examination. After a sufficient time has lapsed for the labeled HN17 and/or HN18 peptide or fragment thereof to bind to the diseased tissue, in this case cancer tissue, for example 30 min to 48 h, the area of the subject under investigation is then examined by the imaging technique. MRI, SPECT, planar scintillation imaging, PET, NRF Optical imaging, and other emerging imaging techniques may all be used. Multiple imaging techniques may be utilized to clarify or confirm detection.

The distribution of the bound radioactive isotope and its increase or decrease with time is monitored and recorded. By comparing the results with data obtained from studies of clinically normal individuals, the presence and extent of the diseased tissue can be determined.

The exact imaging protocol will necessarily vary depending upon factors specific to the patient, and may also depend upon the body site under examination, method of administration, type of label used and the like. The determination of specific procedures is, however, routine to the skilled artisan. Although dosages for imaging embodiments are dependent upon the age and weight of patient, a one time dose of about 0.1 to about 20 mg, more preferably, about 1.0 to about 2.0 mg of labeled HN17 and/or HN18 peptide or fragment thereof per patient is contemplated to be useful. Imaging dosages of 10-100 nmol in a 20 g mouse or 0.5 to 5 micromol/kg were highly effective in tumor mice, and 40 nmol per mouse or 2 micromol/kg, is preferred. In human use the dose would scale up from the mouse dose according to the weight or body surface area of the human patient, for example from the 0.02 kg mouse to the 70 kg patient, the dose would increase (using weight) to about 3500 times greater than 40 nmoles, or about 140 micromoles.

Thus, in one aspect disclosed herein are methods of detecting a cancer cell in a subject comprising administering to the subject a composition comprising a peptide, wherein said peptide comprises the amino acid sequence of TLPNSNHIKQGL (SEQ ID NO: 1), TSPLNIHNGQKL (SEQ ID NO: 2), LNKQTHGLIPNS (SEQ ID NO: 3), NQHSKNTLLIGP (SEQ ID NO: 4), LKQGNHINLPS (SEQ ID NO: 5), YSPLNIHNGQKL (SEQ ID NO: 6), LPNSNHIKQGL (SEQ ID NO: 7), YLPNSNHIKQGL (SEQ ID NO: 8), or FLPNSNHIKQGL (SEQ ID NO: 9); wherein the peptide is conjugated to a detectable label. In one aspect, the peptide further comprises a lypophile (such as, for example, Fluorenylmethyloxycarbonyl, 4-para-iodo-benzyl, 4-para-iodo-benzoyl, and/or 3-iodotyrosine) attached to the amino terminal amino acid.

8. Isolation of Internalizing Peptides

In an embodiment of the present disclosure there is a method provided herein for isolating an internalizing peptide. Although a skilled artisan is aware that these methods are generally directed to identifying a peptide which internalizes into a tumor or cancerous tissue, a specific example is provided in the Examples directed to identification of HN17 and/or HN18 peptide (such as, for example, SEQ ID NO: 1 or SEQ ID NO: 7) for use in detecting, imaging or identifying, a cancer, such as, for example, a squamous cell carcinoma. In accordance with this specific embodiment, a skilled artisan can use the methods described herein to identify other peptides which internalize other tumors or cancerous tissue including but not limited to lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma, glioblastoma, stomach cancer, ovarian cancer, osteosarcoma, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, colorectal cancer, genitourinary cancer, pulmonary cancer, esophageal carcinoma, head and neck carcinoma, large bowel cancer, hematopoietic cancers; testicular cancer; prostatic cancer, or pancreatic cancer.

9. Detection of Cancer by Methods of the Present Disclosure

In an embodiment of the present disclosure there is a method for detecting cancer. Although the description of the method provided herein is in accordance with that in which a skilled artisan is generally taught how to isolate an internalizing peptide and utilize this peptide to detect a cancer cell, a specific example is described in the Examples regarding isolation of HN17 and/or HN18 peptide (such as, for example, SEQ ID NO: 1 or SEQ ID NO: 7) as an internalizing peptide and its utilization for detection of a cancer, such as, for example, squamous cell carcinoma.

Specific methods steps may include obtaining an internalizing peptide; conjugating a detectable label to the peptide; administering the conjugated peptide and label to an organism; and detecting binding of the conjugate to cancer cells by suitable detection means.

In an additional embodiment the method for detecting cancer comprises obtaining a peptide library; individually contacting peptides of the library with members of a cell population; assaying for endocytosis of the peptides by the members of the cell population to identify an internalizing peptide; conjugating a detectable label to said peptide; administering the conjugated peptide and label to an organism; and detecting binding of the conjugate to a cell by suitable detection means. Although the cell may be a squamous cell carcinoma cell, including a head and neck cancer cell, it may alternatively be a cell from lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma, glioblastoma, stomach cancer, ovarian cancer, osteosarcoma, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, colorectal cancer, genitourinary cancer, pulmonary cancer, esophageal carcinoma, head and neck carcinoma, large bowel cancer, hematopoietic cancers; testicular cancer; prostatic cancer, or pancreatic cancer.

10. Cancer Therapies

In an embodiment of the present disclosure there is a treatment for cancer utilizing a peptide or fragment of any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9. The patient to be treated may be an infant, child, adolescent or adult and in a preferred embodiment shows an improvement in at least one symptom of the disease, including a decrease in tumor size.

A wide variety of cancer therapies, known to one of skill in the art, may be used in combination (either concurrently administered, admixed at the time of administration, formulated in the same composition, or covalently attached) with the tumor cell specific-peptide of the disclosure. The inventors contemplated using the tumor cell specific-peptide of the disclosure to achieve specific and targeted delivery of the various chemotherapeutics known in the art to cancer and/or tumor cells. Other embodiments contemplate the use of the tumor cell specific-peptide of the disclosure to target anticancer drugs in addition to other cancer therapies known in the art. Some of the existing cancer therapies and chemotherapeutic agents are described below. One of skill in the art will recognize the presence and development of other anticancer therapies which can be used in conjugation with the tumor cell specific-peptide of the disclosure and will further recognize that the use of the tumor cell specific-peptide of the disclosure will not be restricted to the agents described below. In one aspect, disclosed herein is composition comprising a peptide (such as, for example SEQ ID NO: 1 or SEQ ID NO: 7) wherein the peptide is covalently linked at the carboxy terminal end of the peptide or at a lysine residue to an anti-cancer agent (such as, for example, doxorubicin, bleomycin, docetaxel, methotrexate, or cetuximab or any other anti-cancer agent disclosed herein). In another aspect disclosed herein are compositions comprising a peptide (such as, for example SEQ ID NO: 1 or SEQ ID NO: 7) and anti-cancer agent (such as, for example, doxorubicin, bleomycin, docetaxel, methotrexate, or cetuximab or any other anti-cancer agent disclosed herein).

11. Radiotherapeutic Agents

Radiotherapeutic agents emit radiation that induces DNA damage for example, .gamma.-irradiation, beta radiation, alpha radiation, X-rays, UV-irradiation, microwaves, electronic emissions, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes. HN17 and/or HN18 can be used to deliver to the cancer cells two effective means of radiotherapy. One is one or more radioactive atoms, and the second is radio sensitizer molecules as adjuncts to externally applied radiation, such as beam radiation. A radio sensitizer molecule could also be targeted attached to HN17 and/or HN18, and a second targeted radioisotope atom could be separately targeted to the cancer by attaching it also to HN17 and/or HN18 or to any other means of directing it to the cancer cell containing the radiosenstizer conjugated to HN17 and/or HN18.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells. Generally speaking at least 25 Gy and preferably at least 50 Gy are targeted to the cancer tumor.

In the context of the present disclosure radiotherapy may be used in addition to using the tumor cell specific-peptide of the disclosure to achieve cell-specific cancer therapy.

In some cases, it can be convenient to prepare the complexes comprising a radionuclide, at or near the site where they are to be used (e.g., in a hospital pharmacy or clinic) Accordingly, in some embodiments, the disclosed peptide comprises a metal chelator uncomplexed with a metal ion. In such embodiments, the disclosed peptide can be complexed with a suitable metal ion prior to administration. In other embodiments, the disclosed peptide comprises a metal chelator complexed with a suitable metal ion (e.g., a paramagnetic metal ion or a radionuclide).

Suitable metal chelators include, for example, linear, macrocyclic, terpyridine, and $N_3S$, $N_2S_2$, or $N_4$ chelators (see also, U.S. Pat. Nos. 4,647,447, 4,957,939, 4,963,344, 5,367,080, 5,364,613, 5,021,556, 5,075,099, 5,886,142, the disclosures of which are incorporated by reference herein in their entirety), and other chelators known in the art including, but not limited to, HYNIC, DTPA, EDTA, DOTA, DO3A, TETA, and bisamino bisthiol (BAT) chelators (see also U.S. Pat. No. 5,720,934). For example, macrocyclic chelators, and in particular $N_4$ chelators are described in U.S. Pat. Nos. 4,885,363; 5,846,519; 5,474,756; 6,143,274; 6,093,382; 5,608,110; 5,665,329; 5,656,254; and 5,688,487, the disclosures of which are incorporated by reference herein in their entirety. Certain $N_3S$ chelators are described in PCT/CA94/00395, PCT/CA94/00479, PCT/CA95/00249 and in U.S. Pat. Nos. 5,662,885; 5,976,495; and 5,780,006, the disclosures of which are incorporated by reference herein in their entirety. The chelator may also include derivatives of the chelating ligand mercapto-acetyl-glycyl-glycyl-glycine (MAG3), which contains an $N_3S$, and $N_2S_2$ systems such as MAMA (monoamidemonoaminedithiols), DADS ($N_2S$ diaminedithiols), CODADS and the like. These ligand systems and a variety of others are described in Liu and Edwards, Chem. Rev. 1999, 99, 2235-2268; Caravan et al., Chem. Rev. 1999, 99, 2293-2352; and references therein, the disclosures of which are incorporated by reference herein in their entirety.

The metal chelator may also include complexes known as boronic acid adducts of technetium and rhenium dioximes, such as those described in U.S. Pat. Nos. 5,183,653; 5,387,409; and 5,118,797, the disclosures of which are incorporated by reference herein, in their entirety.

Examples of suitable chelators include, but are not limited to, derivatives of diethylenetriamine pentaacetic acid (DTPA), 1,4,7,10-tetraazacyclotetradecane-1,4,7,10-tetraacetic acid (DOTA), 1-substituted 1,4,7,-tricarboxymethyl 1,4,7,10 tetraazacyclododecane triacetic acid (DO3A), derivatives of the 1-1-(1-carboxy-3-(p-nitrophenyl)propyl-1,4,7,10 tetraazacyclododecane triacetate (PA-DOTA) and MeO-DOTA, ethylenediaminetetraacetic acid (EDTA), and 1,4,8,11-tetraazacyclotetradecane-1,4,8,11-tetraacetic acid (TETA), derivatives of 3,3,9,9-Tetramethyl-4,8-diazaundecane-2,10-dione dioxime (PnAO); and derivatives of 3,3,9,9-Tetramethyl-5-oxa-4,8-diazaundecane-2,10-dione dioxime (oxa PnAO). Additional chelating ligands are ethylenebis-(2-hydroxy-phenylglycine) (EHPG), and derivatives thereof, including 5-Cl-EHPG, 5-Br-EHPG, 5-Me-EHPG, 5-t-Bu-EHPG, and 5-sec-Bu-EHPG; benzodiethylenetriamine pentaacetic acid (benzo-DTPA) and derivatives thereof, including dibenzo-DTPA, phenyl-DTPA, diphenyl-DTPA, benzyl-DTPA, and dibenzyl-DTPA; bis-2 (hydroxybenzyl)-ethylene-diaminediacetic acid (HBED) and derivatives thereof, the class of macrocyclic compounds which contain at least 3 carbon atoms and at least two heteroatoms (O and/or N), which macrocyclic compounds can consist of one ring, or two or three rings joined together at the hetero ring elements, e.g., benzo-DOTA, dibenzo-DOTA, and benzo-NOTA, where NOTA is 1,4,7-triazacyclononane N,N',N''-triacetic acid, benzo-TETA, benzo-DOTMA, where DOTMA is 1,4,7,10-tetraazacyclotetradecane-1,4,7,10-tetra(methyl tetraacetic acid), and benzo-TETMA, where TETMA is 1,4,8,11-tetraazacyclotetradecane-1,4,8,11-(methyl tetraacetic acid); derivatives of 1,3-propylenediaminetetraacetic acid (PDTA) and triethylenetetraaminehexaacetic acid (TTHA); derivatives of 1,5,10-N,N',N''-tris(2,3-dihydroxybenzoyl)-tricatecholate (LICAM) and 1,3,5-N,N',N''-tris(2,3-dihydroxybenzoyl)aminomethylbenzene (MECAM). Examples of representative chelators and chelating groups are described in WO 98/18496, WO 86/06605, WO 91/03200, WO 95/28179, WO 96/23526, WO 97/36619, PCT/US98/01473, PCT/US98/20182, and U.S. Pat. Nos. 4,899,755, 5,474,756, 5,846,519 and 6,143,274, each of which is hereby incorporated by reference in its entirety. The above named DOTA derivatives can also be R-DO3A derivatives where R=H or contains an amide or hydroxyl metal binding aton. In some embodiments, the metal chelator comprises desferrioxamine (also referred to as deferoxamine, desferrioxamine B, desferoxamine B, DFO-B, DFOA, DFB or desferal) or a derivative thereof. See, for example U.S. Pat. Nos. 8,309,583, 4,684,482, and 5,268,165, each of which is hereby incorporated by reference in its entirety for its teaching of desferrioxamine and desferrioxamine derivatives.

As is well known in the art, metal chelators can be specific for particular metal ions. Suitable metal chelators can be selected for incorporation into the self-assembling molecule based on the desired metal ion and intended use of the self-assembling molecule.

Paramagnetic ions form a magnetic moment upon the application of an external magnetic field thereto. Magnetization is not retained in the absence of an externally applied magnetic field because thermal motion causes the spin of unpaired electrons to become randomly oriented in the absence of an external magnetic field. By taking advantage of its property of shortening the magnetic relaxation time of water molecules, a paramagnetic substance is usable as an active component of MRI contrast agents. Suitable paramagnetic transition metal ions include $Cr^{3+}$, $Co^{2+}$, $Mn^{2+}$, $Fe^{2+}$, $Fe^{3+}$, $Zr^{4+}$, $Cu^{2+}$, and $Cu^{3+}$. In preferred embodiments, the paramagnetic ion is a lanthanide ion (e.g., $La^{3+}$, $Gd^{3+}$, $Ce^{3+}$, $Tb^{3+}$, $Pr^{3+}$, $Dy^{3+}$, $Nd^{3+}$, $Ho^{3+}$, $Pm^{3+}$, $Er^{3+}$, $Sm^{3+}$, $Tm^{3+}$, $Eu^{3+}$, $Yb^{3+}$, or $Lu^{3}+$). In MRI, especially preferred metal ions are $Gd^{3+}$, $Mn^{2+}$, $Fe^{3+}$, and $Eu^{2+}$.

MRI contrast agents can also be made with paramagnetic nitroxides molecules in place of the chelating agent and paramagnmetic metal ion.

Suitable radionuclides include $^{99m}Tc$, $^{67}Ga$, $^{68}Ga$, $^{66}Ga$, $^{47}Sc$, $^{51}Cr$, $^{167}Tm$, $^{141}Ce$, $^{111}In$, $^{123}I$, $^{125}I$, $^{131}I$, 124I, $^{18}F$, $^{11}C$, $^{15}N$, 17O, $^{168}Yb$, $^{175}Yb$, $^{140}La$, $^{90}Y$, $^{88}Y$, $^{86}Y$, $^{153}Sm$, $^{166}Ho$, $^{165}Dy$, $^{166}Dy$, $^{62}Cu$, $^{64}Cu$, $^{67}Cu$, $^{97}Ru$, $^{103}Ru$, $^{186}Re$, $^{188}Re$, $^{203}Pb$, $^{211}Bi$, $^{212}Bi$, $^{213}Bi$, $^{214}Bi$, $^{225}Ac$, $^{211}At$, $^{105}Rh$, $^{109}Pd$, $^{117m}Sn$, $^{149}Pm$, $^{161}Tb$, $^{177}Lu$, $^{198}Au$, $^{199}Au$, 89Zr, and oxides or nitrides thereof. The choice of isotope will be determined based on the desired therapeutic or diagnostic application. For example, for diagnostic purposes (e.g., to diagnose and monitor therapeutic progress in primary tumors and metastases), suitable radionuclides include $^{64}Cu$, $^{67}Ga$, $^{68}Ga$, $^{66}Ga$, $^{99m}Tc$, and $^{111}In$, $^{18}F$, $^{89}Zr$, $^{123}I$, $^{131}I$, $^{124}I$, $^{177}Lu$, $^{15}N$, $^{17}O$. For therapeutic purposes (e.g., to provide radiotherapy for primary tumors and metastasis related to cancers of the prostate, breast, lung, etc.), suitable radionuclides include $^{64}Cu$, $^{90}Y$, $^{105}Rh$, $^{111}In$, 131I, $^{117m}Sn$, $^{149}Pm$, $^{153}Sm$, $^{161}Tb$, $^{166}Dy$, $^{166}Ho$, $^{175}Yb$, $^{177}Lu$, $^{186/188}Re$, $^{199}Au$, $^{131}I$, and $^{125}I$, $^{212}Bi$, $^{211}At$.

In the case where the disclosed peptide are designed to be imaged using PET, radionuclides with short half-lives such as carbon-11 (~20 min), nitrogen-13 (~10 min), oxygen-15 (~2 min), fluorine-18 (~110 min), or rubidum-82 (~1.27 min) are often used. In certain embodiments when a non-metal radionuclide is employed, the therapeutic or diagnostic agent comprises a radiotracer covalently attached to the self-assembling molecule. By way of exemplification, suitable $^{18}F$-based radiotracers include $^{18}F$-fluordesoxyglucose (FDG), $^{18}F$-dopamine, $^{18}F$-L-DOPA, $^{18}F$-fluorcholine, $^{18}F$-fluormethylethylcholin, and $^{18}P$-fluordihydrotestosteron.

In the case of self-assembled molecules designed to be imaged using PET, radionuclides with long half-lives such as $^{124}I$, or $^{89}Zr$ are also often used.

12. Surgery

Surgical treatment for removal of the cancerous growth is generally a standard procedure for the treatment of tumors and cancers. This attempts to remove the entire cancerous growth. However, surgery is generally combined with chemotherapy and/or radiotherapy to ensure the destruction of any remaining neoplastic or malignant cells. Thus, in the context of the present disclosure, surgery may be used in addition to using the tumor cell specific-peptide of the disclosure to achieve cell-specific cancer therapy.

13. Chemotherapeutic Agents

As used herein, chemotherapeutic agents refers to any anti-cancer agent regardless of mechanism of action. These can be, for example, agents that directly cross-link DNA, agents that intercalate into DNA, and agents that lead to chromosomal and mitotic aberrations by affecting nucleic acid synthesis.

Agents that directly cross-link nucleic acids, specifically DNA, are envisaged and are shown herein, to eventuate DNA damage leading to a synergistic antineoplastic combination. Agents such as cisplatin, and other DNA alkylating agents may be used.

Agents that damage DNA also include compounds that interfere with DNA replication, mitosis, and chromosomal segregation. Examples of these compounds include verapamil, Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedatin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), *Asparaginase Erwinia chrysanthemi*, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPOX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuxinab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (*Asparaginase Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazotnib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate) Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostirn, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate). Also contemplated herein are chemotherapeutics that are PD1/PDL1 blockade inhibitors (such as, for example, lambrolizumab, nivolumab, pembrolizumab, pidilizumab, BMS-936559, Atezolizumab, Durvalumab, or Avelumab). Widely used in clinical setting for the treatment of neoplasms, these compounds are administered through bolus injections intravenously at doses ranging from 25-75 mg/m.sup.2 at 21 day intervals for adriamycin, to 35-100 mg/msup.2 for etoposide intravenously or orally.

14. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Seater, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the is regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnasis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

15. Kits

Disclosed herein are kits that are drawn to reagents that can be used in practicing the methods disclosed herein. The kits can include any reagent or combination of reagents discussed herein or that would be understood to be required or beneficial in the practice of the disclosed methods. For example, the kits could include primers to perform the amplification reactions discussed in certain embodiments of the methods, as well as the buffers and enzymes required to use the primers as intended. For example, disclosed is a kit for identifying pathologic tissue, comprising one or more of the peptides set forth in TLPNSNHIKQGL (HN17) (SEQ ID NO: 1), TSPLNIHNGQKL (HN1) (SEQ ID NO: 2), LNKQTHGLIPNS (HNscr) (SEQ ID NO: 3), NQHSKNTL-LIGP (HNJ) (SEQ ID NO: 4), LKQGNHINLPS (SEQ ID NO: 5), YSPLNIHNGQKL (SEQ ID NO: 6), LPNSN-HIKQGL (HN18) (SEQ ID NO: 7), YLPNSNHIKQGL (SEQ ID NO: 8), or FLPNSNHIKQGL (SEQ ID NO: 9). Also disclosed are imaging conjugates or labels for detection of the pathologic tissue and/or a lipophile such as a lipophilic drug.

C. METHODS OF MAKING THE COMPOSITIONS

The compositions disclosed herein and the compositions necessary to perform the disclosed methods can be made using any method known to those of skill in the art for that particular reagent or compound unless otherwise specifically noted.

1. Peptide Synthesis

One method of producing the disclosed proteins, such as SEQ ID NO: 1, is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof (Grant G A (1992) *Synthetic Peptides: A User Guide*. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., *Biochemistry*, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) *FEBS Lett*. 307:97-101; Clark-Lewis I et al., *J. Biol. Chem.*, 269:16075 (1994); Clark-Lewis I et al., *Biochemistry*, 30:3128 (1991); Rajarathnam K et al., *Biochemistry* 33:6623-30 (1994)).

Alternatively, unprotected peptide segments are chemically linked where the bond formed between the peptide segments as a result of the chemical ligation is an unnatural (non-peptide) bond (Schnolzer, M et al. *Science*, 256:221 (1992)). This technique has been used to synthesize analogs of protein domains as well as large amounts of relatively pure proteins with full biological activity (deLisle Milton R C et al., *Techniques in Protein Chemistry IV* Academic Press, New York, pp. 257-267 (1992)).

D. METHOD OF TREATING CANCER

The disclosed compositions can be used to treat any disease where uncontrolled cellular proliferation occurs such as cancers. Accordingly, in one aspect disclosed herein are methods of treating a cancer comprising administering to a subject any of the peptides disclosed in Table 1 or Table 3. It is understood that said peptides can comprise an imaging label or conjugate (such as, for example, a fluorochrome or a radio label). In some aspect the peptide can further comprise a lipophile and/or a chemotherapeutic agent. Two different imaging labels, two different therapeutic drugs, or a therapeutic drug plus an imaging label can be simultaneously incorporated in one HN17 or HN18 peptide. The imaging label or the therapeutic drug may also serve as the terminal A non-limiting list of different types of cancers that can be treated by the disclosed compositions is as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas histiocytomas, melanomas, adenomas, hypoxic tumours, myelomas, AIDS-related lymphomas or sarcomas, metastatic cancers, or cancers in general, including Lung, prostate breast, colorectal, pancreatic, leukemia, lymphoma and renal cancer.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma, glioblastoma, stomach cancer, ovarian cancer, osteosarcoma, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, colorectal cancer, genitourinary cancer, pulmonary cancer, esophageal carcinoma, head and neck carcinoma, large bowel cancer, hematopoietic cancers; testicular cancer; prostatic cancer, or pancreatic cancer, including leukemia, and lymphoma.

Compounds disclosed herein may also be used for the treatment of precancer conditions such as cervical and anal dysplasias, other dysplasias, severe dysplasias, hyperplasias, atypical hyperplasias, and neoplasias.

The disclosed methods of treatment contemplate the administration of a composition comprising a peptide comprising the amino acid sequence TLPNSNHIKQGL (HN17) (SEQ ID NO: 1), TSPLNIHNGQKL (HN1) (SEQ ID NO: 2), LNKQTHGLIPNS (HNscr) (SEQ ID NO: 3), NQHSKNTLLIGP (HNJ) (SEQ ID NO: 4), LKQGNHINLPS (SEQ ID NO: 5), YSPLNIHNGQKL (SEQ ID NO: 6), LPNSNHIKQGL (HN18) (SEQ ID NO: 7), YLPNSNHIKQGL (SEQ NO: 8), or FLPNSNHIKQGL (SEQ ID NO: 9). Accordingly, disclosed herein are methods of treating a cancer in a subject comprising administering to the subject a peptide, wherein said peptide comprises the amino acid sequence of TLPNSNHIKQGL (SEQ ID NO: 1), TSPLNIHNGQKL (SEQ ID NO: 2), LNKQTHGLIPNS (SEQ ID NO: 3), NQHSKNTLLIGP (SEQ ID NO: 4), LKQGNHINLPS (SEQ ID NO: 5), YSPLNIHNGQKL (SEQ ID NO: 6), LPNSNHIKQGL (SEQ ID NO: 7), YLPNSNHIKQGL (SEQ ID NO: 8), or FLPNSNHIKQGL (SEQ ID NO: 9). In one aspect, the peptide can be covalently attached to a lipophile such as, for example, Fmoc and/or 4-para-iodo-benzyl (4Iph), wherein the lipophile is attached at the amino terminal end of the peptide (such as, for example, the peptide can be 4Iphf-HN18).

In one aspect, the disclosed methods of treating cancer further contemplate the administration of an anti-cancer agent (also referred to herein as a chemotherapeutic agent). The anti-tumor agent can comprise any anti-cancer agent known in the art including, but not limited to antibodies, tumor infiltrating lymphocytes, checkpoint inhibitors, dendritic cell vaccines, anti-tumor vaccines, immunotherapy, and chemotherapeutic agents. In one aspect, the anti-tumor agent can include, but is not limited to verapamil, Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), *Asparaginase Erwinia chrysanthemi*, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPOX, Carac (Fluorouracil—Topical), Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuxitnab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil—Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (*Asparaginase Erwinia chrysanthemi*), Ethyol (Amifostine), Etopophos (Etoposide Phosphate), Etoposide, Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil—Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil—Topical), Fluorouracil Injection, Fluorouracil—Topical, Flutamide, Folex (Methotrexate), Folex PFS (Methotrexate), FOLFIRI, FOLFIRI-BEVACIZUMAB, FOLFIRI-CETUXIMAB, FOL- FIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide, Ifosfamidum (Ifosfamide), IL-2 (Aldesleukin), Imatinib Mesylate, Imbruvica (Ibrutinib), Imfinzi (Durvatumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R-CHOP, R-CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil—Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zalirap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate). Also contemplated herein are chemotherapeutics that are PD1/PDL1 blockade inhibitors (such as, for example, lambrolizumab, nivolumab, pembrolizumab, pidilizumab, BMS-936559, Atezolizumab, Durvalumab, or Avelumab).

In the methods of treating cancer disclosed herein, the anti-cancer agent can be covalently attached to the peptide (for example attached at the lysine of a peptide or at the carboxy terminal end of the peptide), formulated in the same composition as the peptide, or concurrently administered with the peptide (including admixing or concurrent administration). It is understood and herein contemplated that where an anti-cancer agent (for example, a chemotherapeutic) is used that is lipophilic, the anti-cancer agent can substitute for the 4Iph or Fmoc rather than be attached at the carboxy terminus. Thus, in one aspect, disclosed herein are peptides (such as, for example, HN17 or HN18) covalently attached to a anti-cancer agent, wherein the anti-cancer agent is lipophilic and wherein the anti-cancer agent is attached to the peptide on the amino-terminal portion or end of the peptide. It is further understood and herein contemplated that where the anti-cancer agent is hydrophilic or a peptide, protein, or other large molecule, it can be advantageous to have the anti-cancer agent attached to the peptide on the carboxy terminus or at the lysine.

E. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc), but some errors and deviations should be accounted for. Unless indicated otherwise, parts are parts by weight, temperature is in ° C. or is at ambient temperature, and pressure is at or near atmospheric.

1. Example 1

HN17 Drug Discovery

Head and neck squamous cell carcinoma (HNSCC) is the sixth most common malignancy in the United States. Despite advances in diagnosis and therapy, there has been no significant improvement in its 5-year relative survival rate for more than a decade. Surgical removal of cancerous tissue is still the primary treatment modality of HNSCC. Surgery results in approximately 60% chance of local regional recurrence within 5 years, and that can be as high as 90% if the margin is positive following resection. Unfortunately, positive margins are detected in close to 25% of patients. While pre surgical imaging and experience aid the surgical planning, intraoperative margin decisions are made primarily by vison and palpation. Thus, any practical imaging method that improves the accuracy of intraoperative detection of tumor tissue along the margin is highly likely to lead to reduced recurrence, increased survival, and a reduction in disfigurement caused by normal tissue removal.

The major conventional imaging modalities, MRI and PET/CT, have very limited application intraoperatively due to their large size and slow image collection times. Recently, Near infrared Fluorescent (NIRF) imaging or Optical Surgical Navigation (OSN) has emerged as a viable option. This technique operates in real time and is sensitive enough to detect nM dicyanine dyes targeted to cancer receptors. IRdye800-labeled antibodies are currently undergoing preclinical and clinical investigation in HNSCC: anti-EGFR (cetuximab) and anti-CD147. Antibodies are relatively simple to discover once a target has been isolated and validated. Small peptides, however, can be equally strong and specific target binders, and have the potential to penetrate tissue and be eliminated more rapidly. They are also generally less expensive to scale up, develop, and commercialize.

Several new HNSCC targeted peptides have been explored. Three peptides based upon cyclic arginine-glycine-aspartate (RGD) have been identified. $\alpha v\beta 3$ and other integrins are known to overexpressed on the surface of human HNSCC cells. Hsiao et al discovered an $\alpha v\beta 6$ specific peptide via biopanning phage. An HNSCC-binding peptide (HBP-1), discovered by Nothelfer et al, is composed of RGD and LXXL motifs, and binds $\alpha v\beta 6$ integrin in preference. Further to the application, Atallah et al reported that a Cy5-labeled RGD-based peptide can detect tiny tumor tissues unrecognized by human eyes during resection in a mouse cheek orthotopic model, and that removal of those tissues lengthened mice survival.

The oldest peptide developed for HNSCC, HN1, is the only one whose HNSCC cell affinity has been reproduced in multiple laboratories. HN1 was discovered through phage—display screening of human HNSCC cancer cells, and validated in human HNSCC cells in vitro, ex vivo human cancer tissue, and in vivo mouse tumor xenografts, using an optically labeled analog, HN1-FITC. Because it is internalized in cancer cells, HN1 was subsequently successfully explored as a carrier of anticancer agents. Bao et al confirmed HN1 internalization and found that HN1-PKCepsilon conjugate was internalized in HNSCC cells and blocked the activity of PKCε, inhibiting tumor growth in a xenografted mouse model. Un et al showed that HN1-anti-hRRM2, a peptide-siRNA conjugate, was internalized in HNSCC and human breast carcinoma cells and suppressed expression of endogenous hRRM2. These studies all used sub optimally long (>24 h) incubation times to demonstrate reliable internalization of HN1. Recognizing this problem, Dudas et al explored a wider range of conditions for HN1 binding and scrambled the peptide sequence, making HNscr, which did not differ significantly in uptake from HN1. They concluded that HN1 was not very sensitive to amino acid sequence, but did require the long incubation periods.

A second deficiency of HN1 for OSN applications is that the dyes attached so far emit far below the 800 nm near infrared region where all clinical in vivo surgical imagers operate. To operate in room light with maximum depth of penetration, current imagers are optimized for detection of the non-tumor specific, FDA approved optical dye, indocyanine green. The mechanism of action of HN1 is also unknown, although it behaves like a cell penetrating peptide. Disclosed herein are systematic studies that created new hybrid peptide containing molecules that have a greatly increased uptake rate and internalization in HNSCC cells compared to HN1, and also use a clinically useful NIRF dye as the fluorescent label. The best new molecule exhibits all of the positive features of HN1 but with 27 fold internalization rate increase at 1 h in cultured cells, and much stronger emission intensity in mice xenograft HNSCC tumor imaging.

a) Materials and Methods (1) Materials.

Resins, reagents and all amino acids were purchased either from AAPPTEC or CHEMIMPEX International Inc. The solvents for the syntheses and purifications were procured from PHARMCO-AAPER Inc. at reagent grade. The peptides were assembled using an Endeavor 90 Solid Phase Peptide Synthesizer manufactured by AAPPTEC Inc.

(2) Agent Synthesis

Peptide conjugate molecules displayed herein were synthesized in two stages. The starting peptide molecules were procured using solid phase peptide synthesis (SPPS) using standard Fmoc protection strategy. Thus, for each mmol of the amine on the resin, protected amino acid 4.0 mmol was activated with 4.0 mmol of the appropriate coupling agent like HATU or HBTU and 8.0 mmol of DIEA (Diisopropylethylamine) for 5 min. Then the activated acid was transferred to the amine on the solid phase and the reaction vessel was shaken for an hour. The final products and the protection groups were released from the resin (process repeated twice, 10 mL) using a cocktail containing trifluoroacetic acid (TFA), phenol, trisisopropylsilane (TIPS) and water in a ratio of 95:2:2:1 and then the mixture precipitated into methyl-tert-butyl ether. The precipitate was filtered and the crude solid was purified on preparative HPLC [Shimadzu preparatory purification unit (LC8A)] using a C18 column (10 µm, 50×250 mm, 60 min runtime at 100 mL/min) with water (0.1% TFA): MeCN (0.1% TFA)-10-100% solvent. Fractions with >90% purity were pooled and checked for the product by MS (mass spectrum analysis). The fractions with the required mass and purity >90% were pooled and freeze dried to yield the product as a colorless fluffy solid.

The preparation of HN17 required that the final coupling be performed by replacing amino acid N-Fmoc-O-tert-butyl-L-threonine by Emoc-4-Iodo-L-Phenylalanine. The removal of Fmoc protection in the dye conjugates f-HN-1-IR800 and 83B to afford f-HN1-IR800 and 83A was accomplished by incubating the same with 20% diethyl amine in acetonitrile at ambient temperature. The reaction was monitored by HPLC and was terminated by evaporation under vacuum that was followed by HPLC purification to afford the desired product.

(3) Fluorescent Labeling.

To an equimolar amount (0.00065 mmols) of the purified peptide and IR800-NHS ester in DMSO (dry, 250 µL) was added 4-methyl morpholine (5 µL). The resultant mixture was incubated at 40 oC for 1 h. After the completion of the reaction (ascertained by LC/MS, MALDI) the product was isolated by preparative HPLC on a Sunfire (Waters) C18 (30×250 mm, 5 µm) column with 30 mL/min flow rate. The solvent system consisted of the solvent A (0.1% TFA, in water) and B (0.1% TFA in acetonitrile) with gradient of solvent B ascending from 5 to 70% over 60 min. After the analysis the final compound was collected and lyophilized to afford a greenish blue product in approximately 90% purity. The fluorescent label, Cy5, was made in the same way.

High resolution MS were used to confirm the product identity. For each synthesized dye conjugate peptide molecule a matrix assisted laser desorption/ionization time-of-flight (MALDI-TOF) was used and performed on a Balker Daltonics UltrafleXtreme™ (Bruker Daltonics, Breman, Germany) mass spectrometer operated in reflection, positive ion mode with a N2 smartbeam II™ later (337 nm). Later power was used at the threshold level required to generate signal and acquired at 1000 Hz until suitable data were obtained. The instrument was calibrated with the Peptide Calibration Standard II purchased from Bruker Daltonics which contains Angiotensin II, Angiotensin I, Substance P, Bombesin, ACTH clip 1-17, ACTH clip 18-39, Somatostatin 28, Bradykinin Fragment 1-7, Renin Substrate Tetradecapeptide porcine with a covered mass range: ~700 Da-3200 Da.

Analysis of the purity (>90%) of the synthesized products and starting peptides was performed using a Shimadzu LC-10ATvp model, and Waters C18-RP analytical column (XBridge cartridge, 150×4.6 mm, 3.5 µm, flow rate=1 mL/min) starting at 80:20 buffer A/buffer B for the first 10 minutes and then linear gradient over 20 min to 30:70 buffer A/buffer B. The HPLC peaks for dye-conjugated products were visualized with a fluorescence detector (RF-10AXL, Shimadzu) detecting NIRF emission and the purity was in each case >90% by relative HPLC peak area at 750-820 nm. The starting peptide peaks were visualized with s UV-Vis detector (220 nm) and the purity was >90% by relative HPLC peak area. A (4) Cell Lines.

Human oral squamous carcinoma cell line, Cal 27, was purchased from American Type Culture Collection (ATCC, CAT #CRL-2095.) and maintained at 37° C. with 5% CO2 in DMEM supplemented with 10% fetal bovine serum (FBS) and 100 U penicillin/streptomycin. Cells were passaged twice per week.

(5) Cell Uptake.

Cal 27 cells were seeded at 7,000-12,000/well in a 96 well plate in triplicate for each reaction. To determine proper concentrations, cell culture medium was replaced after 24 h with 150 µL of medium per well containing 0-30 µM HN peptides. Cells were then incubated for 48 h at 37° C. with 5% CO2. To determine proper incubation duration, the medium was replaced after 24-48 h with 150 µL of medium per well containing 10 µM HN peptides and incubated for 2-48 h. For screening experiments, the medium was replaced after 24 h with 150 µL of medium per well containing 0-10 µM HN peptided and incubated for 1-2 h. Cells were then washed in 150 µL of PBS 5 times. PBS was removed completely after the last wash and cells were lysed in 60 µL lysis buffer (62.5 mM Tris-HCl (pH 6.8), 2% SDS, and 10% glycerol). Fluorescence intensity was measured using a BioTek Synergy H4 plate reader with ex/em at 764/809 nm for IR800-conjugates and 485/528 nm for FITC conjugates. Agent f-HN1-IR800 was included in the Cal 27 cell screening experiments for newly developed agents and readings of f-HN1-IR800 at 10 µM were set arbitrarily as 100% or 1. All other readings were compared to it. Cell numbers were controlled by a duplicate plate with the same treatment.

(6) Fluorescence Microscopy Assay.

Cal 27 cells were seeded at 70,000/well in duplicate on eight-well chamber slides and allowed to attach overnight. Cell culture medium was replaced with 200 µL medium containing 10 µM agents. Cells were incubated at 37° C. for 1-24 h followed by washing four times with 300 µL of HEPES buffer (25 mM HEPES 150 mM NaCl at pH 7.4) and once with the buffer containing 1 µg/mL DAPI. The chamber slide scaffold was then removed. Each chamber was then covered by a drop of aqua-poly mount and a coverslip, and sealed with clear nail polish. Cells were imaged with an Olympus IX81 microscope using an 800 nm emission filter set for IRDye800 conjugates and 461 nm for DAPI. Confocal imaging was performed using 4Iphf-HN18-Cy5 on an Olympus confocal microscope. Cell washing for the confocal microscopy was using growth media. FBS protein binding assay.

Agents 4Iphf-HN18-IR800 and HN1-IR800 (final concentration 25 μM) were incubated in 400 μL of FBS at room temperature for 30 s. The concentration was chosen based on expected intravenous imaging doses of 40 nmol in a 20 g mouse with a blood factor of 0.078, Solutions (300 μL) were then loaded into an Amicon unit (0.5 mL, 10 K cutoff) and centrifuged at 12,000 g for 15 min. Samples from the filtrate (50 μL), residual (5 μL), and original solution (5 μL) were loaded in duplicate into black wall 96-well plates containing 50 (for filtrate) or 95 (for residual and original) μL of PBS with 0.2% BSA. For an additional wash, 300 μL of PBS was then added into the Amicon unit. The unit was centrifuged as above. The same amounts of each of the parts were loaded into wells. Fluorescence units for each fraction were calculated by fraction volume×fluorescent unit/μL.

(7) In Vitro Serum Stability.

Agents 4Iphf-HN18-IR800 and HN1-IR800 (final concentration 6.4 μM) were incubated in 200 μL of fresh mouse serum (from nu/nu mice) at 37° C. for 0, 0.5, 1.5. 3, and 6 h. Agents were separated from serum proteins by addition of 2% of SDS, followed by mixing with 100 μL ice-cold ETOH and 300 μL of CAN, and centrifuged at 12,000 g for 20 min at 4° C. The liquid phase (50 μL) was analyzed by HPLC with a C18 inverted column and detected via 800 rim emission fluorescence using a shinadzu RF-10AXL fluorescence HPLC detector. Separate control samples included buffer only, 4Iphf-HN18-IR800 and HN1-IR800, and IRdye800-CW. Quantities of agents were determined based on the peak areas in the chromatograms. A degradation curve was fit and a half-life calculated using MS Excel.

(8) Blood Clearance.

Normal female Balb/c mice, 6- to 8-week old, were used. Blood samples (5 μL) were collected from the saphenous vein at 2 min, 0.5, 1, 3, 6, and 24 h postinjection (p.i.), and loaded into a 96-well plate with each well containing 95 μL of PBS with 0.15% EDTA (pH 8.5) and 0.2% BSA. Mice urine was collected until 3 h p.i. For urine accumulation analysis, 1 μL of urine was loaded into the 96-well plate in triplicate and diluted with 95 uL of PBS. Blood and urine samples from an uninjected mouse were used as a negative control. Fluorescence intensity was measured using the BioTek Synergy H4 plate reader. The total blood fluorescence (% ID/blood) (ID is injected dose) for each mouse was calculated as (blood volume×fluorescent unit per μL blood)/(fluorescent unit per μL ID×100), and 3 h urine excretion for each mouse was calculated as (% ID/urine) equals (urine volume×fluorescent unit/μL urine)/(fluorescent unit per μL×100). Blood volume was calculated based upon mouse weight. Fluorescence change in blood was plotted versus time using Microsoft Excel software. All data are presented as mean (SD). A Student's t-test (Microsoft Excel Software) was employed to analyze the difference between two points. A p value of 0.05 was considered to be statistically significant.

(9) In Vivo Imaging.

All experiments using live animals were conducted in accordance with protocols approved by The Ohio State University Institutional Animal Care and Use Committee. Female nude mice (nu/nu), 5-7 wk old, were purchased from Charles River, Cal 27 cells (1.5×107) in 100 μL PBS were inoculated subcutaneously in the left flank. Tumor size was measured twice a week and the volume was calculated using a formula: length×width×width/2. The diet for mice was shifted from regular to fluorescence reduced (CAT #TD.97184, Harlan, Wis.) chow one week before imaging.

When the tumors grew approximately to 150 mm3, the mice were injected via tail vein with 40 nmol of 4Iphf-HN18-IR800 or HN1-IR800 in 100 μL of PBS with 10% DMSO. The animals were imaged using both a CRi Maestro white light excitation imager (CRi Inc., Woburn, Mass., USA) and a laser excitation Fluobeam™ 800 NIR imaging system (Fluoptics, Grenoble, France). Briefly, imaging was performed with whole and skinned mice, ex vivo tumors with similar sizes of skeletal muscle, and tumors were sliced into 2 mm thickness with a similar dimension from the muscle. The intensity of fluorescence of whole tumors and sliced tumors were measured against their muscle control using Image J software and relative ratios were calculated.

b) Results (1) Syntheses and Nomenclature.

Figure 1:
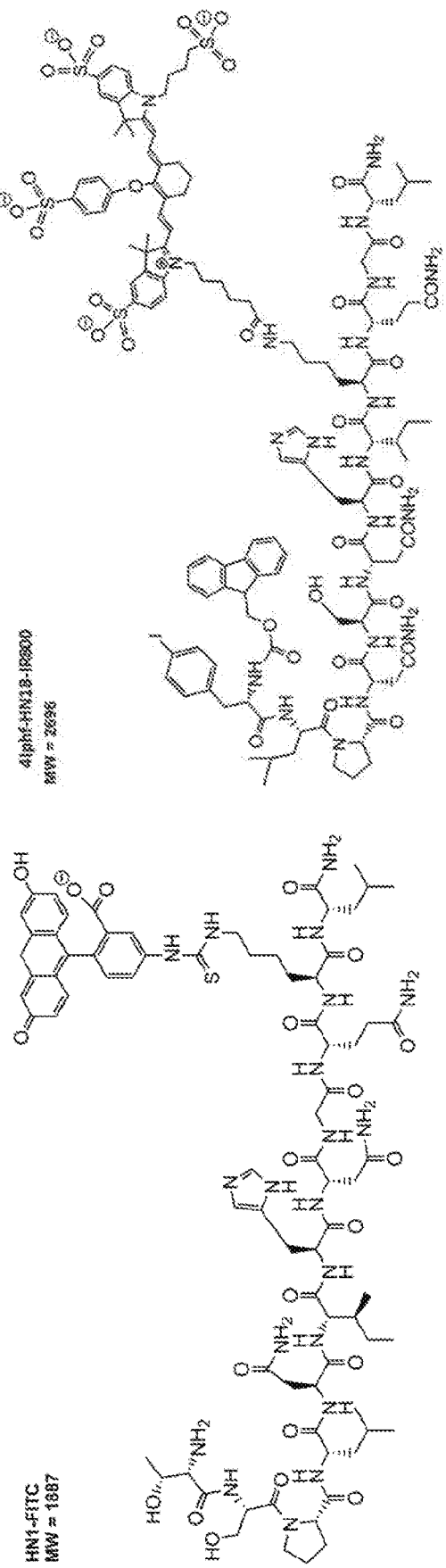
Figure 1:

Table 3 contains the peptides synthesized and studied along with named abbreviations, and FIG. 1 shows the structure and abbreviations of the dyes discussed. The original names of the HN1 and HN-J derived peptides were retained, adding the conjugated fluor as a suffix, e.g. HN1-FITC or HN1-IR800, and abbreviated additional amino acids and organic moieties at C-terminus as, e.g. f-HN1-IR800 for the N-terminal Fmoc adduct of the HN1 sequence conjugated at K with IRDye800-NHS. Further shown is that 4Iphf-HN18 is similar to f-HN17 but has the terminal Threonine (T) substituted with a 4-Iph.

TABLE 3

| compound names and peptide sequences as single letter codes | |
|---|---|
| Name | Sequence |
| HN1 | TSPLNIHNGQKL (SEQ ID NO: 2) |
| f-HN1 | T(f)SPLNIHNGQKL |
| 4Iph-HN1 | T(4Iph)SPLNIHNGQKL |
| HNJ | NQHSKNTLLIGP (SEQ ID NO: 4) |
| f-HNJ | N(f)QHSKNTLLIGP |
| HNscr | LNKQTHGLIPNS (SEQ ID NO: 3) |
| f-HN17 | T(f)LPNSNHIKQGL |
| 4Iphf-HN18 | (4Iph)(f)LPNSNHIKQGL (SEQ ID NO: 7) |

Polar amino acids are boldface.
F-Fmoc; 4Iph = 4-para-iodo-benzyl for HN17 or HN18 series, and 4-para-iodo-benzoyl for HN1 series.
Dyes are conjugated to lysine (K).

The initial attempt to reproduce the original HN1-FITC by conjugating FITC-NHS to the synthesized HN1 peptide resulted in a mixture of three peptides with FITC conjugated to either and both threonine (T) and lysine (K), as determined by MS. Details of published syntheses of HN1-FITC and HN1-Cy5 conjugations were insufficient to conclude whether single peptides or mixtures were used in those biological experiments. To generate discrete conjugates with the dyes conjugated to lysine, the peptides were always conjugated with the FITC or IR800-NHS (FIG. 1) before removing the terminal Fmoc. Fmoc can then be optionally removed. Three groups of molecules were studied: the original HN1 sequence was one, and a second was based on the original negative control "jumbled" peptide, HN-J, wherein the seven polar amino acids are clustered adjacent at the N-terminus. A new third group was made with a novel sequence of the same amino acids, HN17.

(2) In Vitro Studies.

Figure 2A:
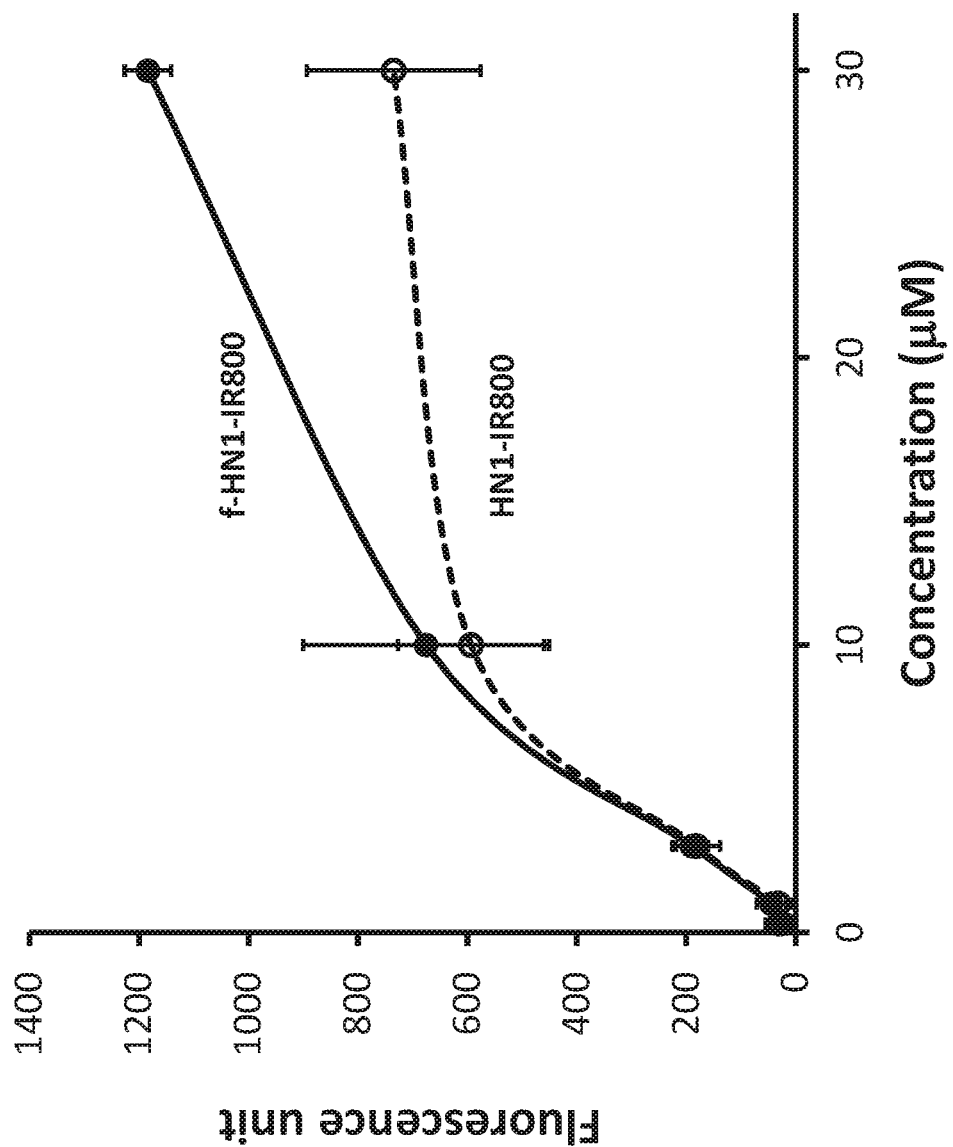
Figure 2B:
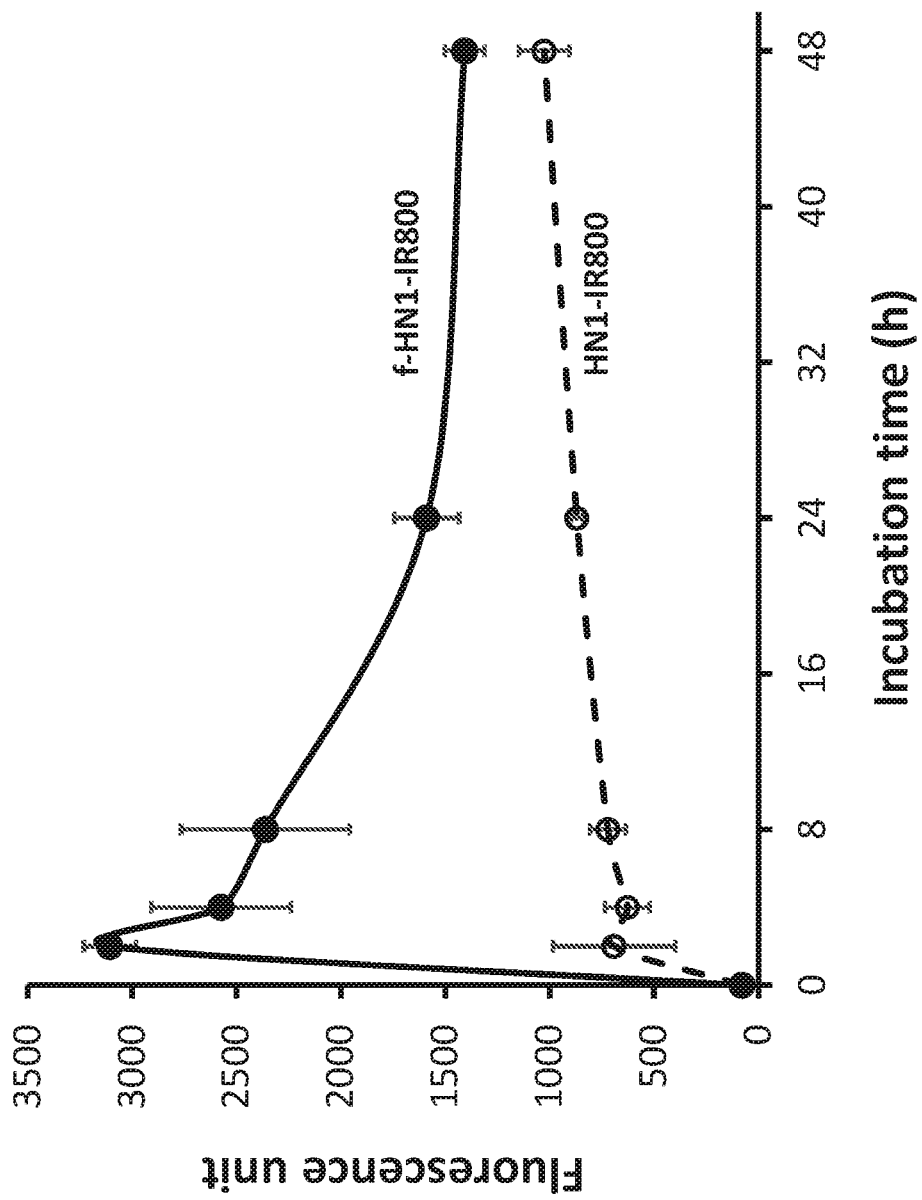
Figure 2C:
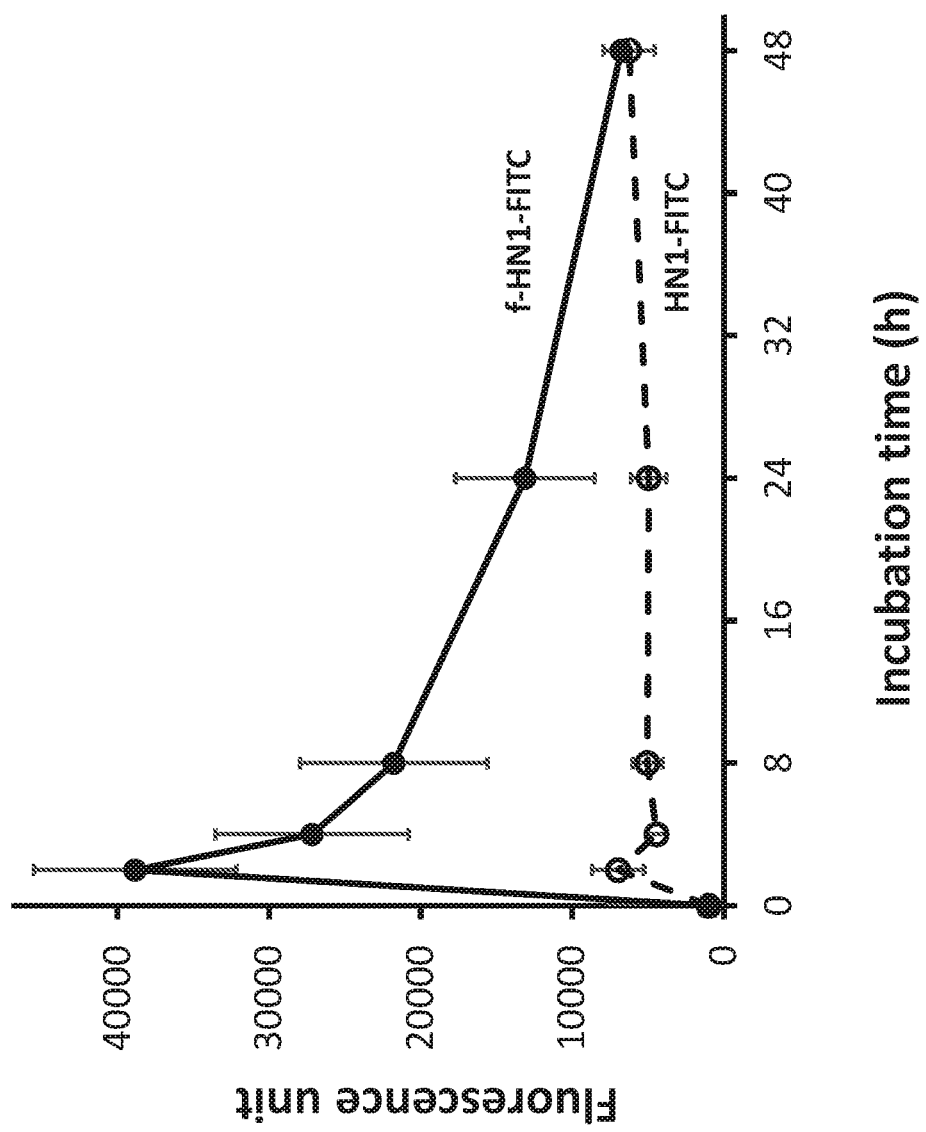

The aim was to determine whether shorter incubations were possible, Prior published work consistently found uptake in several HNSCC cells and only very minimal uptake in immortalized but not transformed human epithelial cells. The HN1-FITC and HN1-IR800 were compared and found no significant difference in the rate of uptake in Cal 27 HNSCC cells (FIGS. 2B and 2C). Thereafter, the IR800 derivatives only were studied, using Cal 27 cells consistently. Experiments started with a condition of 30 µM as the highest concentration and used a 48 h incubation. As shown in FIG. 2A, agent uptake by the cells was approximately saturated at 10 µM at 48 h for both HN1-IR800 and f-HN1-IR800, only a small increase being observed when the concentration was increased to 30 µM. Clearly, however, the apolar lipophile, Fmoc appended to the N-terminus, increased the cellular uptake.

The effect of incubation time was determined by incubating Cal 27 cells with these two agents at 10 µM from 2 to 48 h. FIG. 2B shows the same relative uptake at all the time points, but that the f-HN-IR800, but not HN1-IR800 peaked at 2 h then gradually declined to a plateau at 24-48 h. This phenomenon was repeatable in other peptides of the series bearing lipophilicity at the N terminus, including the FITC-labeled analogs (FIG. 2C). The data demonstrate that N-terminal Fmoc peptides can have greater uptake at shorter incubation times regardless of the dye used, while the overall capacity for accumulating the dye at long times appears to be much less affected by terminal Fmoc. Further screening was performed in Cal 27 cells with 1-2 h incubations in a concentration series, using f-HN1-IR800 as an internal control to normalize the data.

Figure 3:
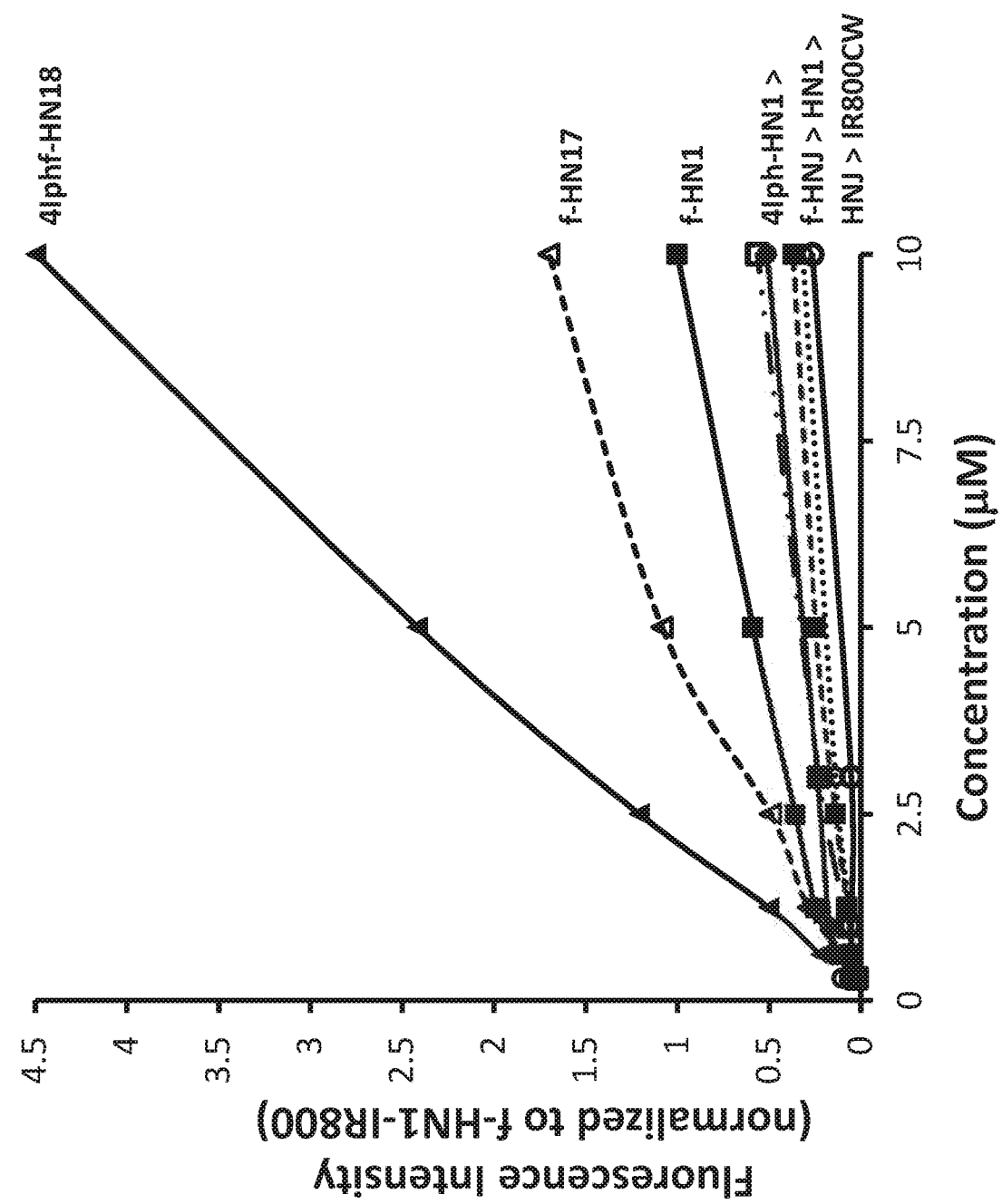

The full series of new peptides' screening results at 2 h incubations are shown in FIG. 3. Similar to the findings of Hong et al for HNJFITC, the HN-J-IR800 showed poor uptake, no better than the free IRDye-800-CW (CW=an unreactive carboxylate in place of NHS). Addition of an Fmoc to the polar end of the sequence, f-HN-J-IR800, increased the uptake significantly. The third, group of peptides were synthesized by separating the polar and apolar amino acids from the HN1 sequence. The 4-iodo-phenyl group was tested as a more polarizable lipophile than Fmoc. The series of molecules now spans a >12 fold range. The range of fluorescence emission was 30%, which is not significant compared to the effects seen in FIG. 3. The 2 h incubation period tends to magnify the effect that is seen with the 24-48 h incubations, but the order of uptake into the cells is the same. The Fmoc and 4Iph N terminal substitutions, and the polar amino acid separation independently increased the Cal 27 uptake.

Cellular uptake of 4Iphf-HN18-IR800 was also confirmed by a fluorescence microscopic assay. Cal 27 cells uptake was bright at both 1 h and 24 h, with emission intensity much brighter at 1 h than at 24 h, consistent with the macroscopic fluorescence signal changes. In contrast, there was little fluorescent signal captured at 800 nm in the cells incubated with HN1-IR800 or HN-J-IR800, or IRDye800CW at either 1 h or 24 h.

Prior to in vivo studies the serum protein binding potential and serum stability was ascertained. 25 µM 4Iphf-HN18-IR800 is a slightly stronger protein binder than HN1-IR800. There was approximately 70% and 52% bound to FBS at in 100% FBS. To verify that the protein binding does not provide the primary mechanism of uptake, uptake was measured with and without FBS in the media, finding that the FBS substantially diminished the cell uptake, probably by reducing the concentration of peptide available to the primary uptake mechanism. Testing 2% albumin against protein free PBS showed that binding albumin likewise significantly reduced cell uptake. At the 10% FBS used in the binding experiments, the proteins reduce the Cal 27 uptake. If it is assumed that these two compounds represent most of the range in the series, it can concluded that protein binding is a variable in the cellular uptake, stronger protein binding reducing cell uptake by reducing the concentration of the free peptide available for internalization. But the mechanism of uptake does not involve free protein binding.

Figure 4A:
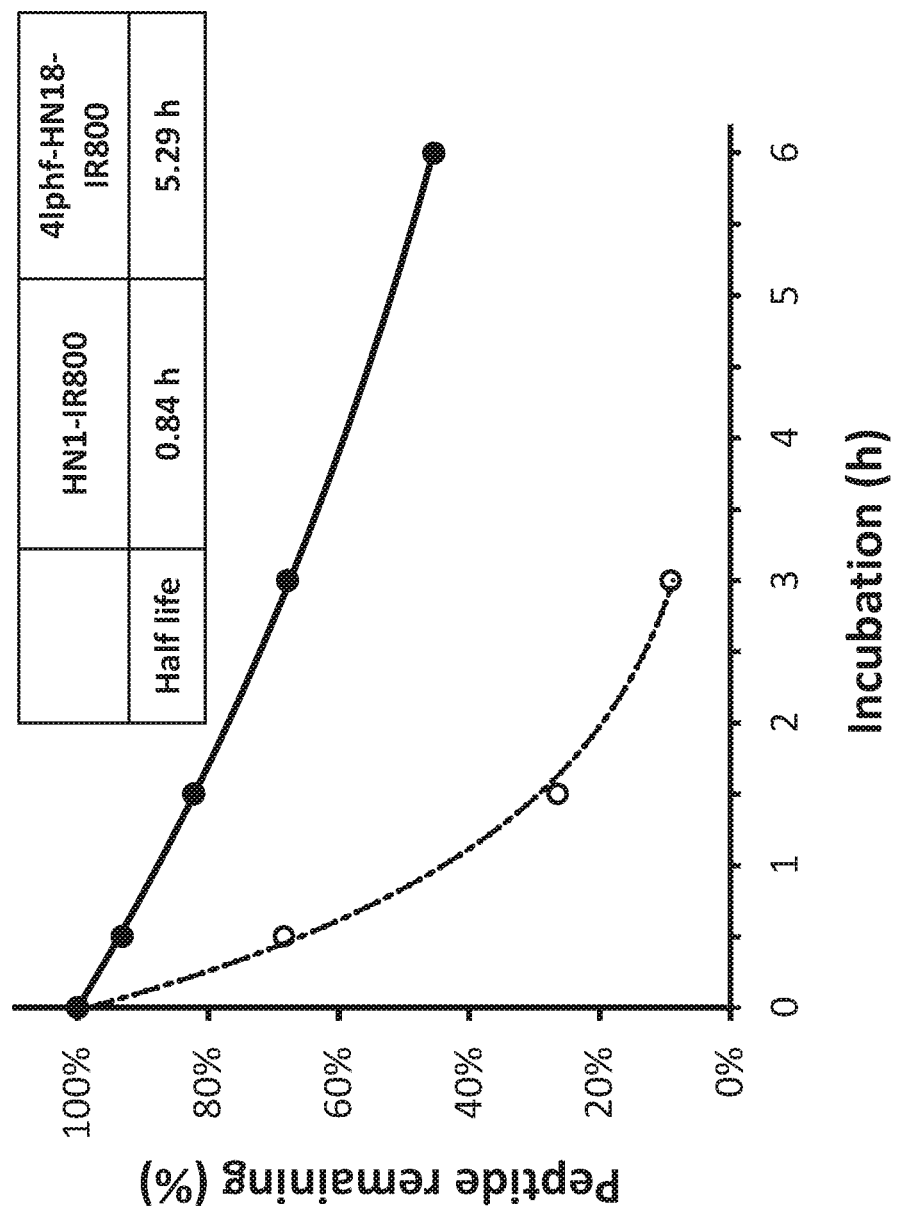
FIG. 4A shows metabolism of 4Iphf-HN18-IR800 (solid line) and HN1-IR800 (broken line) in 100% mouse serum. The peptide quantities were determined by peak areas of the intact molecule in HPLC chromatograms detected via fluorescence.

Serum stability was investigated as an important factor for an agent to maintain its effective concentration in vivo. As shown in FIG. 4A, 4Iphf-HN18-IR800 had a serum half-life 6.3 fold longer than HN1-IR800 in mouse serum at 37° C. (5.29 h vs 0.84 h). At the 40 nmol intravenous dose, the initial plasma concentration was estimated to be ~50 uM depending on hematocrit, and so has easily sufficient stability to target the tumor before being metabolized. It is interesting that the de novo selected peptide sequence of HN17 had greater resistance to serum degradation than the phage derived HN1. The latter was created in growth media containing serum specifically to ensure its ultimate stability as an in vivo delivery agent, it is possible that the stronger protein binding of the HN17 or HN18 sequence contributes to the serum stability by isolating the peptide from serum peptidases.

(3) In Vivo Studies.

Figure 4B:
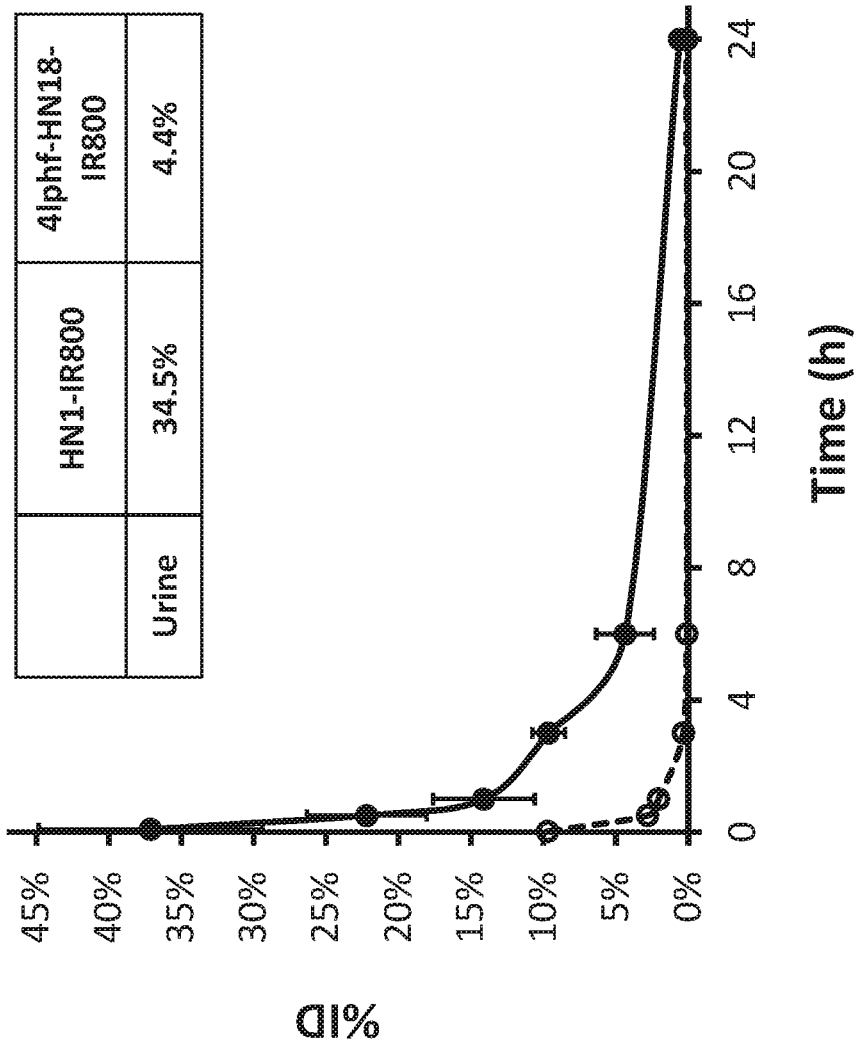
FIG. 4B shows blood clearance of peptides from mice administered 40 nmol doses i.v. with urine accumulation total at 3 h post administration detected via the fluorescence.

Blood clearance data for 4Iphf-HN18-IR800 and HN1-IR800 are shown in FIG. 4B and represent the range of behavior for the series. Both peptides displayed a rapid initial blood clearance or distribution phase followed by a slower blood clearance elimination phase with nearly complete clearance by 24 h. 4Iphf-HN18-IR800 exhibited a significantly slower clearance within the first 3 h (37.1% vs 9.7%, 22.2% vs 2.8%, 14.1% vs 2.1%, and 9.6% vs 0.3% at 5 min, 30 min, 1 h, and 3 h (p<0.05 at all the time points). The slower blood clearance of is consistent with its longer serum stability and stronger serum protein binding. The lipophilicity and protein binding also tend to produce greater hepatic versus renal excretion in small molecules, and 4Iphf-HN18-IR800 had only 4.4% ID in the urine within the first 3 h after intravenous administration compared to 34.5% for HN1-IR800. Based upon the in vitro and ex vivo data, both agents have sufficient bioavailability to function as tumor imaging agents in mice models.

Figure 5C:
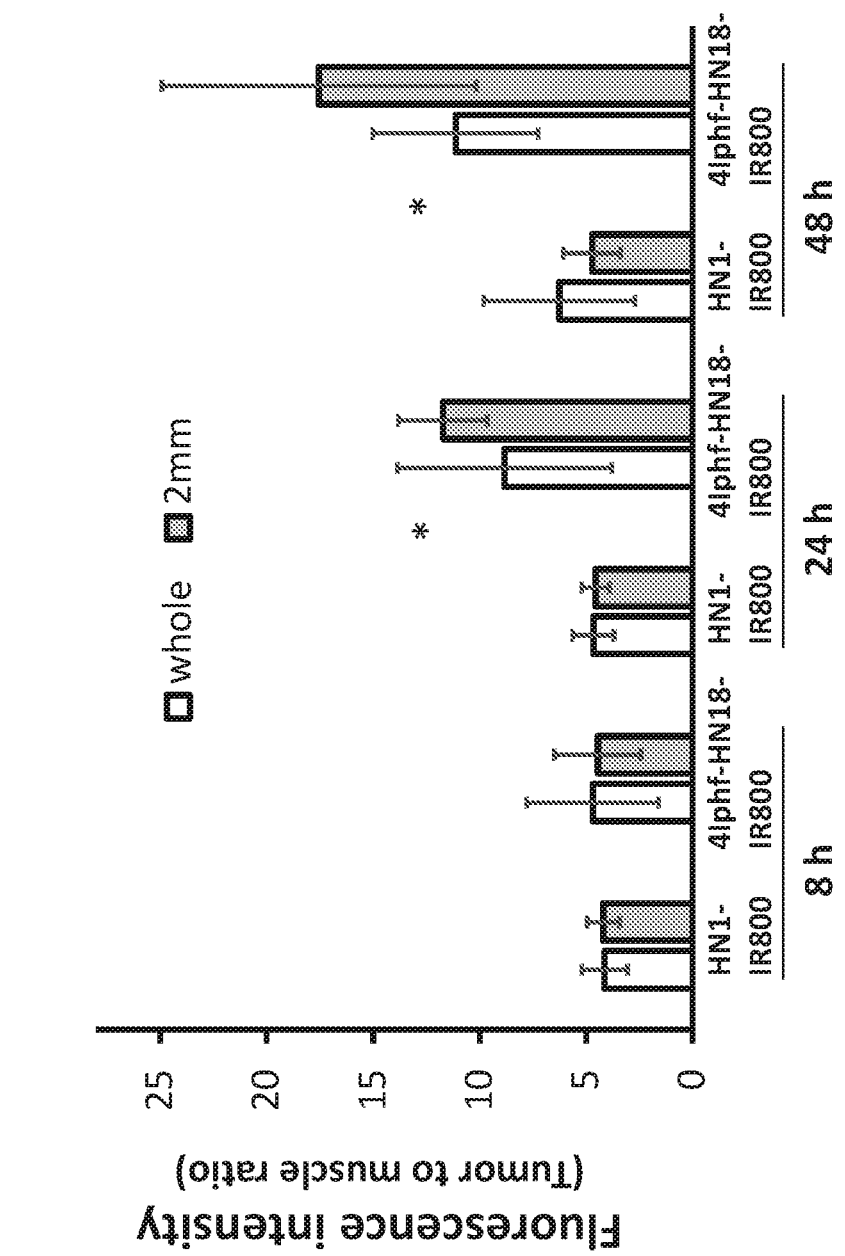
FIG. 5C shows the intensity of whole and sliced tumor and muscle. * are significant differences between HN-1-IR800 and 4Iphf-HN18-IR800 by paired t test (n=4: 24, 48 h, n=3: 8 h).

4Iphf-HN18-IR800 was further investigated in mice bearing Cal 27 flank xenograft tumors. Based on a pilot dose testing study, 40 nmol per mouse was chosen. First, the mice were imaged at various times to determine the change in fluorescence intensity in the tumor and whole mice with time. The dye used is well known to provide a high tissue background at earlier times. but counter balancing this, uptake in tumors was also slow to wash out. As shown in FIG. 5A, tumors gradually stood out prominently when the background signal in whole mouse was cleared. The best contrast of tumor to body background appeared at 48 h. This was also found for UM-SCC-1 tumor mice and orthotopically implanted medullary thyroid tumor mice. In contrast, tumors in mice administered 40 nmol of HN1-IR800 exhibited a similar fluorescence intensity in tumor and in the rest of the body during the whole observation period. Tumors with 4Iphf-HN18-IR800, but not HN1-IR800, became more distinguishable after the mouse was euthanized and skinned (FIG. 5B). To better compare and semi-quantitate the fluorescence intensity, excised tumors were first imaged adjacent to similar masses of excised skeletal muscle and then re-imaged after being sliced into 2 mm thickness samples. As shown in FIG. 5C, tumors of 4Iphf-HN18-IR800 had much greater tumor to muscle signal ratios for both whole tumor and 2 mm thickness sections at 48 h (11.1 vs 6.3 for whole tumor, and 17.5 vs 4.2 for 2 mm thickness tumor, n=4, p<0.05).

To further examine the imaging potential at early time points, paired mice were injected with HN1-IR800 and 4Iphf-HN18-IR800, euthanized, and imaged at 8 and 24 h. High uptake in mouse skin interfered with tumor imaging in the whole mouse prior to 24 h. FIG. 5C shows tumor to muscle ratio values for ex vivo tissues. The tumor to muscle contrast ratios were small at 8 h for both agents (3.8 vs 3.9 for whole tumor, and 3.0 vs 4.0 for 2 mm slices, n=3). The values improved somewhat from 24 to 48 h for 4Iphf-HN18-IR800, while the ratios in f-HN1-IR800 did not change significantly. The tumor to muscle ratios at 24 h and 48 h were also significantly greater than those in HN1-IR800 (8.8 vs 4.7 for whole tumor, and 11.7 vs 4.6 for 2 mm thickness, n=4, p<0.05 for both).

The greater tumor signal and tumor to muscle ratio of 4Iphf-HN18-IR800 vs HN1-IR800 is probably a result multiple factors: (1) the molar fluorescence emission of 4Iphf-HN1-IR800 is approximately 1.5 fold greater than HN1-IR800 in when serum proteins are present. (2) The blood clearance of 4Iphf-HN18-IR800 is slower, exposing the tumor to the agent for a longer time. (3) The cancer cell uptake of 4Iphf-HN1-IR800 is much faster and equilibrates at a higher concentration. (4) The stability in mouse serum was greater. These factors outweighed the stronger serum protein binding that reduces the bioavailability for tumor uptake.

To further show the localization of 4Iphf-HN18 at the target cell, live Cal 27 cells treated with 4Iphf-HN18-Cy5 and imaged on a confocal microscope. live Cal 27 cells treated with 4Iphf-HN18-Cy5 and then after washing, stained to reveal microscopic structures of the cells. The 4Iphf-HN18-Cy5 was clearly located inside the HNSCC cancer cells, Cal 27. The dye corresponds with the cytosol of the cells showing that HN18 penetrates the cell membrane and localizes past the membrane and into the cytosol. This feature makes HN18 valuable as a cell penetrating delivery device for cancer diagnosis and treatment.

c) Discussion.

Hong and Clayman derived HN1 from a phage library against a single HNSCC cell line. Performing cell internalization studies at 2.6 uM for 48 h: 1) HN1-FITC internalized in a time and dose dependent manner into six HNSCC cell lines but not immortalized untransformed epithelial cells, and not in a prostate cancer or a colon cancer cell line; 2) 200× HN1 inhibited uptake of HN1-FITC; 3) HN1-FITC stained human tumor tissue; 4) at 260 nmol dose, HN1-FITC localized in vivo in mouse xenograft tumors. Both ends of the 12-mer peptide can be extended several amino acids without interrupting internalization; 5) HN1 worked with Texas red as well as FITC labeling and in PBS as well as media and it was judged to be sequence specific based upon the negative internalization of a scrambled peptide, HNJ (same 12 amino acids). But Dudas rescrambled HN1 (HN-scr) and found no significant loss of function, concluding that the internalization and binding was not specifically sequence specific, but rather structure specific. The data does not resolve this issue for 24-48 h incubations on peptides without the lipophile-enhanced C termini, but does indicate that in the short 1-2 h incubation times with the lipophile enhanced peptides, the peptide sequence is highly significant. The serendipitous discovery that Fmoc left bound to the N terminus of HN1 improved uptake, led to the discovery of the improvement in early time uptake available through lipophilic substitution at the N-terminus.

The present work had the purpose of creating a useful HNSCC agent for Optical Surgical Navigation (OSN). Earlier work was based upon FITC and Cy5 dyes and the dye seemed not to inhibit internalization in Bao's therapeutic agent. CY5 is a dicyanine dye significantly different from FITC in structure. To explore the ability of HN1 to serve this function we substituted another dicyanine, IRDye800, a NIRF dye emitting in the optimal >800 nm range detectable with FDA approved optical imagersIRDye800 has a fully developed preclinical toxicology package, and its use as a label is being studied clinically conjugated to antibodies. Considering the molecular size of the dyes (FIG. 1) and the four negative sulfonates of IR800, it is somewhat surprising to observe HN1 being similarly functional under the same conditions labeled with either FITC, CY5 or IR800. Much more surprising, however, is the dramatic difference that the lipophiles make when appended to the C terminal amino acid. Among the lipophile-enhanced peptides, the second improvement was created by resequencing the peptidic portion of the molecule to centralize most of the polar amino acids, and centralize the NIRF dye, by moving the lysine toward the middle of the peptide. With a similar objective to improve cell uptake rate, Dudas moved the K-FITC label to the C terminal side of the middle, but the changes did not significantly improve on HN1-FITC performance.

Uptake rate improvement is due to a different mechanism than the one observed for HN1-FITC and HN1-CY5. All sequences are improved by the addition of the Fmoc, including the negative control, HNJ. Both HN1 and HN17 sequences improve when 4Iph and/or Fmoc are appended, and 4Iph and Fmoc effects are additive, despite structural dissimilarity, as evidenced in 4Iphf-HN18-IR800. By operational definition, the family of peptides with this amino acid composition, regardless of sequence, probably belongs in the Cell Penetrating Peptide (CPP) class. These molecules have been well known and studied for decades as drug targeting devices. Their functionality primarily in the micromolar concentration domain (i.e. weak binding) and ability to internalize are primary characteristics, although cancer specificity is not. The HN family is unusual, bearing overall charge from −1 to −3, depending solely on the dye chosen to track the peptide. Other classes of CPP are either highly cationic overall with multiple cationic amino acids, and used for delivery of covalently attached drugs, or amphipathic, containing sequential domains of hydrophilic and hydrophobic amino acids and used for delivery of non-covalently attached drugs. However, considering FITC, CY5 and IR800 as drug sized molecules, covalently attached, the HN peptides deviate from the CCP norm. The new hybrid organic-peptide compounds with a −3 overall charge is a new variant of the amphipathic CPP class, or be a new CPP class. The new hybrid lipophile-enhanced peptides show such dramatically different early time internalization that they probably are using a different, as yet unknown mechanism, possibly in combination with unknown mechanism of the HNI family.

d) Conclusion

Starting with a FITC-labeled, phage derived peptide, HN1-FITC, resequencing, and substituting N terminal lipophiles, and then labeling with a practical NIRF dye produced 4Iphf-HN1-IR800. The new optical agent has much more rapid tumor cell uptake, greater fluorescence brightness and improved in vivo tumor imaging characteristics. These features qualify it for further investigation as a practical imaging tool for optically guided HNSCC tumor resections. The new compounds behave like amphipathic CPP, with possible but unproven cancer specificity. Given the positive therapeutic results with HN1-PKCe and HN1-siRNA, there is also reason to expect more therapeutic effectiveness using the new targeting vectors.

2. Example 2

Biological Evaluation of a Novel Fluorescent-Imaging Agent for Medullary Thyroid Cancer in an Orthotopic Model An ideal molecule imaging agent will be readily absorbed, non-toxic, available during the surgical procedure, and eliminated shortly after surgery. This molecule would need to be diseased tissue specific with low uptake in normal tissues to reduce background activity. The molecule should be available intraoperatively to be seen easily by the surgeon. Near-infrared agents enable surgeon visualization of a fluorescence wavelength, not visible to the naked eye, with relatively low auto-fluorescence. IRdye800 provides better tissue penetrance and brightness than most other near-infrared agents while having a low toxicity profile, and thus was chosen as the label for the molecule.

A variety of NIRF agents have been developed that allow the targeting of tumor cells in a specific manner. While the purpose of these molecules has generally been drug delivery, their tumor specificity can also be exploited to enhance intraoperative imaging. The initial studies were based on a compound known as HN-1 that had previously been shown to have cancer cell killing effects when conjugated to a toxin or inhibitory peptide. Further development and labeling with IRDye-800 led to a compound with a much higher affinity to malignant cells.

Herein is described the properties of the novel imaging peptide in a biological context. It is demonstrated that this peptide has high affinity for two MTC cells in vitro and in vivo. The binding dynamics indicate the molecule behaves as a cell penetrating peptide, which may associate with mitochondria of MTC cells. The studies in a murine flank xenograft model verified the in vitro results, albeit with background fluorescence. To examine imaging with this molecule in situ an orthotopic xenograft model of MTC was established. This model allows us to examine localization of the imaging agent in a natural MTC setting by using existing vasculature and tumor microenvironment. It also decreases background fluorescence seen by the compound in the gastrointestinal and renal systems. In both in vivo models of MTC (flank xenografts & orthotopic xenografts) the imaging peptide resulted in significant fluorescence at the site of the xenograft. This imaging molecule can enhance surgical removal of MTC.

a) Material and Methods (1) Culture Of Cell Lines:

MZ-CRC1 cells were obtained from Dr. Robert Gagel (MD Anderson). TT cells were obtained from Dr. Barry Nelkin (Johns Hopkins University). All cells were verified mycoplasma free by PCR. All cells were verified to be of thyroid origin by short tandem repeat profiling. Twenty thousand cells were plated on Clear bottom/Black plate 96-well (Corning Costar #3603), and allowed to attach for 24 h at 37° C. in 1640 RPMI supplemented with 20% heat inactivated serum (Gibco Catalog #10437-028), 1% MEM non-essential amino acids (Gibco) and 1% L-glutamine (Gibco Catalog #25030-164).

(2) Subcutaneous Xenografts:

Cells were removed from the 10 $cm^3$ tissue culture dish by incubation with 0.25% trypsin EDTA (Gibco). Cells were rinsed in 1× PBS, and resuspended at 1×$10^7$ cells/mL in 1× PBS. For each of two cell lines (TT and MZ-CRC1) one million cells of each cell line were then combined with 100 µL of matrigel and injected into separate flanks (TT-right; MZ-CRC1 left) of athymic nude mice (5 weeks old, obtained from Target Validation Shared Resource at The Ohio State University). Development of tumors was monitored by visual examination until volumes can be determined by caliper measurements. Tumor volumes were determined using the formula: Tumor volume=1/2×(length×$width^2$). Once both tumors reached a minimum volume of 150 $mm^3$ the animals were injected with 40 nmoles of 4Iph-HN18-IR800 via tail-vein injection. Animals were imaged using CRi Maestro at three, six, 24, 36 and 48 hours following the injection.

(3) Near Infrared Fluorescence Imaging:

Forty-eight hours after injection the animals were euthanized and skinned for imaging. The tumors along with internal organs were removed for imaging. The animals were imaged using both a CRi Maestro white light excitation imager (CRi Inc., Woburn, Mass., USA) and a laser excitation Fluobeam™ 800 NIR imaging system (Fluoptics, Grenoble, France). Comparisons between tissues were made by placing all tissues relevant to the comparison in the same image to equalize exposure time.

(4) MTC Orthotopic Xenograft:

(a) Cell Preparations and Injection Protocol:

Cells were treated with 0.25% Trypsin EDTA to remove from culture dishes. Cells were rinsed and resuspended in 1× PBS at 5×$10^7$ cells/mL and kept on ice. Athymic nude mice (~5-6 weeks, TVSR) were anesthetized with isofluorane and skin sterilized by use of 4% chlorhexidine (Henry Schein Animal Health, Columbus, Ohio). A sterile field was established and a vertical cervical incision was made. Visualization was achieved by use of a dissecting microscope. Strap muscles and submandibular glands were separated and reflected, respectively, using blunt dissection. Once trachea and thyroid were adequately visualized ten microliters of cell suspension was injected into the target thyroid lobe using an insulin syringe needle (27 ga, Terumo, Somerset, N.J., USA). Submandibular tissue was re-approximated and the incision was closed by use of 6-0 absorbable surgical sutures. Mice were allowed to recover from anesthesia, returned to their cage and supplied with analgesics (ibuprofen 2 mg/mL) for seven days. All animal studies were done under protocols approved by The Ohio State University Laboratory Animals Recourse.

(5) Statistical Analysis:

Wilcoxon Rank-sums test were used to compare calcitonin levels between age-matched non-injected mice and mice bearing a xenograft. Spearman correlation was calculated for calcitonin concentration and the volume at necropsy.

(6) 4Iph-HN18-IR800 in Orthotopic Xenografts:

40 nmoles of 4Iph-IIN18-IR800 were into the animal via tail vein injection. The animals were imaged using both a CRi Maestro white light excitation imager (CRi Inc., Woburn, Mass., USA) and a laser excitation Fluobeam™ 800 MR imaging system (Fluoptics, Grenoble, France). Tumors and equal volume of muscle tissue excised and compared for fluorescence.

b) Results (1) Characterization of 4Iph-HN18-IR800 in an MTC Subcutaneous Flank Xenograft Model The localization of 4Iph-HIN18-IR800 was examined in a subcutaneous flank xenograft model for both MTC cells. Tumors that were at least 150 mm$^3$ were used in the experiment. 4Iph-HN18-IR800 was distributed relatively equally throughout the body up to 24 h (FIG. 7). Beginning at 24 h and through the end of the experiment, increased contrast was observed with background at the site of the xenografts and with additional contrast observed at 36 h and 48 h (FIG. 7). Both cell lines appear to be equally capable of concentrating 4Iph-HN18-IR800 within the corresponding xenograft (FIG. 7), indicating that calcium metabolism is not responsible for the uptake and retention of the agent.

(2) Characterization of Medullary Thyroid Cancer Orthotopic Xenografts

In order to examine the concentration of 4Iph-HN18-IR800 at the normal site of disease, orthotopic xenografts were established for both TT and MZ-CRC1 cell lines by injecting each cell line into the thyroid lobes of five (TT) or six (MZ-CRC1) animals. Xenografts were successfully established in all animals injected with the TT cell lines, and in five of six of the animals injected with the MZ-CRC1 cell line. Growth of the xenografts was followed weekly with 3D US starting at the second week after injection. Orthotopic xenografts were detectable as early as three weeks as a small hypodense nodule in the injected thyroid lobe. As the xenografts enlarged, they took on a round contour and remained hypodense compared to surrounding tissues. Larger tumors were observed to extend to the contralateral side of the neck posterior to the trachea and esophagus. There was little variability in growth between each orthotopic xenograft in animals injected with TT cells. Some difference was observed in final volume of orthotopic xenografts as calculated by the US software and volumes determined by caliper measurements following necropsy in xenografts derived from MZ-CRC1 cells.

(3) Imaging of 4Iph-HN18-IR800 in an MTC Orthotopic Model

An orthotopic xenograft was used to examine the ability of 4Iph-RN18-IR800 to accumulate at the site of the orthotopic xenograft. 4Iph-HN18-IR800 was principally found in the orthotopic xenograft of mice producing easily visualized fluorescence (FIG. 8). Importantly, surrounding tissue did not fluoresce, indicating that 4Iph-HN18-IR800 specifically is internalized/binds to tumor cell derived xenografts. Mice injected with the sequence jumbled control did not have specific (or indeed, any detectable) fluorescence (FIG. 8). There was not an observable correlation between tumor volume and the intensity of fluorescence.

A second orthotopic xenograft was used to examine the ability of 4Iph-HN18-IR800 to accumulate at the site of the orthotopic xenograft for breast cancer using MBA-MD-231 triple negative human breast cancer cells. MBA-MD-231 cells were implanted into two of the fat pads nude female mice. The growth rate of these tumors is shown in the FIG. 9A over time. In one of these mice with two such tumors, after the tumors grew to about 1 cm diameter, the mouse was injected with 40 nmol of f-HN18-IR800, and the images were recorded 24 hours later using a FluOptics Fluobeam optical surgical imager (FIG. 9B). The large white ovals in the optical image are the tumors demonstrating localization of the f-HN18-IR800 in the tumors.

c) Discussion

Disclosed herein is a biological evaluation of a novel near-infrared imaging molecule in medullary thyroid cancer. The initial experiments show that this molecule can bind and/or be internalized in two MTC cell lines using an in vitro assay. Microscopic evaluation using the same assay, along with the relatively high concentration needed for rapid internalization indicates that the molecule behaves as a cell penetrating peptide. Cellular localization of 4Iph-HN18-IR800 was examined in MTC cells using fluorescence microscopy and found that fluorescence in treated cells coincided with localization of mitochondria. This localization is due to internalization at that location or to localization of a fluorescent metabolite at that location. The control compound (83a) demonstrated virtually no fluorescence in vitro indicating specificity of 17. The mechanism by which 4Iph-HN18-IR800 binds to and enters the cells is presently unknown. Hong and Clayman described a peptide called HN1, which they found to be taken up by squamous cancer cells likely via receptor-mediated endocytosis, but that mechanism was not conclusively demonstrated. 4Iph-HN18-IR800 is partially derived from the same amino acids, and has a similar entry mechanism, but is far more rapidly taken up.

Specific fluorescence was also observed in flank xenografts, which was apparent through the skin. 4Iph-HN18-IR800 appeared to also accumulate in kidneys, indicating excretion through those organs. Also it indicates sonic affinity for nephrons. The examination of muscle tissue (thigh) from the same animal revealed very little fluorescence compared to xenografts providing excellent signal-to-background ratio. Interestingly, the agent appears to diffuse equally and extensively through the entire tumor. The agent does not appear to be retained in or near the blood vessels or lymphatics. This leads to a more complete visualization of all tumor tissues, and not just the well vascularized area of the tumor.

To better evaluate the practicality of 4Iph-HN18-IR800 in an intraoperative setting, an orthotopic model of MTC in mice was developed. Xenografts were established by direct injection into the thyroid bed during survival surgery. This allowed xenograft growth and development in a microenvironment that includes surrounding thyroid follicular cells, vasculature and paracrine signaling. This has not been described for MTC. The orthotopic location of the xenografts was confirmed by murine neck US, which provides a non-invasive method similar to that employed in humans. Alternative monitoring systems typically use bioluminescence, which requires genetically altered cells, MTC cell lines are slow-growing, and the process of introducing a luciferase gene may have detrimental effects, including the selection of subclones. Because of tumor heterogeneity and the nuance of using US, there may have been some animals that had incomplete US imaging of their tumors and as a result, the total volume of the tumors on 3D US underestimates the actual disease burden. While there is a learning curve in using US for this application, it is a valuable tool that allows use of unlabeled cell lines and is non-invasive. Overall it was found that growth curves are smooth and consistent among f animals, and that the volume of the tumors as recorded at final US closely approximates the volumes as measured during necropsy. While reports of PTC and. ATC orthotopic xenografts indicate large xenografts (100-200 mm$^3$) in four to five weeks, MTC orthotopic tumors achieved those large volumes between 9-10 weeks, correlating with their slow growth in vitro. Another helpful adjunct in evaluating tumor growth in the MTC orthotopic model is the measurement of serum calcitonin via ELISA assay. Calcitonin is a useful biomarker in humans with MTC. In animals with MTC xenografts, increased calcitonin concentrations was found compared to age- and sex-matched control animals. While this was not applicable to the evaluation of 4Iph-HN18-IR800 in these animals, this served as a proof-of-concept that calcitonin was produced by the tumors and can be used as a biomarker for xenograft growth and/or response to therapy. With further studies, calcitonin may be able to obviate the need to follow xenografts growth via other methods, The use 4Iph-HN18-IR800 in the MTC orthotopic model demonstrates its potential application in surgical resection. The tumors demonstrate intense fluorescence compared to surrounding tissues. There is minor background fluorescence in the surrounding muscle, trachea, and esophagus. The resolution of fluorescence is certainly subcentimeter and possibly on the order of 1 millimeter. In patients with widespread locoregional disease as well as in patients with locoregional recurrence in the reoperative setting, this level of resolution is valuable in differentiating scar tissue from active disease, This level of differentiation is even more valuable in sensitive regions such as around the recurrent laryngeal nerve and other cranial nerves during lateral neck dissection. The ability to discriminate between malignant and non-malignant tissue in real time without the need for biopsy is the ultimate goal in order to minimize risk to the patient and to obtain a more complete resection. While 4Iph-HN18-IR800 is an excellent candidate, further studies are necessary to move it forward for use in humans as well as to maximize its potential in other applications. This includes evaluating its breadth of sensitivity and specificity, mechanism of action, pharmacodynamics and pharmacokinetics, and tolerability. Determining the optimal timing of administration of the compound prior to imaging is needed to maximize the signal to background ratio. While there is appreciable work to be done, 4Iph-HN18-IR800 appears to have the potential for a significant impact for patients with MTC.

3. Example 3

Direct Penetration of Cell Membrane by Cell Penetrating Peptides

CY5-labeled analogs of the best peptide (4Iphf-HN18-CY5) were made to verify the internalization in live HNSCC cells using confocal microscopy. It was concluded form this that HN18 is indeed internalized, and that the primary subcellular fraction is in the cytoplasm. Actin stains the membrane location, Hoechst stains the nucleii. The confocal images clearly showed internalized 4Iphf-HN18-CY5 located in the cytosol. To perform the staining, cells were incubated in 5-10 uM 4Iphf-HN18-CY5 incubated for 1 h, and washed 5 times with cell growth media containing FBS (that binds to the hybrid peptides) in order to remove as much of the hybrid peptides as possible without damaging the cells.

To determine how the HN17 and HN18 were accessing the cytoplasm of the cells, it was understood that internalization could occur via direct penetration or endocytosis. To elucidate which mechanism was used, confocal images were again obtained, but now in the presence of various inhibitors.

By reducing the available heat energy the cell membrane sticking and internalization was stopped, not totally, but almost so (FIG. 10). This is consistent with both mechanisms; however, it also shows that the internalization is not some kind of physisorbtion that is not related to the living cell and its state of life. Furthermore, it means that the cell membrane sticking observed is a part of the overall mechanism. Kinetics later on shows that first step takes only seconds to a few minutes to occur.

To discern which internalization route was occurring, 4Iphf-HN18-CY5 was incubated with Cal-27 cells in the presence of various inhibitors (FIG. 11). The use of sodium azide shows that the internalization mechanism does not require significant cellular supplied energy as sodium azide depletes cellular ATP pool. This is consistent with direct penetration mechanism. Endocytosis is energy dependent. Each of the next four slides show internalization despite highly effective endocytosis inhibitors applied to the cells to stop the various types of endocytosis. Specifically, this result was shown by Nocodazole, methyl-β-cyclodextrin (MβCD), Chloropromazine, and amiloride inhibition. Nocodazole inhibits the formation of clartherin-coated pits and thus can test calthrin dependent endocytosis. MPCD inhibits the lipid raft-mediated caveolae pathway one of the major clathrin independent endocytotic pathways. Similarly, chloropromazine inhibits clathrin independent pathways of endocytosis. Lastly, amiloride inhibits micropinocytosis (i.e., non-receptor mediated endocytosis). AS noted above, each inhibition did not stop internalization. FACS are on FITC labeled hybrid peptide. They show that all of the cells are in the bulk are involved in the cell binding, and not just a few cells observed under the microscope. Thus, cell penetration via HN17 occurs via a direct mechanism.

Propidium iodide cannot enter cells and stain the nuclei blue unless there is a. novel mechanism at work, or the cells are dying or dead. The rightmost chart shows that the hybrid peptide does not damage the cells at the concentration and conditions used (FIG. 12). The left slide shows that, nevertheless, in the presence of HN18 the propidium iodide enters the cell and stains the nuclei blue. This is consistent with either mechanism, but since it is now known that the mechanism must be the direct one, the hybrid peptides must be creating small, harmless and temporary cell membrane defects that allow the Propidium iodide temporary access to the cytosol, from where it migrates to the nucleus. It cannot be strongly bound to the hybrid peptide since it targets the nucleus, while the hybrid peptide stays in cytosol. This phenomenon allows for targeted therapeutics that are not even conjugated to the hybrid peptide, simply by mixing and administering the therapeutic along with the hybrid peptide.

To further investigate the penetration of the HN18 peptide and more specifically, the 4Iphf-HN18 to penetrate cells, Cal 27 live The 4Iphf-HN18-Cy5 penetrates from bulk solution to the cell membrane in seconds, then penetrates into the cytosol visibly within 5 minutes, continuing to move into the cell over the next 25 minutes unfixed cells were contacted with 4Iphf-HN18-Cy5 (FIG. 13).

F. REFERENCES

Antonello Z A & Nucera C 2014 Orthotopic mouse models for the preclinical and translational study of targeted therapies against metastatic human thyroid carcinoma with BRAF(V600E) or wild-type BRAE *Oncogene* 33 5397-5404.

Bao L, Gorin M A, Zhang M, et al. (2009) Preclinical development of a bifunctional cancer cell homing, PKCepsilon inhibitory peptide for the treatment of head and neck cancer. Cancer Res 69:5829-5834.

Bihan H, Becker K L, Snider R H, Nylen E, Vittaz L, Lauret C, Modigliani E, Moretti J L & Cohen R 2003 Calcitonin precursor levels in human medullary thyroid carcinoma. *Thyroid* 13 819-822.

Cabanillas M E, Hu M I, Durand J B & Busaidy N L 2011 Challenges associated with tyrosine kinase inhibitor therapy for metastatic thyroid cancer. *J Thyroid Res* 2011 985780.

Carson F L & Cappellano C H 2009 *Histotechnology: a self-instruction text*. [Chicago]: ASCP Press.

Chau N G & Haddad R I 2013 Vandetanib for the treatment of medullary thyroid cancer. *Clin Cancer Res* 19 524-529.

Cheung K, Wang T S, Farrokhyar F, Roman S A & Sosa J A 2012 A meta-analysis of preoperative localization techniques for patients with primary hyperparathyroidism. *Ann Surg Oncol* 19 577-583.

Fagin J A & Wells S A J 2016 Biologic and Clinical Perspectives on Thyroid Cancer. *New England Journal of Medicine* 375 1054-1067.

Faustino-Rocha A, Oliveira P A, Pinho-Oliveira J, Teixeira-Guedes C, Soares-Mala R, da Costa R G, Colaco B, Pires M J, Colaco J, Ferreira R, et al. 2013 Estimation of rat mammary tumor volume using caliper and ultrasonography measurements. *Lab Anim (NY)* 42 217-224.

Fischer A H, Jacobson K A, Rose J & Zeller R 2008 Hematoxylin and eosin staining of tissue and cell sections. *CSH Probe* 2008 pdb prot4986.

Fogal V, Richardson A D, Karmali P P, Scheffler I E, Smith J W & Ruoslahti E 2010 Mitochondrial p32 protein is a critical regulator of tumor metabolism via maintenance of oxidative phosphorylation. *Mol Cell Biol* 30 1303-1318.

Fogal V, Zhang L, Krajewski S & Ruoslahti E 2008 Mitochondrial/cell-surface protein p32/gC1qR as a molecular target in tumor cells and tumor stroma. *Cancer Res* 68 7210-7218.

Gotthardt M, Lohmann B, Behr T M, Bauhofer A, Franzius C, Schipper M L, Wagner M, Hoffken H, Sitter H, Rothmund M, et al. 2004 Clinical value of parathyroid scintigraphy with technetium-99m methoxyisobutylisonitrile: discrepancies in clinical data and a systematic metaanalysis of the literature. *World J Surg* 28 100-107.

Hong F D & Clayman G L 2000 Isolation of a peptide for targeted drug delivery into human head and neck solid tumors. *Cancer Res* 60 6551-6556.

Marshall M V, Draney D, Sevick-Muraca E M & Olive D M 2010 Single-dose intravenous toxicity study of IRDye 800CW in Sprague-Dawley rats. *Mol Imaging Biol* 12 583-594.

Morrison J A, Pike L A, Lund G, Zhou Q, Kessler B E, Bauerle K T, Sams S B, Haugen B R & Schweppe R E 2015 Characterization of thyroid cancer cell lines in murine orthotopic and intracardiac metastasis models. *Horm Cancer* 6 87-99.

Nguyen Q T, Olson E S, Aguilera T A, Jiang T, Scadeng M, Ellies L G & Tsien R Y 2010 Surgery with molecular fluorescence imaging using activatable cell-penetrating peptides decreases residual cancer and improves survival. *Proc Natl Acad Sci USA* 107 4317-4322.

Nucera C, Nehs M A, Mekel M, Zhang, X, Hodin R, Lawler J, Nose V & Parangi S 2009 A novel orthotopic mouse model of human anaplastic thyroid carcinoma. *Thyroid* 19 1077-1084.

Ruoslahti E 2016 Tumor penetrating peptides for improved drug delivery. *Adv Drug Deliv Rev*.

Schweppe R E, Klopper J P, Korch C, Pugazhenthi U, Benezra M, Knauf J A, Fagin J A, Marlow L A, Copland J A, Smallridge R C, et al. 2008 Deoxyribonucleic acid profiling analysis of 40 human thyroid cancer cell lines reveals cross-contamination resulting in cell line redundancy and misidentification. *J Clin Endocrinol Metab* 93 4331-4341.

Stummer W, Novotny A, Stepp H, Goetz C, Bise K & Reulen H J 2000 Fluorescence-guided resection of glioblastoma multiforme by using 5-aminolevulinic acid-induced porphyrins: a prospective study in 52 consecutive patients. *J Neurosurg* 93 1003-1013.

Stummer W, Pichlmeier U, Meinel T, Wiestler O D, Zanella F & Reulen H J 2006 Fluorescence-guided surgery with 5-aminolevulinic acid for resection of malignant glioma: a randomised controlled multicentre phase III trial. *Lancet Oncol* 7 392-401.

Tweedle M F 2009 Peptide-targeted diagnostics and radiotherapeutics. *Acc Chem Res* 42 958-968.

Un F, Zhou B & Yen Y 2012 The utility of tumor-specifically internalizing peptides for targeted siRNA delivery into human solid tumors. *Anticancer Res* 32 4685-4690.

Vanden Borre P, Gunda V, McFadden D G, Sadow P M, Varmeh S, Bernasconi M & Parangi S 2014 Combined BRAF(V600E)- and SRC-inhibition induces apoptosis, evokes an immune response and reduces tumor growth in an immunocompetent orthotopic mouse model of anaplastic thyroid cancer. *Oncotarget* 5 3996-4010.

Verbeek H H G, Plukker J T M, Koopmans K P, de Groot J W B, Hofstra R M W, Muller Kobold A C, van der Horst-Schrivers A N A, Brouwers A H & Links T P 2012 Clinical Relevance of 18F-FDG PET and 18F-DOPA PET in Recurrent Medullary Thyroid Carcinoma. *Journal of Nuclear Medicine* 53 1863-1871.

Wells S A, Jr., Asa S L, Dralle H, Elsei R, Evans D B, Gagel R F, Lee N, Machens A, Moley J F, Pacini F, et al. 2015 Revised American Thyroid Association guidelines for the management of medullary thyroid carcinoma. *Thyroid* 25 567-610.

Yagi M, Uchiumi T, Takazaki S, Okuno B, Nomura M, Yoshida S, Kanki T & Kang D 2012 p32/gC1qR is indispensable for fetal development and mitochondrial translation: importance of its RNA-binding ability. *Nucleic Acids Res* 40 9717-9737.

What is claimed is:

1. An isolated peptide that targets a tumor cell, wherein said peptide comprises the amino acid sequence of TLPNSNHIKQGL (SEQ ID NO: 1), TSPLNIHNGQKL (SEQ ID NO: 2), LNKQTHGLIPNS (SEQ ID NO: 3), NQHSKNTLLIGP (SEQ ID NO: 4), LKQGNHINLPS (SEQ ID NO: 5), YSPLNIHNGQKL (SEQ ID NO: 6), LPNSNHIKQGL (SEQ ID NO: 7), YLPNSNHIKQGL (SEQ ID NO: 8), or FLPNSNHIKQGL (SEQ ID NO: 9).

2. The peptide of claim 1, wherein the peptide further comprises a lypophile attached to the amino terminal amino acid.

3. The peptide of claim 2, wherein the lypophile comprises Fluorenylmethyloxycarbonyl, 4-para-iodo-benzyl, 4-para-iodo-benzoyl, and/or 3-iodotyrosine.

4. A composition comprising: a) an anti-cancer drug; and b) a peptide that targets a tumor cell, wherein said peptide comprises the amino acid sequence of TLPNSNHIKQGL (SEQ ID NO: 1), TSPLNIHNGQKL (SEQ ID NO: 2), LNKQTHGLIPNS (SEQ ID NO: 3), NQHSKNTLLIGP (SEQ ID NO: 4), LKQGNHINLPS (SEQ ID NO: 5), YSPLNIHNGQKL (SEQ ID NO: 6), LPNSNHIKQGL (SEQ ID NO: 7), YLPNSNHIKQGL (SEQ ID NO: 8), or FLPNSNHIKQGL (SEQ ID NO: 9).

5. The composition of claim 4, wherein said anti-cancer drug is a chemotherapeutic agent, cytotoxic agent, apoptotic agent, DNA-damaging agent, plant alkaloid, and/or radio sensitizer.

6. The composition of claim 4, wherein said anti-cancer drug comprises cisplatin, carboplatin, procarbazine, mechlorethamine, cyclophosphamide, ifosfamide, melphalan, chlorambucil, bisulfan, nitrosurea, dactinomycin, daunorubicin, doxorubicin, bleomycin, plicomycin, mitomycin, etoposide, docetaxel, cetuximab, tamoxifen, transplatinum, 5-fluorouracil, vincristin, vinblastin or methotrexate.

7. The composition of claim 6, wherein the anti-cancer drug is covalently attached to the peptide.

8. The composition of claim 7, wherein the anti-cancer drug is covalently attached to the peptide at a lysine residue.

9. The composition of claim 4, wherein the peptide further comprises a lypophile attached to the amino terminal amino acid.

10. The composition of claim 9, wherein the lypophile comprises Fluorenylmethyloxycarbonyl, 4-para-iodo-benzyl, 4-para-iodo-benzoyl, and/or 3-iodotyrosine.

11. The composition of claim 4, wherein said peptide is internalized by said tumor cell.

12. The composition of claim 4, wherein the composition further comprises a detectable conjugate.

13. The composition of claim 12, wherein the peptide is SEQ ID NO: 1 or SEQ ID NO: 7, the lipophiles are 4Iph and f, and the detectable label is a NIRF dye or IR800.

14. A method of treating a cancer in a subject comprising administering to the subject a composition comprising a peptide, wherein said peptide comprises the amino acid sequence of TLPNSNHIKQGL (SEQ ID NO: 1), TSPLNIHNGQKL (SEQ ID NO: 2), LNKQTHGLIPNS (SEQ ID NO: 3), NQHSKNTLLIGP (SEQ ID NO: 4), LKQGNHINLPS (SEQ ID NO: 5), YSPLNIHNGQKL (SEQ ID NO: 6), LPNSNHIKQGL (SEQ ID NO: 7), YLPNSNHIKQGL (SEQ ID NO: 8), or FLPNSNHIKQGL (SEQ ID NO: 9) and the peptide is covalently attached to an anti-cancer drug.

15. The method of claim 14, wherein the peptide further comprises a lypophile attached to the amino terminal amino acid.

16. The method of claim 14, wherein the lypophile comprises Fluorenylmethyloxycarbonyl, 4-para-iodo-benzyl, 4-para-iodo-benzoyl, and/or 3-iodotyrosine.

17. The method of claim 14, wherein said anti-cancer drug comprises cisplatin, carboplatin, procarbazine, mechlorethamine, cyclophosphamide, ifosfamide, melphalan, chlorambucil, bisulfan, nitrosurea, dactinomycin, daunorubicin, doxorubicin, bleomycin, plicomycin, mitomycin, etoposide, docetaxel, cetuximab, tamoxifen, transplatinum, 5-fluorouracil, vincristin, vinblastin or methotrexate.

18. The method of claim 14, wherein the anti-cancer drug is covalently attached to the peptide at a lysine residue.

19. The method of claim 14, wherein said peptide is internalized by said tumor cell.

20. The method of claim 14, wherein the composition further comprises a detectable conjugate.

21. A method of detecting a cancer cell in a subject comprising administering to the subject a composition comprising a peptide, wherein said peptide comprises the amino acid sequence of TLPNSNHIKQGL (SEQ ID NO: 1), TSPLNIHNGQKL (SEQ ID NO: 2), LNKQTHGLIPNS (SEQ ID NO: 3), NQHSKNTLLIGP (SEQ ID NO: 4), LKQGNHINLPS (SEQ ID NO: 5), YSPLNIHNGQKL (SEQ ID NO: 6), LPNSNHIKQGL (SEQ ID NO: 7), YLPNSNHIKQGL (SEQ ID NO: 8), or FLPNSNHIKQGL (SEQ ID NO: 9); wherein the peptide is conjugated to a detectable label.

22. The method of claim 21, wherein the detectable label comprises Cy5, IR800, or NIRF dye.

23. The method of claim 21, wherein the peptide further comprises a lypophile attached to the amino terminal amino acid.

24. The method of claim 23, wherein the lypophile comprises Fluorenylmethyloxycarbonyl, 4-para-iodo-benzyl, 4-para-iodo-benzoyl, and/or 3-iodotyrosine.

25. The method of claim 23, wherein the peptide is SEQ ID NO: 1 or SEQ ID NO: 7, the lipophiles are 4Iph and f, and the detectable label is a NIRF dye or IR800.

* * * * *